United States Patent
Ren et al.

(10) Patent No.: US 11,406,646 B2
(45) Date of Patent: Aug. 9, 2022

(54) COMPOSITIONS COMPRISING 5-CHOLESTEN-3, 25-DIOL, 3-SULFATE (25HC3S) OR PHARMACEUTICALLY ACCEPTABLE SALT THEREOF AND AT LEAST ONE CYCLIC OLIGOSACCHARIDE

(71) Applicants: Virginia Commonwealth University, Richmond, VA (US); Durect Corporation, Cupertino, CA (US)

(72) Inventors: Shunlin Ren, Richmond, VA (US); Leyuan Xu, Richmond, VA (US); Yanxia Ning, Richmond, VA (US); Jin Koung Kim, Richmond, VA (US); WeiQi Lin, Emerald Hills, CA (US); Andrew R. Miksztal, Palo Alto, CA (US); Hongwei Wu, Cupertino, CA (US); Min L. Lee, Saratoga, CA (US)

(73) Assignees: Virginia Commonwealth University, Richmond, VA (US); Durect Corporation, Cupertino, CA (US); The United States Government as Represented by The Department of Veterans Affairs, Washington, DC (US)

( * ) Notice: Subject to any disclaimer, the term of this patent is extended or adjusted under 35 U.S.C. 154(b) by 0 days.

(21) Appl. No.: 17/094,432

(22) Filed: Nov. 10, 2020

(65) Prior Publication Data
US 2021/0169898 A1    Jun. 10, 2021

Related U.S. Application Data

(63) Continuation of application No. 16/320,079, filed as application No. PCT/US2017/044840 on Aug. 1, 2017, now abandoned.

(60) Provisional application No. 62/470,578, filed on Mar. 13, 2017, provisional application No. 62/370,024, filed on Aug. 2, 2016.

(51) Int. Cl.
| | | |
|---|---|---|
| A61K 31/565 | (2006.01) | |
| A61P 1/16 | (2006.01) | |
| A61K 31/724 | (2006.01) | |
| A61K 47/10 | (2017.01) | |
| A61K 31/575 | (2006.01) | |
| A61K 47/40 | (2006.01) | |
| A61P 17/06 | (2006.01) | |
| A61P 3/06 | (2006.01) | |
| A61P 31/04 | (2006.01) | |
| A61Q 19/00 | (2006.01) | |
| A61K 8/73 | (2006.01) | |
| A61K 9/19 | (2006.01) | |
| A61K 9/00 | (2006.01) | |
| A61K 8/63 | (2006.01) | |
| C07J 31/00 | (2006.01) | |

(52) U.S. Cl.
CPC .............. *A61K 31/565* (2013.01); *A61K 8/63* (2013.01); *A61K 8/738* (2013.01); *A61K 9/0019* (2013.01); *A61K 9/19* (2013.01); *A61K 31/575* (2013.01); *A61K 31/724* (2013.01); *A61K 47/10* (2013.01); *A61K 47/40* (2013.01); *A61P 1/16* (2018.01); *A61P 3/06* (2018.01); *A61P 17/06* (2018.01); *A61P 31/04* (2018.01); *A61Q 19/00* (2013.01); *A61Q 19/004* (2013.01); *A61Q 19/007* (2013.01); *C07J 31/006* (2013.01)

(58) Field of Classification Search
CPC .... A61K 31/565; A61K 31/724; A61K 47/10; A61K 47/6951; A61P 1/16
See application file for complete search history.

(56) References Cited

U.S. PATENT DOCUMENTS

| | | |
|---|---|---|
| 3,822,254 A | 7/1974 | Partridge et al. |
| 3,836,527 A | 9/1974 | Irmscher et al. |
| 3,928,397 A | 12/1975 | Ikekawa et al. |
| 4,202,891 A | 5/1980 | Schroepfer et al. |
| 4,225,524 A | 9/1980 | Ochi et al. |
| 4,264,512 A | 4/1981 | Okamura et al. |
| 4,427,668 A | 1/1984 | Javitt |
| 4,727,064 A | 2/1988 | Pitha |
| 4,743,597 A | 5/1988 | Javitt et al. |
| 5,599,659 A | 2/1997 | Brasile et al. |
| 6,645,953 B2 | 11/2003 | Gronvald et al. |

(Continued)

FOREIGN PATENT DOCUMENTS

| | | |
|---|---|---|
| CN | 1357003 | 7/2002 |
| EP | 0857173 | 11/2003 |

(Continued)

OTHER PUBLICATIONS

Stranz, M. "The implications of osmolality, osmolarity and pH . . . " INS Annual Conference, pp. 1-5, https://piccresource.com/Short%20IV%20Insertion%20Sample/Short%20IV%20Insertion%20Self%20Study/data/downloads/marc%20stranz%202005%20fall%20ins%20handout.pdf Accessed from the internet Jul. 7, 2020 (Year: 2005).*

(Continued)

*Primary Examiner* — Leigh C Maier
(74) *Attorney, Agent, or Firm* — Khin K. Chin; Bozicevic Field & Francis LLP

(57) ABSTRACT

Compositions comprising 5-cholesten-3,25-diol, 3-sulfate (25HC3S) or pharmaceutically acceptable salt thereof and at least one cyclic oligosaccharide, e.g., a cyclodextrin (CD), are provided. The compositions may be used to prevent and/or treat a variety of diseases and conditions, including organ failure (e.g. acute liver failure), high cholesterol/high lipids, and various inflammatory diseases and conditions.

20 Claims, 21 Drawing Sheets

(56) References Cited

U.S. PATENT DOCUMENTS

| | | |
|---|---|---|
| 6,923,988 B2 | 8/2005 | Patel et al. |
| 7,524,493 B2 | 4/2009 | Flugelman et al. |
| 8,399,441 B2 | 3/2013 | Ren et al. |
| 9,034,859 B2 | 5/2015 | Ren et al. |
| 9,321,802 B2 | 4/2016 | Ren et al. |
| 9,480,692 B2 | 11/2016 | Ren |
| 10,786,517 B2 | 9/2020 | Ren et al. |
| 2001/0015676 A1 | 8/2001 | Hayden et al. |
| 2002/0107233 A1 | 8/2002 | Liao et al. |
| 2003/0077297 A1 | 4/2003 | Chen et al. |
| 2003/0153541 A1 | 8/2003 | Dudley et al. |
| 2004/0048838 A1 | 3/2004 | Gronvald et al. |
| 2004/0152681 A1 | 8/2004 | Liao et al. |
| 2005/0101573 A1 | 5/2005 | Faarup et al. |
| 2006/0025393 A1 | 2/2006 | Liao et al. |
| 2007/0197484 A1 | 8/2007 | Song et al. |
| 2007/0275939 A1 | 11/2007 | Ren et al. |
| 2008/0078099 A1 | 4/2008 | Schulz et al. |
| 2009/0088192 A1 | 4/2009 | Davis et al. |
| 2010/0093687 A1 | 4/2010 | Song et al. |
| 2010/0273761 A1 | 10/2010 | Ren et al. |
| 2011/0077245 A1 | 3/2011 | Van der Aa et al. |
| 2011/0160174 A1 | 6/2011 | Song et al. |
| 2012/0264816 A1 | 10/2012 | Ren et al. |
| 2013/0143854 A1 | 6/2013 | Ren et al. |
| 2015/0072962 A1 | 3/2015 | Ren |
| 2016/0355544 A1 | 12/2016 | Ren |
| 2017/0136038 A1 | 5/2017 | Ren |
| 2018/0127457 A1 | 5/2018 | Ren |
| 2018/0346509 A9 | 12/2018 | Ren et al. |
| 2019/0135856 A1 | 5/2019 | Ren |
| 2019/0169225 A1 | 6/2019 | Ren et al. |
| 2019/0350945 A1 | 11/2019 | Ren et al. |
| 2019/0374554 A1 | 12/2019 | Ren et al. |
| 2020/0009158 A1 | 1/2020 | Ren |
| 2020/0138831 A1 | 5/2020 | Ren et al. |
| 2020/0157140 A1 | 5/2020 | Ren |
| 2020/0222430 A1 | 7/2020 | Miksztal et al. |
| 2021/0147469 A1 | 5/2021 | Ren et al. |
| 2021/0238219 A1 | 8/2021 | Ren |

FOREIGN PATENT DOCUMENTS

| | | | |
|---|---|---|---|
| EP | 2842547 | 3/2015 | |
| EP | 3639828 | 4/2020 | |
| WO | WO 1993025568 | 12/1993 | |
| WO | WO 1994003177 | 2/1994 | |
| WO | WO 1995015165 | 6/1995 | |
| WO | WO 1997000884 | 1/1997 | |
| WO | WO 1999058549 | 11/1999 | |
| WO | WO 2000066611 | 11/2000 | |
| WO | WO 2001015676 | 3/2001 | |
| WO | WO 2002062302 | 8/2002 | |
| WO | WO 2002090375 | 11/2002 | |
| WO | WO 2003039480 | 5/2003 | |
| WO | WO 2004017897 | 3/2004 | |
| WO | WO 2006047022 | 5/2006 | |
| WO | WO 2008078099 | 7/2008 | |
| WO | WO 2009088192 | 7/2009 | |
| WO | WO 2011077245 | 6/2011 | |
| WO | WO 2012017290 | 2/2012 | |
| WO | WO 2012074244 | 6/2012 | |
| WO | WO 2013036835 | 3/2013 | |
| WO | WO 2013154752 | 10/2013 | |
| WO | WO 2014015024 | 1/2014 | |
| WO | WO 2015100312 | 7/2015 | |
| WO | WO-2016057713 A1 * | 4/2016 | ............ A61P 43/00 |
| WO | WO 2016058000 | 4/2016 | |
| WO | WO 2017019808 | 2/2017 | |

OTHER PUBLICATIONS

Cal, K. et al "Use of cyclodextrins in topical formulations . . . " Eur. J. Pharm. Biopharm., vol. 68, pp. 467-478. (Year: 2008).*

Ferrante Jr., et al (2001) "Effects of Leptin Deficiency and Short-Term Repletion on Hepatic Gene Expression in Genetically Obese Mice"; Diabetes 50(10); pp. 2268-2278.

Kasisk, et al. (1988) "Pharmacologic treatment of hyperlipidemia reduces glomerular injury in rat 5/6 nephrectomy model of chronic renal failure"; Circulation Research vol. 62, No. 2; pp. 367-374.

Levine, et al (2006) "Argatroban Therapy in Heparin-Induced Thrombocytopenia With Hepatic Dysfunction"; Chest, vol. 129, Issue 5; pp. 1167-1175.

Ren et al., "25-Hydroxycholesterol sulfation regulates lipid metabolism in vivo in mice", Jun. 13-14, 2008; Abstract.

Spahr et al. (2011) "Early liver biopsy, intraparenchymal cholestasis, and prognosis in patients with alcoholic steatohepatitis"; BMC Gastroenterology, 11:115; pp. 2-9.

Zaffanello, et al (2009) "Acute non-oliguric kidney failure and cholestatic hepatitis induced by ibuprofen and acetaminophen: a case report"; Acta Paediatr 98(5); pp. 903-905.

Abildayeva et al., "24(S)-Hydroxycholesterol Participates in a Liver X Receptor-controlled Pathway in Astrocytes That Regulates Apolipoprotein E-Mediated Cholesterol Efflux", The Journal of Biological Chemistry, May 5, 2006, pp. 12799-12808, vol. 281, No. 18, American Society for Biochemistry and Molecular Biology, Inc.

Accad et al. "Cholesterol homeostasis: A role for oxysterols", Current Biology, 1998, p. R601-R604, vol. 8.

Adams et al., "Cholesterol and 25-Hydroxycholesterol Inhibit Activation of SREPBs by Different Mechanisms, Both Involving SCAP and Insigs", The Journal of Biological Chemistry, Dec. 10, 2004, pp. 52772-52780, vol. 279, No. 50, American Society for Biochemistry and Molecular Biology, Inc.

Agarwal et al., "CTLA-4 gene polymorphism confers susceptibility to primary biliary cirrhosis"; Journal of Hepatology vol. 32, Issue 4, Apr. 2000, pp. 538-541.

Ahmed et al., "PPARs and their Metabolic Modulation: New Mechanisms for Transcriptional Regulation?", Journal of Internal Medicine, 2007, vol. 262, p. 184-198.

Aksoy IA, et al., "Cholesterol Sulfation in human liver. Catalysis by dehydroepiandrosterone sulfotransferase"; Drug Metab Dispos. 21:268-276, 1993.

Australian New Zealand Clinical Trials Registry (ANZCTR), "A Multiple Daily Oral Dose Study of DUR-928 in Healthy Volunteers", Trial ID ACTRN 12615000267550, Mar. 20, 2015, web.

Australian New Zealand Clinical Trials Registry (ANZCTR), "A Single Infusion of DUR-928 in Healthy Volunteers", Trial ID ACRTN 12616000856415, Jun. 30, 2016, web.

Australian New Zealand Clinical Trials Registry (ANZCTR), "A Single Injection Dose Study of DUR-928 in Patients with Impaired Kidney Function and Healthy Volunteers" Trial ID ACTRN 12616000389404, Jun. 24, 2016, web.

Australian New Zealand Clinical Trials Registry (ANZCTR), "A Single Oral Dose Study of DUR-928 in Nonalcoholic Steatohepatitis (NASH) Patients and Healthy Volunteers", Trial ID ACTRN 12515001355561, Dec. 14, 2015, web.

Australian New Zealand Clinical Trials Registry (ANZCTR), "A Single and Multiple Daily Injection Study of DUR-928 in Healthy Volunteers", Trial ID ACTRN 12615000903583, Aug. 28, 2015, web.

Australian New Zealand Clinical Trials Registry (ANZCTR), "an Intralesional Injection Study of DUR-928 in Psoriasis Patients" Trial ID ACRTN 12616001077459, Aug. 10, 2016, web.

Australian New Zealand Clinical Trials Registry (ANZCTR), "First-in-Human, Single Ascending Oral Dose Study of DV-928 inHealthy Volunteers", Trial ID ACTRN 12614001022651, Sep. 24, 2014, web.

Axelson and Larsson, "27-Hydroxylated Low Density Lipoprotein (LDL) Cholesterol Can Be Converted to 7[alpha],27-3 Dihydroxy-4-cholesten-3-one (Cytosterone) before Suppressing Cholesterol Production in Normal Human Fibroblasts", The Journal of Biological Chemistry, May 31, 1996, pp. 12724-12736, vol. 271, No. 22, The American Society for D Biochemistry and Molecular Biology, Inc.

(56) References Cited

OTHER PUBLICATIONS

Babaev et al., "Macrophage expression of peroxisome proliferator-activated receptor-alpha reduces atherosclerosis in low-density lipoprotein receptor-deficient mice", Circulation, 2007, pp. 1404-1412, vol. 116.

Bai et al., "Oxysterol sulfation by cytosolic sulfotransferase suppresses liver X receptor/sterol regulatory element binding protein-1c signaling pathway and reduces serum and hepatic lipids in mouse models of nonalcoholic fatty liver disease", Metabolism, 2012, pp. 836-845, vol. 61, Elsevier.

Bai Q, et al., "Sulfation of 25-hydroxycholesterol by SULT2B1b decreases cellular lipids via the LXR/SREBP-1c signaling pathway in human aortic endothelial cells"; Atherosclerosis. Feb. 2011; 214(2): 350-356.

Bai, et al "Overexpression of Oxysterol Sulfotransferase (Sult2B1 b) Decreases Intracellular Lipid Levels via SREBPs Signaling Pathway in Primary Human Aorta Endothelial Cells"; Abstract, Arteriosclerosis, Thrombosis, and Vascular Biology 2010 Scientific Sessions, American Heart Association; Apr. 8-10, 2010.

Beaven SW, et al.; "Reciprocal Regulation of Hepatic and Adipose Lipogenesis by Liver X Receptors in Obesity and Insulin Resistance"; Cell Metabolism. 2013; 18, 106-117.

Beltowski, "Liver X Receptors (LXR) as Therapeutic Targets in Dyslipidemia", Cardiovascular Therapy, 2008, pp. 279-316, vol. 26.

Bjoerkem, "Are side-chain oxidized oxy sterols regulators also in vivo?", The Journal of Lipid Research, Apr. 2009, pp. S213-S218, vol. 50, American Society for Biochemistry and Molecular Biology, Inc.

Blaton, "Dyslipidemia at chronic renal failure," International Federation of Clinical Chemistry and Laboratory Medicine, 2009, vol. 20, No. 1, pp. 59-60 Ejifcc 20/01 http://www.ifcc.org.

Bocher V, et al., "Liver X Receptors: New Players in Atherogenesis?"; Current Opinion in Lipidology. 2003; 14(2): 137-143.

Carey MC et al., "Solution properties of sulfated monohydroxy bile salts. Relative insolubility of the disodium salt of glycolithocholate sulfate"; Biochim.Biophys Acta 575:16-26, 1979.

Cases et al., "Dyslipidemia and the progression of renal disease in chronic renal failure patients," Kidney International, 2005, vol. 68, supplement 99, pp. s87-s93.

Cerpnjak K, et al (2013) "Lipid-based systems as a promising approach for enhancing the bioavailability of poorly water-soluble drugs"; Acta Pharm. 63(4); pp. 427-445.

Cha and Kim "Sulfated oxysterol 25HC3S as a therapeutic target of non-alcoholic fatty liver disease", Metabolism, 2012, pp. 1055-1057, vol. 61, Elsevier.

Cha and Repa "The liver X receptor (LXR) and hepatic lipogenesis. The carbohydrate-response element-binding protein is a target gene of LXR", Journal of Biological Chemistry, Jan. 5, 2007, pp. 743-751, vol. 282, No. 1.

Chang RK, et al. (2013) "Generic development of topical dermatologic products: formulation development, process development, and testing of topical dermatologic products"; AAPS J. 15(1); pp. 41-52.

Chapman E. et al., "Sulfotransferases: Structure, mechanism, biological activity, inhibition, and synthetic utility"; Angew.Chem. Int. Ed Engl 43:3526-3548, 2004.

Chen et al. "Influenza A virus infection activities cholesterol sulfotransferase (SUL T2B1 b) in the lung of female C57BU6 mice". Biol. Chem., Oct. 2011, pp. 869-876, vol. 392.

Chen et al., "Enzymatic Reduction of Oxysterols Impairs LXR Signaling in Cultured Cells and the Livers of Mice", Cell Metab., Jan. 2007, pp. 73-79, vol. 5, No. 1, Elsevier.

Considine et al., "Serum immunoreactive-leptin concentration in normal-weight and obese humans," The New England Journal of Medicine, 1996, vol. 334, No. 5, pp. 292-295.

Cook et al. (2009) "24-Hydroxycholesterol Sulfation by Human Sytosolic Sulfotransferases: Formation of Monosulfates and Disulfates, Molecular Modeling, Sulfatase Sensitivity, and Inhibition of Liver X Receptor Activation", Drug Metabolism and Disposition, vol. 37, No. 10; pp. 2069-2078, The American Society for Pharmacology and Experimental Therapeutics.

Corsini et al. "Effects of 26-Aminocholesterol. 27-Hydroxycholesterol, and 25-Hydroxycholesterol on Proliferation and Cholesterol Homeostasis in Arterial Myocytes", Arteriosclerosis, Thrombosis, and Vascular Biology, 1995, pp. 420-428, vol. 15, American Heart Association.

DePass, et al; "A 14-Day Intravenous Infusion Toxicity and Toxicokinetic Study of DUR-928, a Novel, First in Class, Investigational Therapeutic in Sprague-Dawley Rats"; American College of Toxicology's 39th Annual Meeting, West Palm Beach, Florida, Nov. 4-7, 2018.

DePass, et al; "In Vivo Tissue Distribution and Elimination of DUR-928, a First in Class Therapeutic for Treatment of Hepatic and Renal Disease"; Abstract #3355/Poster Board #P137, Late Breaking SOT Poster, Toxicokinetics, 57thAnnual Meeting of the Society of Toxicology, San Antonio, Texas, Mar. 11-15, 2018.

Diczfalusy U. "On the Formation and Possible Biological Role of 25-hydroxycholesterol"; Biochimie. 2013; 95 (3):455-460.

Ducheix S, et al., "The Liver X Receptor: A Master Regulator of the Gut-Liver Axis and a Target for Non Alcoholic Fatty Liver Disease"; Biochemical Pharmacology. 2013; 86(1): 96-105.

Durect (2018) "A Research Study to Evaluate Safety and Efficacy of DUR-928 in Subjects With Primary Sclerosing Cholangitis (PSC)"; U.S. National Library of Medicine, ClinicalTrials.gov Identifier: NCT03394781; 13 pages.

Durect, (2018) "A Research Study to Assess the Safety, Pharmacokinetics and Pharmacodynamics of DUR-928 in Patients With Alcoholic Hepatitis (AH)"; U.S. National Library of Medicine, ClinicalTrials.gov Identifier: NCT03432260; 14 pages.

Duvnjak et al., "Pathogenesis and management issues for non-alcoholic fatty liver disease"; World journal of gastroenterology, 13(34). pp. 4539-4550. 2007.

Englund et al., "25-hydroxycholesterol induces lipopolysaccharide-lolerance and decreases a lipopolysaccharide-induced TNF-[gamma] secretion inmacrophages", Atherosclerosis, 2001, pp. 61-71, vol. 158, Elsevier.

Falany CN., Sulfation and sulfotransferases. Introduction: changing view of sulfation and the cytosolic sulfotranferases, FASEB J. 11 1-2, 1997.

Feng et al., "The role of leptin in obesity and the potential for leptin replacement therapy" Endocrine, 2013, vol. 44, pp. 33-39 (Year: 2013).

Fuda et al., "Mutational Analysis of Human Hydroxysteroid Sulfotransferase SUL T2B1 Isoforms Reveals That Exon 1B of the SULT2B1 Gene Produces Cholesterol Sulfotransferase, whereas Exon 1A Yields Pregnenolone Sulfotransferase", The Journal of Biological Chemistry, Sep. 27, 2002, pp. 36161-36166, vol. 277, No. 39, American Society for Biochemistry and Molecular Biology, Inc.

Fuda et al., "Oxysterols are substrates for cholesterol sulfotransferase", The Journal of Lipid Research, Mar. 2007, pp. 1343-1352, vol. 48, American Society for Biochemistry and Molecular Biology, Inc.

Geese and Raftogianis, "Biochemical Characterization and Tissue Distribution of Human SULT2B1", Biochemical and Biophysical Research Communications, 2001, pp. 280-289, vol. 288, Academic Press.

Gill et al., "Sterol regulators of cholesterol homeostasis and beyond: The oxysterol hypothesis revisited and revised", Progress in Lipid Research, 2008, pp. 391-404, vol. 47, Elsevier.

Grefhorst et al., "Stimulation of Lipogenesis by Pharmacological Activation of the Liver X Receptor Leads to Production of Large, Triglyceride-rich Very Low Density Lipoprotein Particles", Lipids and Lipoproteins, Sep. 13, 2002, pp. 34182-34190, vol. 277, No. 37.

Griffett K, et al, "A Liver-Selective LXR Inverse Agonist that Suppresses Hepatic Steatosis"; ACS Chemical Biology. 2013; 8(3):559-567.

Gross et al., Quality of Life Before and After Liver Transplantation for Cholestatic Liver Disease. Hepatology 1999;29:356-364 (Year: 1999).

Hassanein, et al (2019) "Safety and Efficacy of DUR-928: A Potential New Therapy for Acute Alcoholic Hepatitis" AASLD; Abstract LB-09 (Durect C928-010 Trail); 1 page.

(56) References Cited

OTHER PUBLICATIONS

Hassanein, et al (2019) "Safety and Efficacy of DUR-928: A Potential New Therapy for Acute Alcoholic Hepatitis"; AASLD; 22 pages.

He D., et al, "Inhibition of SULT2B1B expression alters effects of 3 beta-hydroxysteroids on cell proliferation and steroid hormone receptor in human LNCaP prostate cancer cells"; Prostate 67-1318-1329, 2007.

He et al., "Identification and immunohistochemical localization of Sulfotransferase 2B1b (SULT2B1b) in human lung", Biochimica et Biophysica Acta, Apr. 12, 2005, pp. 119-126, vol. 1724, Elsevier.

Higashi et al., "Expression of Cholesterol Sulfotransferase (SULT2B1b) in Human Skin and Primary Cultures of Human Epidermal Keralinocytes", The Journal of Investigative Dermatology, 2004, pp. 1207-1212, vol. 122, The Society for Investigative Dermatology.

Horton J, et al "SREBPs: activators of the complete program of cholesterol and fatty acid synthesis in the liver"; The Journal of Clinical Investigation. 2002; 109(9):1125-1131.

Horton J, et al. "Combined analysis of oligonucleotide microarray data from transgenic and knockout mice identifies direct SREBP target genes"; PNAS. 2003; 100(21): 12027-12032.

Ikegami et al., "Increased serum liver X receptor ligand oxysterols in patients with non-alcoholic fatty liver disease", J Gastroenterol, May 9, 2010, pp. 1257-1266, vol. 47, Springer.

Itoh, et al (1999) "Synthesis of 6- and 7-hydroxyestradiol 17-sulfates: The potential metabolites of estradiol 17-sulfate by female rat liver microsomes"; Steroids 64; pp. 363-370.

Janout et al., "An Upside Down View of Cholesterol's Condensing Effect: Does Surface Occupancy Play a Role?", Langmuir, Apr. 20, 2010, pp. 5316-5318, vol. 26, No. 8.

Janowski et al., "An oxysterol signalling pathway mediated by the nuclear receptor LXR alpha"; Letters to Nature, Oct. 24, 1996, pp. 728-731, vol. 383.

Janowski et al., "Structural requirements of ligands for the oxysterol liver X receptors LXRα and LXRβ", Proc Natl Acad Sci U S A. Jan. 5, 1999;96(1):266-71.

Javitt et al., "Cholesterol and hydroxycholesterol sulfotransferases: Identification, distinction from dehydroepiandrosterone sulfotransferase, and differential tissue expression". Endocrinology, vol. 142, pp. 2978-2984, 2001.

Ji et al., "Human Hydroxysteroid Sulfotransferase SULT2B1 Pharmacogenomics: Gene Sequence Variation and Functional Genomics", The Journal of Pharmacology and Experimental Therapeutics, 2007, pp. 529-540, vol. 322, No. 2, The American Society for Pharmacology and Experimental Therapeutics.

Jones et al., Hepatocellular Carcinoma in Primary Biliary Cirrhosis and its impact on outcomes. Hepatology, 1997, 26:1138-1142 (Year:1997).

Kanjanabuch T, et al (2007) "PPAR-γ agonist protects podocytes from injury"; Kidney Int. 71(12); pp. 1232-1239.

Kasakabe, Toru, et al (2010) "Congenital deficiency of leptin and its receptor in humans"; Japanese Journal of Clinical Medicine, vol. 68, extra issue 2, p. 486-490.

Kase et al., "Liver X receptor antagonist reduces lipid formation and increases glucose metabolism in myotubes from lean, obese and type 2 diabetic individuals", Diabetologia, 2007, pp. 2171-2180, vol. 50, Springer-Verlag.

Kawata et al.,"Effect of pravastatin on survival in patients with advanced hepatocellular carcinoma. A randomized controlled trial"; British Journal of Cancer (2001) 84(7), 886-891 (Year:2001).

Kay and Fausto, Liver regeneration: prospects for therapy based on new technologies; Molecular Medicine Today, Mar. 1997, pp. 108-115.

Kemp, W., "Safety and pharmacokinetics of DUR-928 in patients with non-alcoholic steatohepatitis—A Phase 1b study", Apr. 2017.

Khan and Glenton (2008) "Calcium oxalate crystal deposition in kidneys of hypercalciuric mice with dismpted type IIa sodium-phosphate cotransporter"; Am J Physiol Renal Physiol. 294(5):F1109-15.

Kim MJ, et al; "Attenuation of Renal Ischemic Reperfusion Injury in Rats with DUR-928, a Novel, First-in-Class Therapeutic in Development for Renal Disease"; Poster #: SA-PO650, Kidney Week, San Diego, CA—Oct. 23-28, 2018.

Kim, Mee J., "DUR-928, an endogenous regulatory molecule, exhibits anti-inflammatory and antifibrotic activity in a mouse model of NASH", Mar. 2017.

Landis et al., "Oxysterol Activators of Liver X Receptor and 9-cis-Retinoic Acid Promote Sequential Steps in the Synthesis and Secretion of Tumor Necrosis Factor-alpha from Human Monocytes", Journal of Biological Chemistry, Feb. 15, 2002, pp. 4713-4721, vol. 277, No. 7.

Lappano et al., "The Cholesterol Metabolite 25-Hydroxycholesterol Activates Estrogen Receptor a-Mediated Signaling in Cancer Cells and in Cardiomyocytes", PloS ONE, Jan. 31, 2011, pp. e16631-e16631, vol. 6, No. 1.

Lee YC. et al., "Sp1 elements in SULT2B1b promoter and 5'-untranslated region of mRNA: Sp1/Sp2 induction and augmentation by histone deacetylase inhibition"; FEBS Lett. 579:3639-3645, 2005.

Lehmann et al., "Activation of the Nuclear Receptor LXR by Oxysterols Defines a New Hormone Response Pathway", The Journal of Biological Chemistry, Feb. 7, 1997, pp. 3137-3140, vol. 272, No. 6.

Li et al. (1999) "Sterol synthesis. Preparation and characterization of fluorinated and deuterated analogs of oxygenated derivatives of cholesterol"; Chemistry and Physics of Lipids 99; pp. 33-71.

Li et al., "Biosynthesis of the regulatory oxysterol, 5-cholesten-3β,25-diol 3-sulfate, in hepatocytes", Journal of Lipid Research, Sep. 21, 2007, pp. 2587-2596, vol. 48.

Li et al., "Enzyme activity assay for cholesterol 27-hydroxylase in mitochondria", Journal of Lipid Research, Apr. 12, 2006, pp. 1507-1412, vol. 47.

Lindsay, J; et al., (2008) "Structure, function and polymorphism of human cytosolic sulfotransferases"; Curr.Drug Metab 9:99-105.

Liu et al., "Nuclear Transport Modulation Reduces Hypercholesterolemia, Atherosclerosis, and Fatty Liver", Journal of The American Heart Association, Apr. 5, 2013, American Heart Association, Dallas, TX.

Lo Sasso et al., "Down-Regulation of the LXR Transcriptome Provides the Requisite Cholesterol Levels to Proliferating Hepatocytes", Hepatology, 2010, pp. 1334-1344, vol. 51.

Lo Sasso G, et al. (2010) Intestinal Specific LXR Activation Stimulates Reverse Cholesterol Transport and Protects from Atherosclerosis. Cell metabolism. 2010; 12(2), 187-193.

Lopez-Velazquez JA, et al., "Nuclear Receptors in Nonalcoholic Fatty Liver Disease"; Journal of Lipids. 2012.; 2012, Article ID 139875.

Lund EG. et al., "cDNA cloning of mouse and human cholesterol 25-hydroxylases, polytopic membrane proteins that synthesize a potent oxysterol regulator of lipid metabolism". J. Bio. Chem. 273:34316-34327, 1998.

Ma et al., "25-Hydroxycholesterol-3-sulfate regulates macrophage lipid metabolism via the LXR/SREBP-1 signaling pathway", Am J Physiol Endocrinol Metab, Oct. 14, 2008, pp. E1369-E1379, vol. 295.

Markus et al., "Efficacy of Liver Transplantation in Patients with Primary Biliary Cirrhosis". N Engl J Med 1989; 320:1709-1713.

McClain, Craig J., "Which Therapeutic Targets Will Be the Most Attractive in the Future?", Oct. 2017.

McClain, et al (2019) "DUR-928 Therapy for Acute Alcoholic Hepatitis: A Pilot Study"; AASLD; Poster (Durect Corporation); 1 page.

McCormack and Gregoriadis (1994) "Drugs-in-cyclodextrins-in liposomes:a novel concept in drug delivery"; International Journal of Pharmaceutics 112; pp. 249-258.

McDonald and Russel, "25-Hydroxycholesterol: a new life in immunology", Journal of Leukocyte Biology, Dec. 2010, pp. 1071-1072, vol. 88, Society for Leukocyte Biology.

Meloche and Falany, "Expression and characterization of the human 3 [beta]-hydroxysteroid sulfotransferases (SULT2B1a and SUL T2B1b)", Journal of Steroid Biochemistry & Molecular Biology, 2001, pp. 261-269, vol. 77, Elsevier.

(56) References Cited

OTHER PUBLICATIONS

Millatt et al., "Liver X receptors and the control of cholesterol homeostasis: potential therapeutic targets for the treatment of atherosclerosis", Biochimica Et Biophysica Actia, 2003, pp. 107-118, No. 1631.

Monsalve, et al. Peroxisome Proliferator-Activated Receptor Targets for the Treatment of Metabolic Diseases; Mediators of Inflammation. 2013.

Napodano, Jason et al., Zacks Small-Cap Research, Mar. 4, 2015, pp. (1-14).

Nelson et al., "The Oxysterol, 27-Hydroxycholesterol, Links Cholesterol Metabolism to Bone Homeostasis Through Its Actions on the Estrogen and Liver X Receptors", Endocrinology, Sep. 20, 2011, pp. 1-15, vol. 152, No. 12, The Endocrine Society.

Ning, Yanxia, "Cholesterol metabolites alleviate injured liver function and decrease mortality in an LPS-induced mouse model", Metabolism Clinical and Experimental, 71 (2017), 83-93.

Ogawa et al., "A facile synthesis of C-24 and C-25 oxysterols by in situ generated ethyl(trifluoromethyl)dioxirane", Steroids, 2009, pp. 81-87, vol. 74, Elsevier.

Okamura et al., "Studies on Vitamin D (Calciferol) and Its Analogues. 13. 3-Deoxy-3α-methyl-1α-hydroxyvitamin $D_3$, 3-Deoxy-3α-methyl-1α,25-dihydroxyvitamin $D_3$, and 1α-Hydroxy-3-epivitamin $D_3$. Analogues with Conformationally Biased A Rings", Journal of Organic Chemistry, 1978, pp. 574-580, vol. 43, No. 4, American Chemical Society.

Okamura et al., "Studies on vitamin D and its analogs. VIII. 3-deoxy-1α,25-dihydroxyvitamin $D_3$, a potent new analog of 1α,25-(OH)2-$D_3$", Biochemical and Biophysical Research Communications, 1975, pp. 24-30, vol. 65, No. 1, Academic Press, Inc.

Pandak, et al., "Regulation of Oxysterol 7α-Hydroxylase (CYP7B1) in Primary Cultures of Rat Hepatocytes", Hepatology, 2002, pp. 1400-1408, vol. 35, No. 6, American Association for the Study of Liver Diseases.

Pandak, et al., "Reversal of NAFLD through selective increased intracellular hepatic cholesterol catabolism"; Poster Abstract, XXIII International Bile Acid Meeting: Bile Acids as Signal Integrators and Metabolic Modulators, Falk Symposium 194; Oct. 8-9, 2014.

Pandak, et al., "The cholesterol metabolite, 5-cholesten-3beta, 25-diol 3-sulfate, promotes hepatic proliferation in mice"; Poster Abstract, XXII International Bile Acid Meeting: Hepatic and Extrahepatic Targets of Bile Acid Signalling, Falk Symposium 184; Sep. 14-15, 2012.

Pandak, et al., "Transport of Cholesterol into Mitochondria Is Rate-limiting for Bile Acid Synthesis via the Alternative Pathway in Primary Rat Hepatocytes", The Journal of Biological Chemistry, Oct. 3, 2002, pp. 48158-48164, vol. 277, No. 50.

Peet et al., "Cholesterol and Bile Acid Metabolism Are Impaired in Mice Lacking the Nuclear Oxysterol Receptor LXRα", Cell, May 29, 1998, pp. 693-704, vol. 93, Cell Press.

Peet et al., "The LXRs: a new class of oxysterol receptors", Current Opinions in Genetics and Development, 1998, pp. 571-575, vol. 8.

Perez et al., "Bile-acid-induced cell injury and protection"; World J Gastroenterol Apr. 14, 2009; 15(14): 1677-1689 (Year: 2009).

Pezacki et al. "Transcriptional profiling of the effects of 25-hydroxycholesterol on human hepatocyte metabolism and the antiviral state ii conveys against the hepatitis C virus", BMC Chemical Biology, Jan. 16, 2009, vol. 9, No. 2, BioMed Central Lid.

Picard et al. (2012) "Mitochondrial dysfunction and lipid accumulation in the human diaphragm during mechanical ventilation"; Am J Resp Critical Care Med 186:1140.

Polyzos, et al. "Sulfated oxysterols as candidates for the treatment of nonalcoholic fatty liver disease"; Metabolism, 2012, pp. 755-758, vol. 61, Elsevier.

Quintero P. and Arrese M. (2013) "Nuclear Control of Inflammation and Fibrosis in Nonalcoholic Steatohepatitis: Therapeutic Potential of Dual Peroxisome Proliferator—Activated Receptor Alpha/Delta Agonism"; Hepatology 58(6), pp. 1881-1884.

Reboldi A. et al., "Inflammation 25-Hydraxycholesterol suppresses interleukin-1-driven inflammation downstream of type I interferon"; Science 345:679-684, 2014.

Reel B., et al (2013) "The effects of PPAR-γ agonist pioglitazone on renal ischemia/reperfusion injury in rats"; J Surg Res. 182(1); pp. 176-184.

Ren and Ning, "Sulfation of 25-hydroxycholesterol regulates lipid metabolism, inflammatory responses, and cell proliferation", Am J Physiol Endocrinol Metab, Dec. 3, 2013, pp. E123-E130, vol. 306.

Ren et al. "Identification of a novel sulfonated oxysterol, 5-cholesten-3β,25-diol 3-sulfonate, in hepatocyte nuclei and mitochondria"; Journal of Lipid Research, Feb. 27, 2006, pp. 1081-1090, vol. 47, American Society for Biochemistry and Molecular Biology, Inc.

Ren et al., "25-hydroxycholesterol and 25-hydroxycholesterol 3-sulfate reciprocally regulate lipid metabolism and inflammation in hepatocytes and macrophages", Abstract, The Liver Meeting, the 60th Annual Meeting of the American Association for the Study of Liver Diseases, Oct. 30-Nov. 3, 2009.

Ren et al., "25-Hydroxycholesterol-3-sulfate (25HC3S) regulates lipid metabolism by activation/inactivation of receptors in hepatocytes and macrophages", Abstract, XX International Bile Acid Meeting, Falk Symposium 165; Jun. 13-14, 2008.

Ren et al., "Discovery of a Novel Oxysterol, 5-Cholesten-3beta, 25-Diol 3-Sulfonate, in Nuclei and Mitochondria Following Overexpression of the Gene Encoding StarD1 ", Bile Acids: Biological Actions and Clinical Relevance, 2007 pp. 20-235, Kluwer Academic Publishers.

Ren et al., "Discovery of a Novel Oxysterol, 5-Cholesten-3beta, 25-Diol 3-Sulfonate, in Nuclei and Mitochondria Following Overexpression of the Gene Encoding StarD1", Abstract, International Bile Acid Meeting, XIII Falk Liver Week, Falk Symposia 155, Oct. 6-11, 2006.

Ren et al., "Discovery of a Novel Regulatory Pathway for Maintenance of Intracellular Cholesterol Homeostasis", Abstract, DOW Annual Meeting 2007, May 19-25, 2007.

Ren et al., "Identification of a Novel Regulatory Nuclear Oxysterol", Abstract, 56rd Annual Meeting of the American Association for the Study of Liver Diseased, Nov. 11-15, 2005.

Ren et al., "Identification of Novel Regulatory Cholesterol Metabolite, 5-Cholesten, 3β,25-Diol, Disulfate" PLOS ONE, Jul. 2014, vol. 9. No. 7, p. 1-11.

Ren et al., "Overexpression of Cholesterol Transporter StAR Increases In Vivo Rates of Bile Acid Synthesis in the Rat and Mouse"; Liver Biology and Pathobiology, Aug. 20, 2004, pp. 910-917, vol. 40, No. 4.

Ren et al., "Regulation of Hepatocyte Lipid Metabolism by 25-Hydroxycholesterol-3-Sulfate (25HC3S) Is Mediated via the LXR/SREBP-1 Signaling Pathway"; Abstract, DOW Annual Meeting 2008, May 17-23, 2008.

Ren S., et al., "Sulfated oxsterol, 25HC3S, is a potent regulator of lipid metabolism in human hepatocytes", ScienceDirect, BBRC, 360 (2007) pp. 802-808.

Ren S., et al; "The acidic pathway of bile acid biosynthesis: Role in oxy sterol sulfation, lipid metabolism and inflammatory responses"; Poster Abstract, XXII International Bile Acid Meeting, Falk Symposia 184; Sep. 14-15, 2012.

Ren, et al "25-Hydroxycholesteroi-3-Sulfate Activates PPARgamma and Attenuates Inflammatory Responses in Human Macrophages"; Poster Abstract, Arteriosclerosis, Thrombosis, and Vascular Biology Annual Conference 2009, American Heart Association; Apr. 29-May 1, 2009.

Ren, et al; "Oxysterol sulfates alleviate injured liver function and decrease mortality in mouse models"; Poster Abstract, XXV International Bile Acid Meeting:Bile Acids in Health and Disease, Symposium 211; Jul. 6-7, 2018.

Ren, Shunlin, "Novel Oxysterol Sulfates Alleviate Injured Liver Function and Decrease Mortality in Mouse Models", Nov. 2017.

Ruan X, et al., "PPARs and the kidney in metabolic syndrome", AJP-Renal Physiol, vol. 294, Jan. 30, 2008.

Shah, et al; "A Clinical Drug-Drug Interaction Study with Midazolamto Assess the Effect of DUR-928 on CYP3A4"; Meeting of the American College of Clinical Pharmacology, Bethesda, Maryland, Sep. 23-25, 2018; 1 page.

(56) References Cited

OTHER PUBLICATIONS

Shah, et al; "Pharmacokinetic and Pharmacodynamic Response in Individual NASH Patients Receiving Two Dose Levels of DUR-928"; NASH Summit—2019, Apr. 22-25, 2019. 1 page.
Shah, et al; "Safety and Single Ascending Dose Pharmacokinetic Study of DUR-928 in Patients with Chronic Kidney Disease versus Matched Control Subjects"; Poster #: SA-PO63; Kidney Week, San Diego, CA—Oct. 23-28, 2018; 1 page.
Shepherd et al., "Effective of intensive lipid lowering with atorvastatin on renal function in patients with coronary heart disease: the treatment of new targets study," Clin. J. Am. Soc. Nephrol. vol. 2, pp. 1131-1139.
Shi et al., "Cholesterol Sulfate and Cholesterol Sulfotransferase Inhibit Gluconeogenesis by Targeting Hepatocyte Nuclear Factor 4α", Molecular and Cellular Biology, Feb. 1, 2014, vol. 34, No. 3, p. 485-497.
Shimizu et al., "Conservation of the Hydroxysteroid Sulfotransferase SULT2B1 Gene Structure in the Mouse: Pre- and Postnatal Expression, Kinetic Analysis of Isoforms, and Comparison with Prototypical SULT2A1"; Endocrinology, Apr. 2003, pp. 1186-1193, vol. 144, No. 4, The Endocrine Society.
Sivarajah A., et al (2003) "Agonists of peroxisome-proliferator activated receptor-gamma reduce renal ischemia/reperfusion injury"; Am J Nephrol. 23(4); 267-276.
Song et al. "Auto-oxidized cholesterol sulfates are antagonistic ligands of liver X receptors: implications for the development and treatment of atherosclerosis". Steroids. 2001. pp. 473-479, vol. 66, Elsevier.
Strott and Higashi, "Cholesterol sulfate in human physiology: what's it all about?", Journal of Lipid Research, 2003, pp. 1268-1278, vol. 44.
Taddei et al., "High incidence of cholesterol gallstone disease in type 1 Gaucher disease: characterizing the biliary phenotype of type 1 Gaucher disease," J. Inherit Metab Dis. 2010, vol. 33, pp. 291-300).
Tan et al., "Leptin Deficiency contributes to the pathogenesis of alcoholic fatty liver disease in mice", The American Journal of Pathology, 2012, vol. 181, No. 10, pp. 1279-1286 (Year: 2012).
Teh, et al., "Hepatic Resection of Hepatocellular Carcinoma in Patients with Cirrhosis: Model of End-Stage Liver Disease (MELD) Score Predicts Perioperative Mortality"; Journal of Gastrointestinal Surgery, vol. 9, No. 9, 200-5, pp. 1207-1215 (Year:2005).
Thakar et al., "Acute kidney injury episodes and chronic kidney disease risk in diabetes mellitus"; Clin. J. Am. Soc. Nephrol. 2011, vol. 6, pp. 2567-2572. (Year: 2011).
Therapeutics, Inc. (2019) "Safety and Efficacy Study of DUR-928 Topical Solution in Subjects With Plaque Psoriasis"; U.S. National Library of Medicine, ClinicalTrials.gov Identifier: NCT03837743; 14 pages.
Treuter, "New wrestling rules of anti-inflammatory transrepression by oxysterol receptor LXR revealed", Cell Research, 2011, pp. 711-714, vol. 21.
Trousson et al., "25-hydroxycholesterol provokes oligodendrocyte cell line apoptosis and stimulates the secreted phospholipase A2 type IIA via LXR beta and PXR"; Journal of Neurochemistry, 2009, pp. 945-958, vol. 109.
Wagner BL, et al. "Promoter-Specific Roles for Liver X Receptor/Corepressor Complexes in the Regulation of ABCA1 and SREBP-1 Gene Expression"; Mal. Cell. Biol. 2003; 23(16):5780.
Wang, et al (2020) "High Glucose Induces Lipid Accumulation via 25-Hydroxycholesterol DNA-CpG Methylation"; iScience 23(5); pp. 1-28.
Weinberg (2006) "Lipotoxicity"; Kidney International 70:1560.
Williams et al., "Effects of cholesterol sulfate on lipid metabolism in cultured human keratinocytes and fibroblasts"; Journal of Lipid Research, vol. 28, pp. 955-967, 1987.
Wojcicka et al., "Liver X receptors (LXRs). Part I: Structure, function, regulation of activity, and role in lipid metabolism", Postepy Hig Med Dosw., Dec. 3, 2007, pp. 736-759, vol. 61.

Xu et al. "Reversal of Diet-induced Serum and Hepatic Lipid Accumulation by 5-cholesten-3beta.25-diol 3-sulfate in Mouse Models of Nonalcoholic Fatty Liver Diseases"; Hepatology, Jun. 9, 2011.
Xu et al., "25-Hydroxycholesterol (25HC) and 25HC-3-Sulfate (25HC3S) Mediate Nuclear Orphan Receptors in Opposite Direction in Hepatocytes", Abstract, XX International Bile Acid Meeting, Falk Symposia 165, Jun. 13-14, 2008.
Xu et al., "25-Hydroxycholesterol-3-sulfate (25HC3S) Attenuates Hepatocyte Intracellular Lipid Levels and Inflammatory Response via LXR/SREBPs and IKBa/NF-KB Pathways", Abstract, DOW Annual Meeting 2008, May 3, 2010.
Xu et al., "25-Hydroxycholesterol-3-Sulfate (25HC3S) Suppresses NF-kB Activatioand Inflammatory Response in Human Macrophages and Hepatocytes", Abstract, Arteriosclerosis, Thrombosis, and Vascular Biology 2010 Scientific Sessions, American Heart Association; Apr. 8-10, 2010.
Xu et al., "25-Hydroxycholesterol-3-sulfate attenuates inflammatory response via PPAR [gamma] signaling in human THP-1 macrophages", Am J Physiol Endocrinol Metab, Jan. 24, 2012, pp. E788-E799, vol. 302.
Xu et al., "25-Hydroxycholesterol-3-Sulfate Decreases Hepatic Steatosis and Inflammation In Mouse Models of Nonalcoholic Fatty Liver Disease by Down-Regulating Sterol Regulatory Element Binding Protein-1c", Abstract, DOW Annual Meeting 2011, May 7-10, 2011.
Xu et al., "5-Cholesten-3β,25-Diol 3-Sulfate Decreases Lipid Accumulation in Diet-Induced Nonalcoholic Fatty Liver Disease Mouse Model", Molecular Pharmacology, Mar. 2013, 648-658, vol. 83.
Xu et al., "Induction of IκBα Expression as a Mechanism Contributing to the Anti-inflammatory Activities of Peroxisome Proliferator-activated Receptor-α Activators", Abstract, DOW Annual Meeting 2011, May 7-10, 2011.
Xu et al., "Induction of IKBα Expression Mediates the Anti-Inflammatory Response to 25-Hydroxycholesterol-3-Sulfate (25HC3S) in Primary Rat Hepatocytes and THP-1 Macrophages"; AASLD Abstract; 2011.
Xu et al., "Regulation of Hepatocyte Lipid Metabolism and inflammatory Response by 25-Hydroxycholesterol and 25-Hydroxycholesterol-3-sulfate", Lipids, 2010, pp. 821-832, vol. 45, AOCS.
Zager et al. (2011) "Acute unilateral ischemic renal injury induces progressive renal inflammation, lipid accumulation, histone modification, and "end-stage" kidney disease."; Am J Physiol Renal Physiol 30:F1334.
Zelcer N and Tontonoz P. "Liver X receptors as integrators of metabolic and inflammatory signaling"; J Clin Invest. 2006; 116(3):607-614.
Zhang et al., "Cholesterol metabolite, 5-cholesten-3β-25-diol-3-sulfate, promotes hepatic proliferation in mice"; Journal of Steroid Biochemistry and Molecular Biology, 2012, pp. 262-270, vol. 132, Elsevier.
Zhang et al., "Cytosolic sulfotransferase 2B1b promotes hepatocyte proliferation gene expression in vivo and in vitro", Am J Physiol Gastrointest Liver Physiol, Jun. 7, 2012, pp. G344-G355, vol. 303.
Zhang et al., "Effects of 25-hydroxycholesterol sulfation on liver regeneration in normal and partial hepatectomy (PHX) mouse models", Abstract, DOW Annual Meeting 2011, May 7-10, 2011.
Zhang et al., "Effects of 25-Hydroxycholesterol Sulfation on Liver Regeneration in Normal and Partial Hepatectomy (PHX) Mouse Models"; May 2011, Gastroenterology vol. 140, Issue 5, Supplement 1, p. S-967.
Zhang Hengai et al., "Advances in the research on drugs for the prevention and treatment of renal diseases with PPAR as target site", China Pharmaceutical Journal, vol. 45, No. 7, Apr. 30, 2010.
Zitvogel et al. (2010) "Decoding cell death signals in inflammation and immunity"; Cell 140(6); pp. 798-804.
Zuercher et al., "Discovery of Tertiary Sulfonamides as Potent Liver X Receptor Antagonists", J. Med. Chem., 2010, pp. 3412-3416, vol. 53, No. 8, American Chemical Society.
Zuo, et al (2012) "Protective effects of PPARγ agonist in acute nephrotic syndrome"; Nephrol Dial Transplant. 27(1); pp. 174-181.

(56) References Cited

OTHER PUBLICATIONS

ASBMB Today (2021) "A mechanism of liver disease treatment" *The Member Magazine of the American Society for Biochemistry and Molecular Biology*, 1 page.
ClinicalTrials.gov: NCT04563026; "A Phase 2b Study in Subjects With Alcoholic Hepatitis to Evaluate Safety and Efficacy of DUR-928 Treatment (AHFIRM)"; Study Details; Durect Corporation; Sep. 24, 2020; 8 pages.
ClinicalTrials.gov: NCT04563026; "A Phase 2b Study in Subjects With Alcoholic Hepatitis to Evaluate Safety and Efficacy of DUR-928 Treatment (AHFIRM)"; Tabular View; Durect Corporation; Sep. 24, 2020; 8 pages.
Craig, et al (2010) "Systematic review: prognostic tests of paracetamol-induced acute liver failure"; Aliment Pharmacol Ther 31(10); pp. 1064-1076.
Dao and Rangnekar (2018) "Steroids for Severe Alcoholic Hepatitis: More Risk Than Reward?"; Clin Liver Dis (Hoboken) 12(6); pp. 151-153.
Durect (2015) "Durect Announces Epigenomic Regulator Program including a New NAFLD/NASH and Acute Organ Injury Product Candidate in Development"; News Release, Mar. 2, 2015; 4 pages.
Durect (2015) "Durect Announces Positive Results from DUR-928 Multi-Dose Phase 1 Study"; News Release, May 18, 2015; 4 pages.
Durect (2016) "Durect Announces Positive Phase 1 Data for DUR-928"; News Release, Jan. 6, 2016; 3 pages.
Durect (2016) "Durect Corporation Announces Update on DUR-928Development Program"; News Release, Oct. 31, 2016; 5 pages.
Durect (2017) "Durect Corporation Announces Update on DUR-928 Development Program"; News Release, Jan. 30, 2017; 4 pages.
Durect (2018) "Durect Announces Amendment to Accelerate Ongoing Phase 2a Trial of DUR-928 in Alcoholic Hepatitis (AH) by Allowing Dosing of Severe AH Patients in Parallel to Moderate AH Patients" News Release, Nov. 19, 2018; 4 pages.
Durect (2018) "Durect Announces Patient Dosing in Phase 2a Trial ofDUR-928 in Alcoholic Hepatitis"; News Release, Apr. 25, 2018; 3 pages.
Durect (2019) "Durect Announces Positive Data from its Phase 2a Clinical Trial ofDUR-928 in Alcoholic Hepatitis"; News Release, Sep. 17, 2019; 3 pages.
Durect (2019) "Durect Corporation Announces Preliminary Data from the Ongoing DUR-928 Alcoholic Hepatitis Phase 2a Trial"; News Release, May 7, 2019; 6 pages.
Durect (2020) "Durect Corporation Announces Positive Topline Data from Phase 1b Study of DUR-928 in NASH"; News Release, May 26, 2020; 6 pages.
Durect (2020) "Durect Corporation Announces Top-Line Results from Phase 2a Clinical Trial in Patients with Psoriasis"; News Release, Jan. 2, 2020; 3 pages.
English Translation of Japanese Office Action dated Jul. 23, 2019, for Japanese Patent Application No. 2017-518508.
Jambhekar and Breen (2016) "Cyclodextrins in pharmaceutical formulations II: solubilization, binding constant, and complexation efficiency"; Drug Disc Today, vol. 21, No. 2; pp. 363-368.
Jinjuvadia and Liangpunsakul (2015) "Trends in Alcoholic Hepatitis-related Hospitalizations, Financial Burden, and Mortality in the United States"; J Clin Gastroenterol, 49(6);pp. 506-511.
Lawitz et al., "Efficacy Signals of 4-Week Oral DUR-928 in NASH Subjects;" ePoster at EASL the International Liver Congress; Jun. 23, 2021.
Lawitz et al., "Safety and Efficacy Signals of Daily Oral DUR-928 for 4-Weeks in F1-F3 NASH;" ePoster at AASLD the Liver Meeting; Nov. 13, 2020.
Li et al., (2006) "A Novel Metabolic Pathway for the Synthesis of the Newly Discovered Nuclear 5-cholesten-3β,25-Diol3-sulphate", Abstract; 1 page.
Luu W. et al. (2016) "Oxysterols: Old Tale, New Twists"; Annu Rev Pharmacol Toxicol. 56: pp. 447-467.
Marlowe et al., Prevalence, Co-Morbidities and In-Hospital Mortality of Hospitalized Alcohol-Associated Hepatitis In US In 2015-2018. AASLD The Liver Meeting®; Nov. 12-15, 2021.
Ren, "Oxysterol Sulfation as Regulatory Signaling Pathway"; McGuire VA Medical Center Nirginia Commonwealth University; (Apr. 2014) 1 page.
Ren, "Sulfation of 25-Hydroxycholesterol Regulates Lipid Metabolism and Inflammatory Responses in Human Aortic Endothelial Cells, Macrophages, and Hepatocytes"; Abstract; Departments of Medicine, McGuire Veterans Affairs Medical CenterNirginia Commonwealth University; (Jan. 2014) 1 page.
Shah et al., "Pharmacokinetics of DUR-928 in Alcoholic Hepatitis Patients—A Phase 2a Study;" ePoster at EASL The European Association for the Study of the Liver; Aug. 27, 2020.
Shah et al., "Safety and Pharmacokinetics of DUR-928 in Hepatic Function Impaired Subjects," ePoster at EASL the International Liver Congress; Jun. 23, 2021.
Su et al., (2007) "Hypercholesterolemia in Primary Biliary Cirrhosis"; N Eng J Med 357; 15:1561-1562.
Wang and Ren "25-Hydroxycholesterol is a Potent Epigenetic Regulator: High Glucose Induces Lipid Accumulation via 25-Hydroxycholesterol DNA-CpG Methylation in Human Hepatocytes"; Department of Internal Medicine, Virginia Commonwealth University/McGuire VA Medical Centre; AASLD Annual Meeting, Nov. 13-16, 2020. 1 page.
Wang et al. (2021) "25-Hydroxycholesterol 3-sulfate is an endogenous ligand of DNA methyltransferases in hepatocytes"; Journal of Lipid Research. 2021; 62: 100063.
Wang, et al (2021) "25-Hydroxycholesterol 3-Sulfate Recovers Acetaminophen Induced Acute Liver Injury via Stabilizing Mitochondria in Mouse Models" Cells 10, 3027; pp. 1-17.
You, et al (2002) "Ethanol Induces Fatty Acid Synthesis Pathways by Activation of Sterol Regulatory Element-binding Protein (SREBP)"; The Journal of Biological Chemistry, vol. 277, No. 32; pp. 29342-29347.
Zhang et al., (2011) "SULT2B1b overexpression promotes liver regeneration via inhibiting LXR signaling pathway in mouse with or without Partial Hepatectomy", Poster; Departments of Medicine, Virginia Commonwealth University/McGuire Veterans Affairs Medical Center, Richmond, Virginia.; 1 page.

* cited by examiner

COMPOSITIONS COMPRISING 5-CHOLESTEN-3, 25-DIOL, 3-SULFATE (25HC3S) OR PHARMACEUTICALLY ACCEPTABLE SALT THEREOF AND AT LEAST ONE CYCLIC OLIGOSACCHARIDE

FIELD OF THE DISCLOSURE

The present disclosure generally relates to compositions comprising 5-cholesten-3,25-diol, 3-sulfate (25HC3S) or pharmaceutically acceptable salt thereof and at least one cyclic oligosaccharide, e.g., at least one cyclodextrin (CD) and/or derivative thereof. The compositions may be used to treat and/or prophylactically treat a wide variety of diseases and conditions, such as conditions that are caused by or related to inflammation.

INTRODUCTION 5-cholesten-3,25-diol, 3-sulfate (25HC3S) or pharmaceutically acceptable salt thereof is known to prevent and treat a wide variety of diseases and conditions. For instance, 25HC3S or pharmaceutically acceptable salt thereof is known to be a potent mediator of inflammation and successfully used to prevent and treat diseases caused by or exacerbated by inflammation. These diseases include a wide range of maladies, for example heart disease and organ failure.

There are a wide range of strategies known for formulating drugs, e.g., to maximize their therapeutic efficacy. However, it is not straightforward to predict ab initio the most appropriate strategy to apply to a new drug compound.

Compositions for improved delivery of 25HC3S or pharmaceutically acceptable salt thereof are needed. Especially beneficial would be compositions having one or more, preferably several and most preferably all of high efficacy, low toxicity, storage stability, high solubility, and isotonicity.

SUMMARY

The present disclosure addresses these needs and provides compositions comprising i) 5-cholesten-3,25-diol, 3-sulfate (25HC3S) or pharmaceutically acceptable salt thereof and ii) at least one cyclic oligosaccharide, e.g., at least one cyclodextrin and/or derivative thereof. The present disclosure also provides compositions comprising i) 5-cholesten-3,25-diol, 3-sulfate (25HC3S) or pharmaceutically acceptable salt thereof, ii) propylene glycol and iii) at least one cyclic oligosaccharide, e.g., at least one cyclodextrin and/or derivative thereof. Among other indications, the compositions have been successfully used to prevent and treat acute liver failure. However, the use of the compositions is not limited to the treatment of acute liver failure (ALF); a variety of other diseases and conditions may also be prevented and/or treated by the compositions and methods described herein, e.g. high cholesterol/high lipids, various inflammatory diseases and conditions, and organ failure of other types (e.g. kidney).

Aspects of the disclosure include:
1. A composition comprising
    5-cholesten-3,25-diol, 3-sulfate (25HC3S) or a pharmaceutically acceptable salt thereof; and
    at least one cyclic oligosaccharide.
2. The composition of aspect 1, wherein the cyclic oligosaccharide comprises a cyclodextrin or a cyclodextrin derivative.
3. The composition of aspect 2, wherein the cyclodextrin or the cyclodextrin derivative comprises at least one of cyclodextrin, alkyl substituted cyclodextrin wherein the alkyl group comprises 1 to 8 carbons, hydroxyalkyl substituted cyclodextrin wherein the alkyl group comprises 1 to 8 carbons, sulfoalkyl ether substituted cyclodextrin wherein the alkyl group comprises 1 to 8 carbons, and alkyl ether substituted cyclodextrin wherein the alkyl group comprises 1 to 8 carbons.
4. The composition of aspect 2, wherein the cyclodextrin or the cyclodextrin derivative comprises at least one of hydroxypropyl β-cyclodextrin, sulfobutyl ether I3-cyclodextrin, α-cyclodextrin and γ-cyclodextrin.
5. The composition of aspect 2, wherein the cyclodextrin or the cyclodextrin derivative consists of hydroxypropyl β-cyclodextrin or sulfobutyl ether β-cyclodextrin.
6. The composition of any of aspects 1-5, wherein the composition does not comprise hydroxypropyl I3-cyclodextrin.
7. The composition of any of aspects 1-6, wherein the cyclic oligosaccharide is present in the composition at a concentration ranging from about 0.1% (w/w) to about 99% (w/w).
8. The composition of any of aspects 1-7, wherein the cyclic oligosaccharide is present in the composition at a concentration ranging from about 0.1% (w/w) to about 90% (w/w).
9. The composition of any of aspects 1-8, wherein the cyclic oligosaccharide is present at a concentration ranging from about 1% (w/w) to about 40% (w/w).
10. The composition of any of aspects 1-9, wherein the composition further comprises at least one alcohol.
11. The composition of aspect 10, wherein the at least one alcohol comprises at least one diol.
12. The composition of aspect 11, wherein the at least one diol comprises α-propylene glycol.
13. The composition of aspect 12, wherein the α-propylene glycol is present in the composition at a concentration ranging from about 10% (v/v) to about 40% (v/v).
14. The composition of aspect 13, wherein the α-propylene glycol is present in the composition at a concentration ranging from about 15% (v/v) to about 25% (v/v).
15. The composition of any of aspects 1-14, wherein the 25HC3S or a pharmaceutically acceptable salt thereof consists of 25HC3S.
16. The composition of any of aspects 1-14, wherein the 25HC3S or a pharmaceutically acceptable salt thereof consists of a pharmaceutically acceptable salt of 25HC3S.
17. The composition of any of aspects 1-16, wherein the composition is formulated for local or systemic administration.
18. The composition of any of aspects 1-17, wherein the composition is formulated as an oral, topical, intravenous or injectable formulation.
19. The composition of any of aspects 1-18, wherein the composition comprises a lotion or cream.
20. The composition of any of aspects 1-18, wherein the composition comprises a controlled release formulation.
21. The composition of any of aspects 1-20, wherein the composition comprises a suspension.
22. The composition of any of aspects 1-21, wherein the composition comprises a physiologically acceptable carrier.
23. The composition of aspect 22, wherein the physiologically acceptable carrier comprises at least one buffer.
24. The composition of aspect 23, wherein the at least one buffer is present in the composition at a concentration ranging from about 1 to about 200 mM.

25. The composition of aspect 23, wherein the at least one buffer is present in the composition at a concentration ranging from about 2 to about 50 mM.

26. The composition of any of aspects 23 to 25, wherein the at least one buffer comprises sodium phosphate.

27. The composition of any of aspects 1-26, wherein the composition comprises at least one physiologically acceptable excipient.

28. The composition of aspect 27, wherein the at least one physiologically acceptable excipient comprises at least one salt.

29. The composition of any of aspects 27-28, wherein the at least one physiologically acceptable excipient comprises at least one polyethylene glycol.

30. The composition of any of aspects 27-29, wherein the at least one physiologically acceptable excipient comprises at least one polysorbate.

31. The composition of any of aspects 27-30, wherein the at least one physiologically acceptable excipient comprises at least one sugar other than the at least one cyclic oligosaccharide.

32. The composition of aspect 31, wherein the at least one sugar comprises dextrose.

33. The composition of any of aspects 27-32, wherein the at least one physiologically acceptable excipient comprises at least one preservative.

34. The composition of any of aspects 1-33, wherein the composition has an osmolality ranging from about 270 mmol/kg to about 340 mmol/kg.

35. The composition of any of aspects 1-34, wherein the composition comprises about 20 mg/mL to about 40 mg/mL 25HC3S and about 200 mg/mL to about 350 mg/mL hydroxypropyl beta cyclodextrin.

Further aspects provide:

36. A composition comprising:
   an oxygenated cholesterol sulfate (OCS);
   at least one cyclic oligosaccharide; and
   a thickening agent.

37. The composition of aspect 36, wherein the OCS comprises 5-cholesten-3,25-diol, 3-sulfate (25HC3S) or a pharmaceutically acceptable salt thereof.

38. The composition of aspect 36, wherein the OCS comprises 5-cholesten-3,25-diol, disulfate (25HCDS) or a pharmaceutically acceptable salt thereof.

39. The composition of any of aspects 36 to 38, wherein the OCS is present in an amount ranging from about 0.5 wt % to about 10 wt %, based on weight of the composition.

40. The composition of any one of aspects 36 to 39, wherein the cyclic oligosaccharide comprises a cyclodextrin or a cyclodextrin derivative.

41. The composition of aspect 40, wherein the cyclodextrin or the cyclodextrin derivative comprises at least one of cyclodextrin, alkyl substituted cyclodextrin wherein the alkyl group comprises 1 to 8 carbons, hydroxyalkyl substituted cyclodextrin wherein the alkyl group comprises 1 to 8 carbons, sulfoalkyl ether substituted cyclodextrin wherein the alkyl group comprises 1 to 8 carbons, and alkyl ether substituted cyclodextrin wherein the alkyl group comprises 1 to 8 carbons.

42. The composition of aspect 40, wherein the cyclodextrin or the cyclodextrin derivative comprises at least one of hydroxypropyl β-cyclodextrin, sulfobutyl ether β-cyclodextrin, α-cyclodextrin and γ-cyclodextrin.

43. The composition of aspect 40, wherein the cyclodextrin or the cyclodextrin derivative consists of hydroxypropyl β-cyclodextrin or sulfobutyl ether β-cyclodextrin.

44. The composition of any one of aspects 36 to 43, wherein the cyclic oligosaccharide is present in the composition in an amount ranging from about 5 wt % to about 50 wt %, based on weight of the composition.

45. The composition of any one of aspects 36 to 44, wherein the cyclic oligosaccharide is present in the composition in an amount ranging from about 7 wt % to about 20 wt %, based on weight of the composition.

46. The composition of any one of aspects 36 to 45, wherein the thickening agent comprises surfactant.

47. The composition of any one of aspects 36 to 46, wherein the thickening agent comprises non-ionic surfactant.

48. The composition of any one of aspects 36 to 47, wherein the thickening agent comprises amphiphilic surfactant.

49. The composition of any one of aspects 36 to 48, wherein the thickening agent comprises at least one member selected from polyacrylic acid, polyacrylic acid crosslinked with allyl sucrose, polyacrylic acid crosslinked with ally pentaerythritol, polyacrylic acid and C10-C30 alkyl acrylate crosslinked with allyl pentaerythritol, poly(ethylene glycol)-block-poly(propylene glycol)-block-poly(ethylene glycol), poloxamer, cellulose derivative, methylcellulose, carboxymethylcellulose, and carbomer.

50. The composition of any one of aspects 36 to 49, wherein the thickening agent comprises a poloxamer whose poly (propylene glycol) block has a molecular weight of 1500 to 5000 g/mol and a poly(ethylene glycol) weight fraction of 70 to 90 wt %; such as poloxamer 188 and 407.

51. The composition of any one of aspects 36 to 50, wherein the thickening agent comprises a poloxamer whose poly (propylene glycol) block has a molecular weight of 1,700 to 1,900 g/mol and a poly(ethylene glycol) weight fraction of 70 to 90 wt %; preferably poloxamer 188.

52. The composition of any one of aspects 36 to 51, wherein the thickening agent is present in the composition in an amount ranging from about 0.2 wt % to about 40 wt %, based on weight of the composition.

53. The composition of any one of aspects 36 to 52, wherein the thickening agent is present in the composition in an amount ranging from about 0.2 wt % to about 2 wt %, based on weight of the composition.

54. The composition of any one of aspects 36 to 52, wherein the thickening agent is present in the composition in an amount ranging from about 10 wt % to about 40 wt %, based on weight of the composition.

55. The composition of any one of aspects 36 to 54, further comprising an emollient.

56. The composition of any one of aspects 36 to 55, further comprising at least one emollient selected from polysorbate and sorbitan laurate.

57. The composition of aspect 55 or 56, wherein the emollient is present in the composition in an amount ranging from about 2 wt % to about 10 wt %, based on weight of the composition.

58. The composition of any one of aspects 36 to 57, further comprising a pH adjuster.

59. The composition of any one of aspects 36 to 58, further comprising a pH adjuster comprising at least one member selected from trolamine, citric acid, phosphoric acid, sodium hydroxide, and monobasic sodium.

60. The composition of any one of aspects 36 to 59, further comprising a pH adjuster comprising trolamine.

61. The composition of any one of aspects 58 to 60, wherein the pH adjuster is present in the composition in an amount ranging from about 0.5 wt % to 4 wt %, based on weight of the composition.

62. The composition of any one of aspects 36 to 61, further comprising a preservative.
63. The composition of any one of aspects 36 to 62, further comprising a paraben as a preservative.
64. The composition of any one of aspects 36 to 63, further comprising at least one member selected from methyl paraben, ethyl paraben, propyl paraben, and butyl paraben as a preservative. 65. The composition of any one of aspects 36 to 64, further comprising a preservative comprising methyl paraben.
66. The composition of any one of aspects 62 to 65, wherein the preservative is present in the composition in an amount ranging from about 0.1 wt % to about 1 wt %, based on weight of the composition.
67. The composition of any one of aspects 36 to 66, further comprising water.
68. The composition of aspect 67, wherein the water is present in an amount ranging from about 0.5 wt % to about 90 wt %, based on weight of the composition.
69. The composition of aspect 67, wherein the water is present in an amount ranging from about 1 wt % to about 10 wt %, based on weight of the composition.
70. The composition of aspect 67, wherein the water is present in an amount ranging from about 50 wt % to about 90 wt %, based on weight of the composition.
71. The composition of any one of aspects 36 to 70, wherein the composition is not an emulsion.
72. The composition of any one of aspects 36 to 71, wherein the composition comprises a micro-emulsion.
73. The composition of any one of aspects 36 to 72, wherein the composition comprises a solution.
74. The composition of aspect 73, wherein the solution is a lotion.
75. The composition of any one of aspects 36 to 72, wherein the composition is a cream.
76. The composition of any one of aspects 36 to 75, wherein the composition comprises a suspension.
77. The composition of aspect 76, wherein the suspension comprises particles comprising the OCS.
78. The composition of aspect 77, wherein the particles have an average particle size ranging from about 1 µm to about 10 µm.
79. The composition of any one of aspects 36 to 78, wherein the composition has a pH of 4 to 8, such as a pH of 4 to 7.
80. The composition of any one of aspects 36 to 79, wherein the composition has a pH of 7 to 8.
81. The composition of any one of aspects 36 to 79, wherein the composition has a pH of 5 to 6.

Further aspects include:
82. A method of treating, in a subject in need thereof at least one of: hyperlipidemia or a disease or condition caused by hyperlipidemia; dysfunction or failure of at least one organ; a lipid metabolism disorder; metabolic disorder; atherosclerosis; injury caused by ischemia; unwanted cell death; sepsis; acute radiation syndrome; a liver disorder; a lipid accumulation disorder; and an inflammatory skin disease or skin lesion; the method comprising administering to the subject a therapeutically effective amount of the composition of any of aspects 1-81.
83. The method of aspect 82, wherein the method comprises treating dysfunction or failure of at least one organ selected from kidney, liver, pancreas, heart, lung and brain.
84. The method of aspect 82, wherein the method comprises treating dysfunction or failure of the liver caused by acetaminophen.
85. The method of aspect 82, wherein the method comprises treating injury caused by ischemia.
86. The method of aspect 82, wherein the method comprises treating injury caused by ischemia caused by ischemia/reperfusion injury.
87. The method of aspect 82, wherein the method comprises treating a liver disorder.
88. The method of aspect 82, wherein the method comprises treating a liver disorder that is non-alcoholic fatty liver disease (NAFLD) or nonalcoholic steatohepatitis (NASH).
89. The method of aspect 82, wherein the method comprises treating an inflammatory skin disease or skin lesion.
90. The method of aspect 82, wherein the method comprises treating an inflammatory skin disease that is atopic dermatitis or psoriasis.
91. The method of any of aspects 82-90, wherein the administering is performed by injection.
92. The method of any of aspects 82-91, wherein the administering is performed intravenously.
93. The method of any of aspects 82-90, wherein the administering is performed topically.
94. The method of any of aspects 82-90, wherein the administering is performed orally.

Yet further additional aspects include:
95. A method of treating, in a subject in need thereof, any disease or condition disclosed herein, the method comprising administering to the subject a therapeutically effective amount of the composition of any of aspects 1-81.
96. A composition as defined in any one of aspects 1-81 for use as a medicament.
97. A composition as defined in any one of aspects 1-81 for use in treatment of any disease or condition disclosed herein.
98. The composition for use of aspect 97, wherein the disease or condition is selected from hyperlipidemia or a disease or condition caused by hyperlipidemia; dysfunction or failure of at least one organ; a lipid metabolism disorder; metabolic disorder; atherosclerosis; injury caused by ischemia; unwanted cell death; sepsis; acute radiation syndrome; a liver disorder; a lipid accumulation disorder; and an inflammatory skin disease or skin lesion.
99. Use of a composition as defined in any one of aspects 1-81 in the manufacture of a medicament for use in treatment of any disease or condition disclosed herein.
100. Use of aspect 99, wherein the disease or condition is selected from hyperlipidemia or a disease or condition caused by hyperlipidemia; dysfunction or failure of at least one organ; a lipid metabolism disorder; metabolic disorder; atherosclerosis; injury caused by ischemia; unwanted cell death; sepsis; acute radiation syndrome; a liver disorder; a lipid accumulation disorder; and an inflammatory skin disease or skin lesion.
101. A method comprising
injecting a subject with the composition of any of aspects 1-81.

Aspects of the invention provide a composition comprising 5-cholesten-3,25-diol, 3-sulfate (25HC3S) or a pharmaceutically acceptable salt thereof; and at least one cyclic oligosaccharide. In some aspects, the cyclic oligosaccharide comprises a cyclodextrin or a cyclodextrin derivative. In some aspects, the cyclodextrin or the cyclodextrin derivative comprises at least one of cyclodextrin, alkyl substituted cyclodextrin wherein the alkyl group comprises 1 to 8 carbons, hydroxyalkyl substituted cyclodextrin wherein the alkyl group comprises 1 to 8 carbons, sulfoalkyl ether substituted cyclodextrin wherein the alkyl group comprises 1 to 8 carbons, and alkyl ether substituted cyclodextrin wherein the alkyl group comprises 1 to 8 carbons. In some aspects, the cyclodextrin or the cyclodextrin derivative comprises at least one of hydroxypropyl β-cyclodextrin, sulfobutyl ether β-cyclodextrin, α-cyclodextrin and γ-cyclodextrin. In some aspects, the cyclodextrin or the cyclodextrin derivative consists of hydroxypropyl β-cyclodextrin or sulfobutyl ether β-cyclodextrin. In other aspects, the composition does not comprise hydroxypropyl β-cyclodextrin. In further aspects, the cyclic oligosaccharide is present in the composition at a concentration ranging from about 0.1% (w/w) to about 90% (w/w). In yet further aspects, the cyclic oligosaccharide is present at a concentration ranging from about 1% (w/w) to about 40% (w/w). In further aspects, the composition further comprises at least one alcohol. In further aspects, the at least one alcohol comprises at least one diol. In further aspects, the at least one diol comprises α-propylene glycol. In further aspects, the α-propylene glycol is present in the composition at a concentration ranging from about 10% (v/v) to about 40% (v/v). In further aspects, the α-propylene glycol is present in the composition at a concentration ranging from about 15% (v/v) to about 25% (v/v). In additional aspects, the 25HC3S or a pharmaceutically acceptable salt thereof consists of 25HC3S. In additional aspects, the 25HC3S or a pharmaceutically acceptable salt thereof consists of a pharmaceutically acceptable salt of 25HC3S. In some aspects, the composition is formulated for local or systemic administration. In additional aspects, the composition is formulated as an oral, topical, intravenous or injectable formulation. In additional aspects, the composition comprises a lotion or cream.

In additional aspects, the composition comprises a controlled release formulation. In additional aspects, the composition comprises a suspension. In further aspects, the composition comprises a physiologically acceptable carrier. In further aspects, the physiologically acceptable carrier comprises at least one buffer. In further aspects, the at least one buffer is present in the composition at a concentration ranging from about 1 to about 200 mM. In further aspects, the at least one buffer is present in the composition at a concentration ranging from about 2 to about 50 mM. In further aspects, the at least one buffer comprises sodium phosphate. In yet further aspects, the composition comprises at least one physiologically acceptable excipient. In further aspects, the at least one physiologically acceptable excipient comprises at least one salt. In further aspects, the at least one physiologically acceptable excipient comprises at least one polyethylene glycol. In further aspects, the at least one physiologically acceptable excipient comprises at least one polysorbate. In other aspects, the at least one physiologically acceptable excipient comprises at least one sugar other than the at least one cyclic oligosaccharide. In other aspects, the at least one sugar comprises dextrose. In other aspects, the at least one physiologically acceptable excipient comprises at least one preservative. In other aspects, the composition has an osmolality ranging from about 270 mmol/kg to about 340 mmol/kg. In additional aspects, the composition comprises about 20 mg/mL to about 40 mg/mL 25HC3S and about 200 mg/mL to about 350 mg/mL hydroxypropyl beta cyclodextrin.

Further aspects provide a method of treating, in a subject in need thereof at least one of: hyperlipidemia or a disease or condition caused by hyperlipidemia; dysfunction or failure of at least one organ; a lipid metabolism disorder; metabolic disorder; atherosclerosis; injury caused by ischemia; unwanted cell death; sepsis; acute radiation syndrome; a liver disorder; a lipid accumulation disorder; and an inflammatory skin disease or skin lesion, comprising administering to the subject a therapeutically effective amount of the composition as described herein. In some aspects, the method comprises treating dysfunction or failure of at least one organ selected from kidney, liver, pancreas, heart, lung and brain. In other aspects, the method comprises treating dysfunction or failure of the liver caused by acetaminophen. In further aspects, the method comprises treating injury caused by ischemia. In yet further aspects, the method comprises treating injury caused by ischemia caused by ischemia/reperfusion injury. In yet further aspects, the method comprises treating a liver disorder. In yet further aspects, the method comprises treating a liver disorder that is non-alcoholic fatty liver disease (NAFLD) or nonalcoholic steatohepatitis (NASH). In yet further aspects, the method comprises treating an inflammatory skin disease or skin lesion. In yet further aspects, the method comprises treating an inflammatory skin disease that is atopic dermatitis or psoriasis. In some aspects, the administering is performed by injection. In some aspects, the administering is performed intravenously. In some aspects, the administering is performed topically. In some aspects, the administering is performed orally.

Additional aspects provide a method of treating, in a subject in need thereof, any disease or condition disclosed herein, the method comprising administering to the subject a therapeutically effective amount of a composition disclosed herein.

Further aspects provide a composition as defined herein for use as a medicament.

Yet further aspects provide a composition as defined herein for use in treatment of any disease or condition disclosed herein. In some aspects, the disease or condition is selected from hyperlipidemia or a disease or condition caused by hyperlipidemia; dysfunction or failure of at least one organ; a lipid metabolism disorder; metabolic disorder; atherosclerosis; injury caused by ischemia; unwanted cell death; sepsis; acute radiation syndrome; a liver disorder; a lipid accumulation disorder; and an inflammatory skin disease or skin lesion.

Further aspects provide the use of a composition as defined herein in the manufacture of a medicament for use in treatment of any disease or condition disclosed herein. In some aspects, the disease or condition is selected from hyperlipidemia or a disease or condition caused by hyperlipidemia; dysfunction or failure of at least one organ; a lipid metabolism disorder; metabolic disorder; atherosclerosis; injury caused by ischemia; unwanted cell death; sepsis; acute radiation syndrome; a liver disorder; a lipid accumulation disorder; and an inflammatory skin disease or skin lesion.

Further aspects include a method comprising injecting a subject with a composition as disclosed herein.

BRIEF DESCRIPTION OF THE DRAWINGS

The present invention is further described in the description of invention that follows, in reference to the noted plurality of non-limiting drawings, wherein.

DETAILED DESCRIPTION OF THE DISCLOSURE

Figure 1:
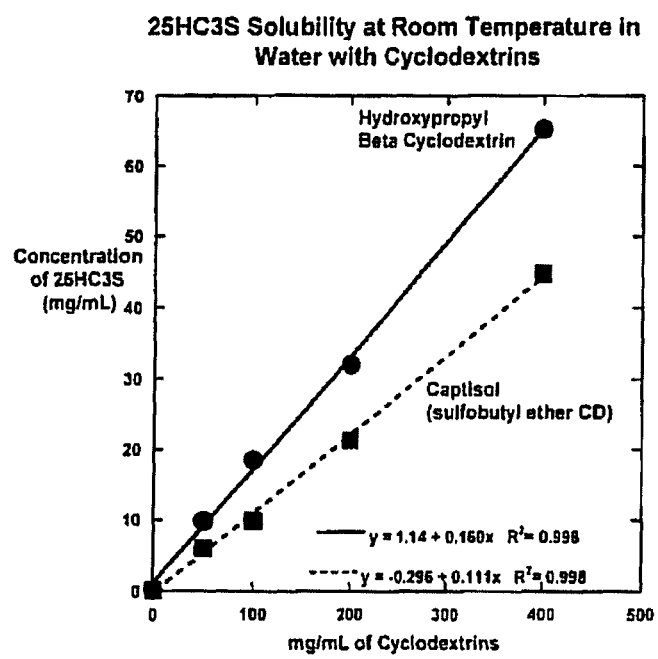
FIG. 1 shows a solubility phase diagram which is a plot of the maximum equilibrium solubility of 25HC3S (mg/mL) as a function of hydroxypropyl beta cyclodextrin (HPbCD) and sulfobutyl ether beta cyclodextrin (SBECD) concentrations (mg/mL) in water.

Compositions comprising 5-cholesten-3,25-diol, 3-sulfate (25HC3S) or pharmaceutically acceptable salt thereof and at least one cyclic oligosaccharide, such as at least one cyclodextrin (CD) and/or derivative thereof, are provided. Compositions comprising 25HC3S or pharmaceutically acceptable salt thereof, propylene glycol (PG) and at least one cyclic oligosaccharide, such as at least one cyclodextrin (CD), are also provided. The compositions are used to prevent and/or treat a wide variety of diseases and conditions, such as hyperlipidemia, ischemia, sepsis, heart disease, and organ failure.

Definitions

The following definitions are used throughout:

As used herein, "at least one" means one, two, three, four, or more.

The compositions described herein include 5-cholesten-3,25-diol, 3-sulfate (25HC3S) or pharmaceutically acceptable salt thereof. Disclosure of 25HC3S or pharmaceutically acceptable salt thereof is found in, e.g., U.S. Pat. No. 8,399,441, which is incorporated herein by reference in its entirety.

The 25HC3S or pharmaceutically acceptable salt thereof is typically a synthetic version of 25HC3S that occurs naturally in the body. The 25HC3S or pharmaceutically acceptable salt thereof may be administered in forms not naturally found in the body, and in concentrations that are significantly higher than those which occur naturally. The natural levels typically range from e.g. about 2 ng/ml or less up to about 5 ng/ml in the blood or plasma. The concentration of 25HC3S or pharmaceutically acceptable salt thereof in the blood or plasma of a patient that is treated with 25HC3S or pharmaceutically acceptable salt thereof is generally greater than about 5 ng/ml, and generally ranges from about 50 ng/ml to about 5000 ng/ml, such as about 80 ng/ml to about 3000 ng/ml, e.g. from about 100 to about 2000 ng/ml, or from about 200 to about 1000 ng/ml.

In one aspect, the 25HC3S is of formula

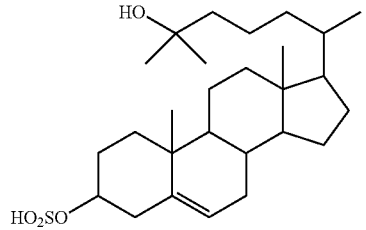

and/or a pharmaceutically acceptable salt thereof.

In one aspect, the 25HC3S is 5-cholesten-β, 25-diol, 3-sulfate of formula

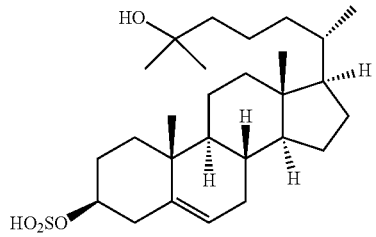

and/or a pharmaceutically acceptable salt thereof.

An oligosaccharide is a saccharide polymer containing two or more sugar molecules (monomers), for example 2 to 200 sugar molecules such as 3 to 100 sugar molecules or 3 to 10 sugar molecules. "Cyclic oligosaccharide" refers to an oligosaccharide that is cyclic. Typically a cyclic oligosaccharide comprises 5 or more sugar molecules that together form a ring, for example 5 to 200 sugar molecules such as 5 to 100 sugar molecules or 5 to 10 sugar molecules. Cyclic oligosaccharides include salts of cyclic oligosaccharides.

"Cyclodextrin" ("CD") refers to a family of synthetic compounds comprising sugar molecules bound together in a ring (cyclic oligosaccharides). Cyclodextrins are cyclic oligosaccharides with hydroxyl groups on the outer surface and a void cavity in the center. Their outer surface is hydrophilic, and therefore they are usually soluble in water, but the cavity has a lipophilic character.

The most common cyclodextrins are α-cyclodextrin, β-cyclodextrin and γ-cyclodextrin, consisting of 6, 7, and 8 α-1,4-linked glucose units, respectively. The number of these units determines the size of the cavity. Cyclodextrins typically comprise 5 or more α-D-glucopyranoside units linked 1-4, as in amylose. Typical cyclodextrins contain from six to eight units in a ring, creating a cone shape and include: α (alpha)-cyclodextrin, a 6-membered ring; β (beta)-cyclodextrin: a 7-membered ring, and γ (gamma)-cyclodextrin, an 8-membered ring. Much larger cyclodextrin rings are also known, e.g. comprising over 100 α-D-glucopyranoside units. Cyclodextrins suitable for medical purposes are readily commercially available. Cyclodextrins include salts of cyclodextrins.

Various derivatives of CDs may also be employed, including but not limited to: chloramphenicol/methyl-β-CD; highly water-soluble, randomly substituted hydroxyalkyl derivatives of β- and γ-CD such as 2-hydroxypropyl-β-cyclodextrin and 2-hydroxypropyl-γ-cyclodextrin; sulfoalkyl ether CDs such as sulfobutylether β-cyclodextrin; lipid substituted CDs; dimethyl-β-CD, randomly methylated 13-CD, and the like. In some aspects, the cyclodextrin is β-cyclodextrin or sulfobutyl ether β-cyclodextrin.

Common cyclodextrin derivatives are formed by alkylation (e.g., methyl- and ethyl-β-cyclodextrin) or hydroxyalkylation of the hydroxyl groups hydroxypropyl- and hydroxyethyl-derivatives of α-, β-, and γ-cyclodextrin) or by substituting the primary hydroxyl groups with saccharides (e.g. glucosyl- and maltosyl-β-cyclodextrin). For instance, cyclodextrin derivatives include cyclodextrins that are alkyl substituted, hydroxyalkyl substituted, sulfoalkyl ether substituted, or alkyl ether substituted, such as those in which the alkyl group comprises 1 to about 8 carbons, such as about 2 to about 5 carbons. In such a derivative, the cyclodextrin may be fully or partially alkyl substituted, hydroxyalkyl substituted, sulfoalkyl ether substituted, or alkyl ether substituted (i.e. all or, more typically, only some of the native hydroxyl groups of the cyclodextrin are replaced with alkyl substituents, hydroxyalkyl substituents, sulfoalkyl ether substituents, or alkyl ether substituents). Cyclodextrin derivatives also include cyclodextrin ethers. Hydroxypropyl-β-cyclodextrin and its preparation by propylene oxide addition to β-cyclodextrin, and hydroxyethyl β-cyclodextrin and its preparation by ethylene oxide addition to β-cyclodextrin, were described in a patent of Gramera et al. (U.S. Pat. No. 3,459,731, issued August 1969) over 20 years ago. For a comprehensive review of cyclodextrins see Cyclodextrins and their industrial uses, editor Dominique Duchene, Editions Sante, Paris, 1987. For a more recent overview, see J. Szejtli: Cyclodextrins in drug formulations: Part 1, Pharm. Techn. Int. 3(2), 15-22 (1991); and i. Szejtli: Cyclodextrins in drug formulations: Part II, Pharm. Techn. Int. 3(3), 16-24 (1991).

Cyclodextrins approved for parenteral applications include two β-cyclodextrins (hydroxypropyl β-cyclodextrin "HPbCD", also known as hydroxypropyl betadex and sulfobutyl ether β-cyclodextrin "SBECD"), α-cyclodextrin and γ-cyclodextrin. HPbCD and other cyclodextrins are also approved for oral, topical, dermal, sublingual, buccal, eye drops, and nasal routes.

While not wishing to be bound by theory, the stability of the resulting complex depends on how well the guest molecule fits into the cyclodextrin cavity. Cyclodextrins have previously been used to increase the solubility, dissolution rate and/or stability of some compounds. However, there are also many drugs for which cyclodextrin complexation is not possible or is otherwise incapable of conferring beneficial properties. As with other formulation strategies, the ability of cyclodextrin to confer beneficial properties on a particular drug is difficult to predict ab initio.

"Propylene glycol" or "α-propylene glycol" or "propane-1,2-diol" or simply "PG" refers to an organic compound with the chemical formula $C_3H_8O_2$. Propylene glycol suitable for medical purposes is readily commercially available.

Prevent and Treat

As used herein, "prophylactically treat" ("prophylactic treatment", "prophylactically treating" etc.) and "prevent" ("prevention", "preventing" etc.) refer to warding off or averting the occurrence of at least one symptom of a disease or unwanted condition (such as ALF or another disease or condition described herein), by prophylactic administration of a composition comprising 25HC3S or pharmaceutically acceptable salt thereof and at least one cyclic oligosaccharide, e.g., at least one CD, to a subject in need thereof. Generally, "prophylactic" or "prophylaxis" relates to a reduction in the likelihood of the patient developing a disorder. Typically, the subject is considered by one of skill in the art to be at risk of or susceptible to developing at least one symptom of the disease or unwanted condition, or is considered to be likely to develop at least one symptom of the disease/condition in the absence of medical intervention. Generally, however, for "prevention" or "prophylactic treatment", administration occurs before the subject has, or is known or confirmed to have, symptoms of the disease (condition, disorder, syndrome, etc.; unless otherwise indicated, these terms are used interchangeably herein). In other words, symptoms may not yet be overt or observable. The subject may be considered at risk due to a variety of factors, including but not limited to: genetic predisposition; an impending medical or surgical procedure (e.g. surgery, use of a contrast dye in imaging, chemotherapy, etc.); recent certain or suspected or unavoidable future exposure to a toxic agent (e.g. a toxic chemical or medication, radiation, etc.); or exposure to or experience of another stressor or combination of stressors that is/are linked to or associated with the development of the disease/condition which is being prevented. For example, in some aspects, what is prevented is organ dysfunction/failure (e.g. ALF), and the subject may already display symptoms of a potential precursor of organ dysfunction/failure, for example, ischemia, sepsis, a harmful or inappropriate level of inflammation, deleterious cell death, necrosis, etc. In such aspects, treatment of the subject may prevent the noxious or harmful effects or outcomes (results) of the precursor condition, for example, the treatment may prevent death. "Prevention" or "prophylactic treatment" of a disease or condition may involve completely preventing the occurrence of detectable symptoms, or, alternatively, may involve lessening or attenuating the degree, severity or duration of at least one symptom of the disease that would occur in the absence of the medical interventions provided herein. Alternatively, the subject may be experiencing early stage symptoms and what is prevented is the progression to more severe or full-blown disease.

"Treat" (treatment, treating, etc.) as used herein refers to administering at least one composition comprising 25HC3S or pharmaceutically acceptable salt thereof and at least one cyclic oligosaccharide, e.g., CD, to a subject that already exhibits at least one symptom of a disease. In other words, at least one parameter that is known to be associated with the disease has been measured, detected or observed in the subject. For example, some organ dysfunction/failure and/or precursors thereof that are treated as described herein are caused by somewhat predictable factors (e.g. APAP overdose), or by unexpected causes such as trauma due to accidents (recreational and non-recreational), war injuries, undiagnosed allergies or other risk factors, etc. "Treatment" of a disease involves the lessening or attenuation, or in some instances, the complete eradication, of at least one symptom of the disease that was present prior to or at the time of administration of the composition. Thus, for example, treatment of ALF includes treating damage associated with ALF.

APAP overdose: Generally, a serum plasma concentration of APAP of 140-150 microgram/mL (or milligrams/L) at 4 hours post ingestion, on the Rumack-Matthew nomogram, indicates the need for APAP overdose treatment. The Rumack-Matthew nomogram is a logarithmic graph starting not directly from ingestion, but from 4 hours post ingestion after absorption is considered likely to be complete. However, the nomogram is not used alone if the patient has altered mental status (e.g. is suicidal) or if the history is not reliable. Rather, a second level is drawn and plotted to see if the slope of the line remains at or above the nomogram. A formal half-life may also be determined, e.g. by measuring APAP blood levels at time (t=0) (upon admission of the patient) and at time (t=4 hrs). If the half-life is more than 4 hours, then treatment is likely necessary to prevent hepatotoxicity and liver failure. However, treatment may be undertaken at lower blood plasma levels if deemed warranted, e.g. in a child or the elderly, as some persons are especially sensitive to APAP. Generally, if more than 4000 mg of APAP is ingested in a 24 hour period, an overdose might be suspected. Ingestion of 7000 mg or more can lead to a severe overdose if not treated. Symptoms of an overdoes include: abdominal pain, appetite loss, coma, convulsions, diarrhea, irritability, jaundice, nausea, sweating, upset stomach, and vomiting, each of which may be prevented or treated by administration of the compositions described herein.

Compositions

The compositions described herein generally comprise 25HC3S or pharmaceutically acceptable salt thereof, at least one cyclic oligosaccharide, e.g., CD and, in some aspects, PG. In some aspects, the 25HC3S or pharmaceutically acceptable salt thereof is present in the composition in an amount ranging from about 0.01 to about 75% (w/w), e.g., about 0.1 to about 50% (w/w), about 1 to about 25% (w/w), about 2 to about 20% (w/w), or about 3 to about 10% (w/w).

If the 25HC3S or pharmaceutically acceptable salt thereof is present in a liquid, lotion, or cream composition (including liquid solutions, suspensions, such as liquid suspensions, lotions, creams, etc.), the concentration of the 25HC3S or pharmaceutically acceptable salt thereof generally ranges from about 0.01 to about 200 mg/ml, or from about 0.1 to 100 mg/ml, and is generally from about 1 to about 50 mg/ml, e.g. is about 1, 5, 10, 15, 20, 25, 30, 35, 40, 45, or 50 mg/ml.

If the 25HC3S or pharmaceutically acceptable salt thereof is present in a solid or semi-solid composition (e.g., a gel or other solidified preparation), the concentration of the 25HC3S or pharmaceutically acceptable salt thereof generally ranges from about 0.01 to about 75% (w/w) or from about 0.1 to about 50% (w/w), and is generally from about 1 to about 25% (w/w), e.g. is about 1, 5, 10, 15, 20, 25, 30, 35, 40, 45, or 50% (w/w).

If the 25HC3S or pharmaceutically acceptable salt thereof is present in a lyophilized solid composition, the concentration of the 25HC3S or pharmaceutically acceptable salt thereof generally ranges from about 0.01 to about 75% (w/w), about 0.1 to about 50% (w/w), and is generally from about 1 to about 15% (w/w), e.g. is about 1, 2, 3, 4, 5, 6, 7, 8, 9, 10, 11, 12, 13, 14, or 15% (w/w).

In some aspects, at least one cyclic oligosaccharide is present in the composition in an amount ranging from about 0.1% (w/w) to about 99% (w/w), e.g., about 0.1 to about 90% (w/w), about 1 to about 90% (w/w), about 1 to about 80% (w/w), about 1 to about 40% (w/w), about 2 to about 50% (w/w), about 3 to about 40% (w/w), or about 4 to about 30% (w/w). In some aspects, at least one cyclic oligosaccharide is present in a solution product in a range from about 1 to about 65% (w/v), e.g. about 1, 2, 3, 4, 5, 10, 20, 30 or 40% (w/v). In some aspects, the amount is 25% (w/v). In some aspects, at least one cyclic oligosaccharide is present in a lyophilized solid product (e.g. for reconstitution) in a range from about 1 to about 90% (w/w), e.g. about 1, 5, 10, 40, 50, 60, 70, 80 or 90% (w/w). In some aspects, the amount is 89% (w/w). In some aspects, at least one cyclic oligosaccharide is present in a solid product for administration in a range from about 1 to about 90% (w/w), e.g. about 1, 5, 10, 40, 50, 60, 70, 80 or 90% (w/w). In some aspects, the amount is 89% (w/w).

In some aspects, CD is present in the composition in an amount ranging from about 0.1% (w/w) to about 99% (w/w), e.g., about 0.1 to about 90% (w/w), about 1 to about 90% (w/w), about 1 to about 80% (w/w), about 1 to about 40% (w/w), about 2 to about 50% (w/w), about 3 to about 40% (w/w), or about 4 to about 30% (w/w). In some aspects, CD is present in a solution product in a range from about 1 to about 65% (w/v), e.g. about 1, 2, 3, 4, 5, 10, 20, 30 or 40% (w/v). In some aspects, the amount is 25% (w/v). In some aspects, CD is present in a lyophilized solid product (e.g. for reconstitution) in a range from about 1 to about 90% (w/w), e.g. about 1, 5, 10, 40, 50, 60, 70, 80 or 90% (w/w). In some aspects, the amount is 89% (w/w). In some aspects, CD is present in a solid product for administration in a range from about 1 to about 90% (w/w), e.g. about 1, 5, 10, 40, 50, 60, 70, 80 or 90% (w/w). In some aspects, the amount is 89% (w/w).

In some aspects, PG is present in the compositions in a range of from about 10 to about 40% (v/v), e.g. is about 10, 15, 20, 25, 30, 35 or 40% (v/v). In some aspects, the amount is 20% (v/v).

The compositions are generally administered in a pharmaceutically acceptable formulation which includes suitable excipients, elixirs, binders, and the like (generally referred to as "pharmaceutically and physiologically acceptable carriers"), which are pharmaceutically acceptable and compatible with the active ingredients.

Drug carriers may also be used to improve the pharmacokinetic properties, specifically the bioavailability, of many drugs with poor water solubility and/or membrane permeability.

In some aspects, the composition contains a pharmaceutically acceptable buffer, or buffers, such as phosphate, acetate, ammonia, borate, citrate, carbonate, glycine, lactate, lysine, maleic, succinate, tartrate or tromethamine. In some aspects, the buffer concentrations in the composition range from about 0.1 to about 200 mM, in some aspects they range from about 1 to about 50 mM, and in some aspects, they range from about 5 to about 15 mM.

In some aspects, the compositions include one or more thickening agents. Exemplary thickening agents include but are not limited to: polyethylene glycol, polyethylene oxide, synthetic polymers and vegetable gums; cellulose derivatives (methylcellulose (MC), carboxymethylcellulose (CMC), hydroxypropylcellulose, hydroxypropyl methylcellulose), carbomers (polyacrylic acids such as Carbopol® 910, Carbopol® 941), cetearyl alcohol, magnesium aluminum silicate, acryloyldimethyl taurate copolymer, various multipblock copolymers, poloxamers (Pluronic®), various carboxylic acid polymers (e.g. acrylates), sulfonated polymers (e.g. sodium polyacryloyldimethyl taurate), clays, silicon dioxide, and copolymers, hydrophobically modified derivatives, and mixtures thereof. Gums, including natural gums, include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, fumed silica, hydroxypropyl chitosan, hydroxypropyl guar, karaya gum, kelp, locust bean gum, natto gum, potassium alginate, sodium alginate, potassium carrageenan, propylene glycol alginate, sclerotium gum, sodium carboxymethyl dextran, sodium carrageenan, tragacanth gum, xanthan gum, derivatives thereof and mixtures thereof. In some aspects, the thickening agent is one or more of polyacrylic acid, polyacrylic acid crosslinked with allyl sucrose (a Carbopol®), polyacrylic acid crosslinked with allyl pentaerythritol (a Carbopol®), polyacrylic acid and C10-C30 alkyl acrylate crosslinked with allyl pentaerythritol (a Carbopol®), poly(ethylene glycol)-block-poly(propylene glycol)-block-poly(ethylene glycol) (Lutrol®F127) or poloxamer 188 (Pluronic® F68). In some aspects, the thickening agent(s) include a surfactant such as a non-ionic surfactant and/or an amphiphilic surfactant. In some aspects, the thickening agent(s) include polyacrylic acid, polyacrylic acid crosslinked with allyl sucrose, polyacrylic acid crosslinked with allyl pentaerythritol, polyacrylic acid and C10-C30 alkyl acrylate crosslinked with allyl pentaerythritol, poly(ethylene glycol)-block-poly(propylene glycol)-block-poly(ethylene glycol), poloxamer, cellulose derivative, methylcellulose, carboxymethylcellulose, and carbomer. Thickening agents include poloxamers, e.g. those whose poly(propylene glycol) block has a molecular weight of 1,700 to 1,900 g/mol and a poly(ethylene glycol) weight fraction of 70 to 90 wt %. In some aspects, the poloxamer is poloxamer 188. In some aspects, the compositions described herein include one or more pH adjusters, e.g. at a wt/% of from about 0.5 to 4, based on the weight of the composition. Exemplary pH adjusters include but are not limited to: adipic acid, aliphatic amine neutralizing agents (ethanolamine, triethanolamine, diisopropanolamine), alpha-ketoglutaric acid, 2-amino-2-methyl-1,3-propanediol, 2-amino-2-methyl-1-propanol, 1-amino-2-propanol, ammonium bicarbonate, ammonium phosphate, ascorbic acid, benzoic acid, calcium citrate, calcium hydroxide, citric acid, phosphoric acid, tartaric acid, sodium hydroxide, a phosphate, monobasic sodium phosphate, a carbonate, an acetate, sodium hydroxide, potassium hydroxide, trolamine, and the like. In some aspects, trolamine is used to adjust the pH.

In some aspects, the compositions described herein include one or more emollients. Emollients are supple, waxlike, lubricating, thickening agent that prevents water loss and have a softening and soothing effect on skin. Examples of emollients are ingredients like plant oils, mineral oil, shea butter, cocoa butter, petrolatum, and fatty acids (animal oils, including emu, mink, and lanolin, the latter probably the one ingredient that is most like our own skin's oil). More technical-sounding emollient ingredients, such as triglycerides, benzoates, myristates, palmitates, and stearates, are generally waxy in texture and appearance but provide most moisturizers with their elegant texture and feel.

Exemplary emollients for use in aqueous lotion compositions having a low pH and increased spreading and slip characteristics include, but are not limited to, soy lecithin, C12-C15 alkyl benzoate, stearic acid, white wax, yellow wax, carnauba wax, cetyl ester wax, microcrystalline wax, paraffin wax, caprylic/capric triglyceride, glycerin, glyceryl stearate, PEG-10 sunflower oil glycerides; vegetable oils like sunflower oil, palm oil, olive oil, emu oil, babassu oil, evening primrose oil, palm kernel oil, cottonseed oil, jojoba oil, meadowfoam seed oil, sweet almond oil, canola oil, soybean oil, avocado oil, safflower oil, coconut oil, sesame oil, rice bran oil, and grape seed oil; mineral oil; esters like isopropyl stearate, isostearyl isononanoate, diethylhexyl fumarate, diisostearyl malate, triisocetyl citrate, stearyl stearate, diglycol stearate, methyl palmitate, and methylheptyl isostearate; petrolatum; hydrous lanolin, lanolin oil, lanolin alcohol, and lanolin wax; long chain alcohols like cetyl alcohol, stearyl alcohol, behenyl alcohol, isostearyl alcohol, 2-hexyldecanol and myristyl alcohol; dimethicone fluids of various molecular weights and mixtures thereof; PPG-15 stearyl ether (also known as arlatone E); shea butter; olive butter; sunflower butter; coconut butter; jojoba butter; cocoa butter; squalane and squalene; isoparaffins; polyethylene glycols of various molecular weights; polypropylene glycols of various molecular weights; and mixtures thereof. In some aspects, the emollient is a polysorbate (e.g. Tween®) and/or a sorbitan ester such as a Span® (e.g. sorbitan monolaurate. Span® 20). In some aspects, the emollient is present in the composition in an amount ranging, for example, from about 2 wt % to about 10 wt %.

In additional aspects, the compositions described herein include one or more preservatives. Exemplary preservatives include but are not limited to: imidurea, acids such as benzoic acid, sorbic acids, boric acids, etc; esters such as methylparaben, ethylparaben, propylparaben, butylparaben, sodium benzoate, sodium propionate, potassium sorbate, etc.; alcohols such as chlorobutanol, benzyl alcohol, phenyl ethyl alcohol, etc.; phenols such as phenol, chlorocresol, o-phenyl phenol, phenoxyethanol, etc.; mercurial compounds such as thiomersal, nitromersol, phenylmercuric nitrate, phenylmercuric acetate, etc.; and quaternary ammonium compounds such as benzalkonium chloride, cetyl pyridinium chloride, etc. and combination of these, e.g. a combination of methylparaben and propylparaben.

The 25HC3S and cyclic oligosaccharide, e.g., CD, may be present in the formulation as pharmaceutically acceptable salts (e.g. alkali metal salts such as sodium, potassium, calcium or lithium salts, ammonium, etc.) or as other complexes. It should be understood that the pharmaceutically acceptable formulations include solid, semi-solid, and liquid materials conventionally utilized to prepare solid, semi-solid and liquid dosage forms such as tablets, capsules, creams, lotions, ointments, gels, foams, pastes, aerosolized dosage forms, and various injectable forms (e.g. forms for intravenous administration), etc.

Suitable pharmaceutical carriers include but are not limited to inert solid diluents or fillers, sterile aqueous solutions and various organic solvents for parenteral use, such as polyethylene glycol (PEG, such as PEG 300 and PEG 400), ethanol, benzyl alcohol, benzyl benzoate, propylene glycol, N,N-dimethylacetamide, N-methyl-2-pyrrolidone, vegetable oils (sesame, soybean, corn, castor, cottonseed, and peanut) and glycerin. Examples of solid carriers (diluents, excipients) include lactose, starch, conventional disintegrating agents, coatings, lactose, terra alba, sucrose, talc, gelatin, agar, pectin, acacia, magnesium stearate, stearic acid and lower alkyl ethers of cellulose. Examples of liquid carriers include but are not limited to various aqueous or oil based vehicles, saline, dextrose, glycerol, ethanol, isopropanol, phosphate buffer, syrup, peanut oil, olive oil, phospholipids, fatty acids, fatty acid amines, polyoxyethylene, isopropyl myristate, ethyl cocoate, octyl cocoate, polyoxyethylenated hydrogenated castor oil, paraffin, liquid paraffin, propylene glycol, celluloses, parabens, stearyl alcohol, polyethylene glycol, isopropyl myristate, phenoxyethanol, and the like, or combinations thereof. Water may be used as the carrier for the preparation of compositions which may also include conventional buffers and agents to render the composition isotonic. Oral dosage forms may include various thickeners, flavorings, diluents, emulsifiers, dispersing aids, binders, coatings and the like. The composition of the present disclosure may contain any such additional ingredients so as to provide the composition in a form suitable for the intended route of administration. In addition, the composition may contain minor amounts of auxiliary substances such as wetting or emulsifying agents, pH buffering agents, and the like. Similarly, the carrier or diluent may include any sustained release material known in the art, such as glycerol monostearate or glycerol distearate, alone or mixed with wax. Other potential additives and other materials (preferably those which are generally regarded as safe [GRAS]) include: colorants; flavorings; surfactants (e.g., non-ionic surfactants including polysorbate (such as TWEEN®20, 40, 60, and 80 polyoxyethylene sorbitan monolaurate), sorbitan esters (such as Span 20, 40, 60, and 85), and poloxamers (such as Pluronic® L44, Pluronic® F68, Pluronic® F87, Pluronic® F108 and Pluronic® F127); zwitterionic surfactant such as lecithin; anionic surfactants such as sodium dodecyl sulphate (SDS) and sulphated castor oil; and cationic surfactants such as benzalkonicum chloride and cetrimide. Surfactants include polyoxyl 35 castor oil (Cremophor® EL), polyoxyl 40 hydrogenated castor oil (Cremophor® RH 40), polyoxyl 60 hydrogenated castor oil (Cremophor® RH 60), d-α-tocopheryl polyethylene glycol 1000 succinate (TPGS), poly-oxyethylene esters of 12-hydroxystearic acid (Solutol® HS-15), PEG 300 caprylic/capric glycerides (Softigen® 767), PEG 400 caprylic/capric triglycerides (Labrafil® M-1944CS), PEG 300 linoleic glycerides (Labrafil® M-2125CS), polyoxyl 8 stearate (PEG 400 monostearate), polyoxyl 40 stearate (PEG 1750 monostearate), peppermint oil, oleic acid, etc.); and solvents, stabilizers, binders or encapsulants (lactose, liposomes, etc.). Preservatives such as benzyl alcohol, phenol, chlorobutanol, 2-ethoxyethanol, methyl paraben, ethyl paraben, propyl paraben, benzoic acid, sorbic acid, potassium sorbate, chlorhexidine, 3-cresol, thimerasol, phenylmercurate salts, sodium benzoate, cetrimonium bromide, benzethonium chloride, alkyltrimethylammonium bromide, cetyl alcohol, steryl alcohol, chloroactamide, trichlorocarban, bronopol, 4-chlorocresol, 4-chloroxylenol, hexachloropherene, dichlorophene, or benzalkium chloride may also be used. Depending on the fon iulation, it is expected that the active components (e.g. 25HC3S or pharmaceutically acceptable salt thereof) will each be present at about 1 to about 99% (w/w) of the composition and the vehicular "carrier" will constitute about 1 to about 99% (w/w) of the composition.

The pharmaceutical compositions of the present disclosure may include any suitable pharmaceutically acceptable additives or adjuncts to the extent that they do not hinder or interfere with the therapeutic effect(s) of the composition. Still other suitable formulations for use in the present disclosure can be found, for example in Remington's Pharmaceutical Sciences 22nd edition, Allen, Loyd V., Jr editor (September 2012); and Akers, Michael J. Sterile Drug Products: Formulation, Packaging, Manufacturing and Quality; publisher Informa Healthcare (2010).

The compositions generally have a pH that is physiologically compatible, e.g. in the range of from about 4 to about 8.5, e.g. about 4, 4.5, 5.0, 5.5, 6.0, 6.5, 7.0, 7.5, 8.0 or 8.5. For internal or systemic administration, the pH is generally in the range of from about 6 to about 8, and may be from about 7.4 to about 8, e.g. about 7.4, 7.5, 7.6, 7.7, 7.8, 7.9 or 8.0. For topical administration, the pH may be lower to approximately the pH of skin (5.5), e.g. in the range of from about 4-7, or about 5 to about 6, e.g. 5.1, 5.2, 5.3, 5.4, 5.5, 5.6, 5.7, 5.8, 5.9 or 6.0.

In addition, formulations used for the treatment of ALF optionally also include additional suitable co-formulated (or optionally, co-administered) agents that are used to e.g. combat acetaminophen toxicity, including but not limited to: metabolites of the methionine and/or glutathione biosynthetic pathways such as S-adenosylhomocysteine (SAH), S-methylmethionine (SMM), cystine, betaine, etc. or various forms and/or salts thereof e.g. acetylcysteine (e.g. intravenous N-acetylcysteine), as well as various neutraceuticals, activated charcoal, etc.

Generally, the compositions have an osmolality of from about 200 to about 2000 mmol/kg, such as about 270 to about 340 mmol/kg, e.g. about 270, 280, 290, 300, 310, 320, 330 or 340 mmol/kg, so that the composition (e.g., solution) is isotonic (iso-osmotic) with the blood, thereby decreasing pain upon injection, and precluding a need to add an isotonic agent. In some aspects, the compositions comprise about 30 mg/mL 25HC3S or pharmaceutically acceptable salt thereof and about 250 mg/mL HPbCD in a physiologically acceptable carrier such as 10 mM sodium phosphate buffer in water, and the isotonicity is about 320 mmol/kg. In general, concentrations of HPbCD greater than 250 mg/mL with higher than 30 mg/mL concentrations of 25HC3S or pharmaceutically acceptable salt thereof lead to hypertonic solutions, which can cause pain upon subcutaneous and intramuscular injection. However, higher drug and HPbCD concentrations can be prepared and diluted with sterile water for IV infusion. Conversely, concentrations of HPbCD less than about 250 mg/mL with less than about 30 mg/mL concentrations of 25HC3S or pharmaceutically acceptable salt thereof may benefit from the addition of an isotonic agent, such as sodium chloride or mannitol, to bring the isotonicity into an expected range for a parenteral dosage form. The manufacture of exemplary compositions is described in Examples 1 and 2 below.

The compositions are typically administered as liquid solutions, suspensions, emulsions, etc. or liquids suitable for injection and/or intravenous administration; various controlled release formulations; or as a cream or lotion; and the like. Solid forms suitable for administration, or for solution in, or suspension in, liquids prior to administration, are also encompassed.

Controlled release refers to the presentation or delivery of compounds in response to time or a stimulus, and commonly refers to time dependent release in oral dose formulations. Controlled release has several variants such as sustained release (where prolonged release is intended), pulsed release (bursts of drug are released at different times), delayed release (e.g. to target different regions of the gastrointestinal tract tract), etc. Controlled release formulations may prolong drug action and maintain drug levels within a desired therapeutic window to avoid potentially hazardous peaks in drug concentration following ingestion or injection, and to maximize therapeutic efficiency. In addition to pills, capsules and injectable drug carriers (that often have an additional release function), forms of controlled release medicines include gels, implants, devices and transdermal patches.

In some aspects, e.g. for the treatment of acute ALF, the compositions are formulated for intravenous (IV) administration. In this case, the volume that is administered is generally greater than when other administration modes are used, e.g. about 50 to 1000 ml. In some aspects, formulations for IV infusion administration contain a lesser amount of cyclic oligosaccharide, e.g., CD, e.g. about 0.25 to about 25% (w/v), such as 0.2, 0.5, 1.0, 1.5, 2.0, 2.5, 3, 3.0.5, 4.0, 4.5, 5, 10, 15, 20, 25% (w/v). In such formulations, the amounts of 25HC3 S or pharmaceutically acceptable salt thereof and PG are still in the ranges described elsewhere herein.

In contrast, for compositions that are used for intramuscular or intraperitoneal injection, the volume of liquid that is used to deliver a dose is typically much lower, e.g. from about 0.5 to about a 10 ml maximum. For such formulations, the amounts of cyclic oligosaccharide, e.g., CD, may be greater, e.g. from about 2 to about 40% (w/v), such as about 2, 5, 10, 15, 20, 25, 30, 35 or 40% (w/v).

Exemplary Diseases/Conditions that are Prevented and/or Treated

Organ Dysfunction and Failure

In some aspects, methods for preventing and/or treating organ or organ system failure are provided. The methods include contacting an organ of interest (e.g. the liver) with a composition as described herein. If the organ of interest is within a patient (in vivo), then contact generally involves administering to the patient an amount of a composition that is effective or sufficient to prevent and/or treat dysfunction and/or failure of one or more organs or organ systems in the patient, e.g. is therapeutically effective to prevent or treat at least one symptom of organ dysfunction or failure exhibited by the patient.

Methods of preventing and/or treating conditions which lead to, cause or are caused by, or which are associated with organ dysfunction and failure are also described, e.g. prevention and/or treatment of inflammation, cell death (e.g. necrosis), consequences of ischemia, sepsis, and others. The methods involve administering, to a subject in need thereof, an amount of a composition that is effective or sufficient to prevent and/or treat the condition.

As used herein, "organ" refers to a differentiated and/or relatively independent body structure comprising cells and tissues that performs some specialized function in the body of an organism. An "organ system" refers to two or more organs that work together in the execution of a body function. A hollow organ is an internal visceral organ (viscus) that forms a hollow tube or pouch, or that includes a cavity. Exemplary organs, the dysfunction or failure of which are prevented and/or treated by the administration of or contact with a composition of the present disclosure, include but are not limited to: heart, lungs, (e.g., lungs damaged by pulmonary fibrosis, e.g., associated with chronic asthma), liver, pancreas, kidneys, brain, intestines, colon, thyroid, etc. In some cases, the dysfunction or failure which is prevented and/or treated by the administration of the 25HC3S or pharmaceutically acceptable salt thereof involves an organ other than the liver, for example heart, lungs, pancreas, kidneys, brain, intestines, colon, etc. In general, methods and compositions described herein that refer to "organs" should also be understood to include "organ systems", unless otherwise specified.

"Organ dysfunction" denotes a condition or a state of health where an organ does not perform its expected function. Organ function represents the expected function of the respective organ within physiologic ranges. The person skilled in the art is aware of the respective function of an organ during medical examination. Organ dysfunction typically involves a clinical syndrome in which the development of progressive and potentially reversible physiological dysfunction in an organ, optionally in the absence of anatomic injuries.

"Organ failure" denotes an organ dysfunction to such a degree that normal homeostasis cannot be maintained without external clinical intervention.

"Acute organ dysfunction" refers to reduced organ function that occurs rapidly—in days or weeks (e.g., within 26 weeks, within 13 weeks, within 10 weeks, within 5 weeks, within 4 weeks, within 3 weeks, within 2 weeks, within 1 week, within 5 days, within 4 days, within 3 days, or within 2 days)—usually in a person who has no pre-existing disease.

"Acute organ failure" refers to loss of organ function that occurs rapidly—in days or weeks (e.g., within 26 weeks, within 13 weeks, within 10 weeks, within 5 weeks, within 4 weeks, within 3 weeks, within 2 weeks, within 1 week, within 5 days, within 4 days, within 3 days, or within 2 days)—usually in a person who has no pre-existing disease. For instance, the term "acute renal failure" means a rapid deterioration in renal function sufficient to result in accumulation of waste products in the body. Acute liver failure is discussed in more detail below.

As used herein, "ischemia" refers to a reduction in blood flow to an organ.

The terms "sepsis" and "septicemia" refer to a morbid condition resulting from the invasion of the bloodstream by microorganisms and their associated endotoxins.

"Endotoxin" refers to any harmful components of microbial cells such as lipopolysaccharides from the Gram-negative bacterial cell wall, peptidoglycans from Gram-positive bacteria, and mannan from fungal cell walls.

Those of skill in the art will recognize that one or more of organ dysfunction, organ failure, and/or one or more conditions which are precursors of or associated with organ dysfunction or failure may be comorbid, i.e. may be present in a subject or individual at the same time. For example, a subject may have active sepsis that results in organ failure. Thus, preventing and/or treating may overlap in that treating sepsis may, at the same time, prevent the occurrence of organ failure; or treating ischemia may prevent or treat inflammation that occurs following an ischemic event, that would lead to organ failure but for the administration of the present compositions.

In some aspects, the present disclosure thus provides compositions and methods for preventing and/or treating the dysfunction and/or failure of one or more organs or organ systems in a subject in need thereof by administering a therapeutically effective amount of a composition as described herein. In some aspects, the organ and/or organ system dysfunction and/or failure is acute, e.g. acute liver failure.

The methods may include administering to the subject a therapeutically effective or sufficient amount of at least one composition as described herein. The amount is sufficient to prevent and/or treat dysfunction of the organ(s) being treated, or to prevent and/or treat failure of the organ(s) being treated. In some aspects, the organ failure that is treated is Multiple Organ Dysfunction Syndrome (MODS). The methods generally include identifying or diagnosing subjects who are in need of such treatment, e.g. subjects that would benefit from such treatment e.g. due to being susceptible to organ dysfunction or failure, or already exhibiting at least one sign or symptom of organ dysfunction or failure. For example, the subject may be a member of a particular patient population such as those with disease resulting from acute insult (acute organ injury resulting from bacterial infection, severe burns, trauma, etc.), or chronic conditions (long-term exposure to organ-damaging medication), and/or from other causes which are discussed in more detail below.

The patient group(s) addressed by the present disclosure can also be defined as follows. The SOFA system was created in a consensus meeting of the European Society of Intensive Care Medicine in 1994 and further revised in 1996. The SOFA is a six-organ dysfunction/failure score measuring multiple organ failure daily. Each organ is graded from 0 (normal) to 4 (the most abnormal), providing a daily score of 0 to 24 points. The objective of the SOFA is to create a simple, reliable, and continuous score for clinical staff. Sequential assessment of organ dysfunction during the first few days of intensive care unit (ICU) or hospital admission is a good indicator of prognosis. Both the mean and highest SOFA scores are particularly useful predictors of outcome.

In one aspect, the patient group pursuant to the disclosure is one having as a lower threshold at least one SOFA score, being at 1 for at least one of the clinical criteria of respiration, or liver, or coagulation, or cardiovascular, or CNS, or renal on the day of admission to hospital or Intensive Care Unit (ICU). However, the patient may also have a score of 1 or 2, or more (e.g. 3 or 4) for at least one of the clinical criteria. Thus, said patient group is in need of therapeutic intervention pursuant to the present disclosure, and thus in need for prevention or reduction of organ dysfunction or organ failure, e.g. renal, liver, heart and/or lung organ dysfunction or organ failure.

Independent of the initial score, generally an increase in SOFA score during the first 48 hours in the ICU or in the hospital predicts a mortality rate of at least 50%. Thus, in another aspect, the patient group in need of therapeutic intervention for organ dysfunction/failure in accordance with present disclosure is characterized by having at least one SOFA score increased within the initial 48 hours after admission to hospital or ICU. In some aspects, the organ, organs or organ systems which is/are subject to failure comprise at least one member of the following: cardiovascular, respiratory, renal, haematological, neurological, gastrointestinal organs, hepatic organs, heart, liver, lungs, intestines, colon, kidneys, spleen, and brain.

The present disclosure may but does not necessarily provide for a therapy of healing/curing of an underlying or comorbid disease e.g. infections, cancer, or tumors located in the respective organ, but rather for resuscitating the respective organ towards physiologic function. Accordingly, the therapy for a chronic or acute disease or acute condition of a patient within the scope of the present disclosure includes any kind of organ insufficiency, or poor organ function, e.g. as an acute event.

Kidney Dysfunction and/or Failure

Kidney disease may be acute or chronic, or even acute-on-chronic renal failure as discussed below.

Acute kidney injury (AKI, previously called acute renal failure (ARF)) refers to an abrupt loss of kidney function that develops e.g. within about 7 days. AKI generally occurs because of damage to the kidney tissue caused by decreased renal blood flow (renal ischemia) from any cause e.g. low blood pressure, exposure to substances harmful to the kidney, an inflammatory process in the kidney, or an obstruction of the urinary tract which impedes the flow of urine. Causes of acute kidney injury include accidents, injuries, or complications from surgeries in which the kidneys are deprived of normal blood flow for extended periods of time. Heart-bypass surgery is an example of one such procedure. Drug overdoses, either accidental or from chemical overloads of drugs such as antibiotics or chemotherapy, may also cause the onset of acute kidney injury. AKI is diagnosed on the basis of characteristic laboratory findings, such as elevated blood urea nitrogen (BUN) and creatinine, or inability of the kidneys to produce sufficient amounts of urine (e.g. less than 400 mL per day in adults, less than 0.5 mL/kg/h in children or less than 1 mL/kg/h in infants). Thus, the present methods may include measuring or detecting one or more of these parameters in a subject and, if one or more the measured parameters is positive and thus indicative of the presence of kidney malfunction developing within about 7 days, then diagnosing acute kidney injury and administering a composition as described herein to the subject, as described herein.

Chronic kidney disease (CKD) usually develops slowly and, initially, patients may show few symptoms. CKD can be the long term consequence of irreversible acute disease or part of a disease progression. CKD has numerous causes, including diabetes mellitus, long-term, uncontrolled hypertension, polycystic kidney disease, infectious diseases such as hantavirus, and certain genetic predisposition e.g. APOL1 gene variants. The present methods include administering a composition as described herein to a subject having CKD.

In some cases, the clinical criteria denoting the patient group(s) for kidney dysfunction/failure are as follows:

Patients at risk for kidney dysfunction/failure: GFR decrease >25%, serum creatinine increased 1.5 times or urine production of <0.5 ml/kg/hr for 6 hours Patients with present kidney injury: GFR decrease >50%, doubling of creatinine or urine production <0.5 ml/kg/hr for 12 hours Patients with kidney failure: GFR decrease >75%, tripling of creatinine or creatinine >355 µmol/l (with a rise of >44) (>4 mg/dl) or urine output below 0.3 ml/kg/hr for 24 hours Patients with loss of kidney function: persistent acute kidney injury (AKI) or complete loss of kidney function for more than 4 weeks End-stage renal disease: complete loss of kidney function for more than 3 months.

Contrast and enhancing dyes used for various types of imaging, especially iodine containing dyes, are also known to cause kidney damage, especially in susceptible populations such as the elderly, diabetics, those who already have some form of kidney impairment, etc. Contrast-induced nephropathy is defined as either a greater than 25% increase of serum creatinine or an absolute increase in serum creatinine of 0.5 mg/dL in the wake of administration of a dye e.g. for X-rays or computed tomography (CT) scans. Iodine containing dyes include but are not limited to iohexol, iodixanol and ioversol, as well as other ionic iodine dyes such as Diatrizoate (Hypaque 50), Metrizoate (Isopaque 370), and Ioxaglate (Hexabrix); and non-ionic contrast media such as Iopamidol (Isovue® 370), Iohexol (Omnipaque 350), Ioxilan (Oxilan® 350), Iopromide (Ultravist®

370), and Iodixanol (Visipaque 320). The compositions described herein can prevent or lessen the impact of such dyes when administered, for example, before administration of the dye, and/or concomitantly with the dye and/or after dye administration to maintain kidney values at a normal level in spite of exposure to the dye, or to facilitate or speed the return of those values to safe, normal ranges after dye administration.

Liver Dysfunction and/or Failure

An exemplary aspect of the present disclosure involves the treatment of acute liver failure, especially acute liver failure caused by necrosis. Acute liver failure involves the rapid development of hepatocellular dysfunction, specifically coagulopathy and mental status changes (encephalopathy) in a patient without known prior liver disease. This malady embraces a number of conditions whose common thread is severe injury of hepatocytes and/or massive necrosis e.g. loss of function of 80-90% of liver cells. Loss of hepatocyte function sets in motion a multiorgan response characterized by the rapid appearance of severe complications soon after the first signs of liver disease (such as jaundice). Complications include hepatic encephalopathy and impaired protein synthesis, e.g. as measured by the levels of serum albumin and the prothrombin time in the blood. Up to now, treatment options for acute liver failure have been limited and death often occurs suddenly, even after the liver has begun to recover from the original damage.

The diagnosis of acute liver failure (i.e. the identification of a subject experiencing acute liver failure and who could benefit from the practice of the present methods) is generally based on physical exam, laboratory findings, patient history, and past medical history to establish, for example, mental status changes, coagulopathy, rapidity of onset, and absence of known prior liver disease. The exact definition of "rapid" depends on the particular convention that is used. Different sub-divisions exist which are based on the time from onset of first hepatic symptoms to onset of encephalopathy. One scheme defines "acute hepatic failure" as the development of encephalopathy within 26 weeks of the onset of any hepatic symptoms. This is sub-divided into "fulminant hepatic failure", which requires onset of encephalopathy within 8 weeks, and "subfulminant", which describes onset of encephalopathy after 8 weeks but before 26 weeks. Another scheme defines "hyperacute" liver failure as onset within 7 days, "acute" liver failure as onset between 7 and 28 days, and "subacute" liver failure as onset between 28 days and 24 weeks. Subjects identified as experiencing acute liver failure by any of these criteria may be treated by the methods described herein.

In some cases, the patient group for liver dysfunction/failure is characterized by a lower threshold of Bilirubin of >1.2 mg/dL, such as >1.9 mg/dL, or >5.9 mg/dL. Acute liver failure has many potential causes and subjects identified as experiencing acute liver failure for any reason can be treated by the methods described herein. Possible causes include:

Acetaminophen (APAP). The most common cause of acute liver failure in the United States is acetaminophen (paracetamol, Tylenol®, etc.) overdose. Acute liver failure can occur if a single very large dose of APAP is taken all at once, or it can occur if higher-than-recommended doses are taken every day for several days. People with chronic liver disease are especially vulnerable, as are the elderly, the very young, etc. In such subjects, an APAP "overdose" may be a dose that would be a safe or normal dose for a person that does not have chronic liver disease or is not elderly or very young. This aspect of the disclosure is discussed in detail below.

Prescription medications. Some prescription medications, including antibiotics, nonsteroidal anti-inflammatory drugs and anticonvulsants, can cause acute liver failure.

Herbal supplements. Herbal drugs and supplements, including kava, ephedra, skullcap and pennyroyal, have been linked to acute liver failure.

Hepatitis and other viruses. Hepatitis A, hepatitis B and hepatitis E can cause acute liver failure. Other viruses that can cause acute liver failure include Epstein-Barr virus, cytomegalovirus and herpes simplex virus.

Toxins. Toxins that can cause acute liver failure include the poisonous wild mushroom *Amanita phalloides*, which is sometimes mistaken for edible species.

Autoimmune disease. Liver failure can be caused by autoimmune hepatitis, a disease in which the immune system attacks liver cells, causing inflammation and injury.

Diseases of the veins in the liver. Vascular diseases, such as Budd-Chiari syndrome, can cause blockages to form in the veins of the liver and lead to acute liver failure.

Metabolic disease. Rare metabolic diseases, such as Wilson's disease and acute fatty liver of pregnancy, can cause acute liver failure.

Cancer. Cancer that begins in the liver or cancer that spreads to the liver from other locations in the body can cause acute liver failure.

Other. Other causes include idiosyncratic reactions to medication (e.g. tetracycline, troglitazone), excessive alcohol intake (severe alcoholic hepatitis), Reye syndrome (acute liver failure in a child with a viral infection e.g. chickenpox in which aspirin may play a role; and others. Many cases of acute liver failure have no apparent cause.

In addition, various symptoms of liver toxicity may be prevented and/or treated by the methods and compositions of the present disclosure prior to the development of full-blown ALF. Exemplary symptoms include but are not limited to: cerebral edema and encephalopathy (which may lead to hepatic encephalopathy, coma, brain herniation, etc.); coagulopathy (e.g. prolongation in prothrombin time, platelet dysfunction, thrombocytopenia, intracerebral bleeding, etc.); renal failure (e.g. due to original insult such as APAP overdose resulting in acute tubular necrosis, or from hyperdynamic circulation leading to hepatorenal syndrome or functional renal failure); inflammation and infection (e.g. systemic inflammatory syndrome, which can lead to sepsis and multiorgan failure irrespective of the presence or absence of infection); various metabolic derangements such as hyponatremia, hypoglycemia, hypokalemia, hypophosphatemia, metabolic alkalosis, and lactic acidosis (occurring predominantly in acetaminophen overdose); hemodynamic and cardio-respiratory compromise (e.g. hypotension, decrease in tissue oxygen uptake, tissue hypoxia and lactic acidosis); pulmonary complications (e.g. acute respiratory distress syndrome (ARDS), with or without sepsis, pulmonary haemorrhage, pleural effusions, atelectasis, and intrapulmonary shunts, etc.); late pregnancy complications, for which early clinical manifestations of ALF include hypodynamia, decrease in appetite, dark amber urine, deep jaundice, nausea, vomiting, and abdominal distention, etc. Subjects exhibiting one or more of these symptoms or conditions may benefit from the administration of the 25HC3S or pharmaceutically acceptable salt thereof.

Acute Liver Failure due to APAP toxicity

In some aspects, the present disclosure provides methods and compositions for preventing and/or treating APAP associated toxicity and symptoms associated with or characteristic thereof, especially liver injury or ALF as discussed above. APAP toxicity is one of the most common causes of poisoning worldwide and in the United States and the United Kingdom it is the most common cause of acute liver failure. Many individuals with APAP toxicity may have no symptoms at all in the first 24 hours following overdose. Others may initially have nonspecific complaints such as vague abdominal pain and nausea. With progressive disease, signs of liver failure usually develop; these include low blood sugar, low blood pH, easy bleeding, and hepatic encephalopathy. Damage to the liver, or hepatotoxicity, results not from APAP itself, but from one of its metabolites, N-acetyl-p-benzoquinoneimine (NAPQI), also known as N-acetylimidoquinone. NAPQI depletes the liver's natural antioxidant glutathione and directly damages cells in the liver, leading to liver failure. Risk factors for APAP toxicity include excessive chronic alcohol intake, fasting or anorexia nervosa, and the use of certain drugs such as isoniazid.

Methods to prevent or treat ALF in a subject in need thereof, especially liver dysfunction and/or acute liver failure associated with APAP toxicity, are described in this disclosure. The methods may include administering a composition as described herein prior to administration of APAP, and/or concomitantly with administration of APAP, and/or after administration of APAP, to prevent and/or treat APAP toxicity. Compositions comprising APAP and 25HC3S or pharmaceutically acceptable salt thereof are also encompassed.

Pancreas Dysfunction and Failure

The pancreas is a glandular organ that functions in the digestive system and endocrine system of vertebrates. It produces several important hormones, including insulin, glucagon, somatostatin, and pancreatic polypeptide, and also secretes pancreatic juice containing digestive enzymes that assist digestion and absorption of nutrients in the small intestine. Inflammation of the pancreas (pancreatitis) has several causes and typically requires immediate treatment. It may be acute, beginning suddenly and lasting a few days, or chronic, occurring over many years. Eighty percent of cases of pancreatitis are caused by alcohol or gallstones, with gallstones being the single most common etiology of acute pancreatitis and alcohol being the single most common etiology of chronic pancreatitis. Severe pancreatitis is associated with organ failure, necrosis, infected necrosis, pseudocyst and abscess, having mortality rates around 2-9%, and higher where necrosis has occurred. Severe pancreatitis is diagnosed if at least three of the following are true: patient age is greater than 55 years; blood P02 oxygen is less than 60 mm Hg or 7.9 kP; white blood cells >15,000 WBCs per microliter (mcL); calcium <2 mmol/L; urea >16 mmol/L; lactate dehydrogenase (LDH) >600 iu/L; aspartate transaminase (AST) >200 iu/L; albumin <32 g/L; and glucose >10 mmol/L.

An aspect of the present disclosure is the treatment of pancreatic dysfunction and/or failure by administering a composition as described herein to a patient in need thereof. Suitable patients or patient populations are identified, by a skilled medical practitioner, as exhibiting at least one of the symptoms or criteria listed above.

Heart Dysfunction and/or Failure

Heart failure (HF), often used to mean chronic heart failure (CHF), occurs when the heart is unable to pump sufficiently to maintain blood flow to meet the needs of the body. The terms congestive heart failure (CHF) or congestive cardiac failure (CCF) are often used interchangeably with chronic heart failure. Symptoms commonly include shortness of breath (especially with exercise, when lying down, and at night while sleeping), excessive tiredness, and leg swelling. Common causes of heart failure include coronary artery disease including a previous myocardial infarction (heart attack), high blood pressure, atrial fibrillation, valvular heart disease, and cardiomyopathy. Heart failure is distinct from myocardial infarction, in which part of the heart muscle dies, and cardiac arrest, in which blood flow stops altogether.

Heart failure is typically diagnosed based on the history of the symptoms and a physical examination with confirmation by echocardiography, blood tests, and/or chest radiography. Echocardiography uses ultrasound to determine the stroke volume (SV, the amount of blood in the heart that exits the ventricles with each beat), the end-diastolic volume (EDV, the total amount of blood at the end of diastole), and the SV in proportion to the EDV, a value known as the ejection fraction (EF). Abnormalities in one or more of these may indicate or confirm heart dysfunction and/or failure. An electrocardiogram (ECG/EKG) is used to identify arrhythmias, ischemic heart disease, right and left ventricular hypertrophy, and presence of conduction delay or abnormalities (e.g. left bundle branch block). Abnormalities in one or more of these may also indicate or confirm heart dysfunction and/or failure. Blood tests routinely performed to diagnose or confirm heart dysfunction/failure include electrolytes (sodium, potassium), measures of renal function, liver function tests, thyroid function tests, a complete blood count, and often C-reactive protein if infection is suspected. Abnormalities in one or more of these may also indicate or confirm the presence of heart dysfunction and/or failure. An elevated B-type natriuretic peptide (BNP) is a specific test indicative of heart failure. If myocardial infarction is suspected, various cardiac markers may be tested, including but not limited to troponin creatine kinase (CK)-MB (an isoform of creatine kinase); lactate dehydrogenase; aspartate transaminase (AST) (also referred to as aspartate aminotransferase); myoglobin; ischemia-modified albumin (IMA); pro-brain natriuretic peptide; glycogen phosphorylase isoenzyme BB, etc. Abnormal levels of one or more of these (usually abnormally high levels) are considered as identifying a subject in need of treatment for cardiac dysfunction or failure.

Heart failure may also occur as a side effect and/or in the aftermath of chemotherapy, e.g. chemotherapy received as treatment for cancer such as breast cancer. The administration of a composition as described herein to a patient receiving or who has already received chemotherapy may prevent unwanted damage to heart (and other organs, organ systems, tissues and cells) during or after cancer chemotherapy. In other words, the composition as described herein is used as a protective agent for deleterious effects of chemotherapy.

A subject who is confirmed to have or suspected of having cardiac dysfunction or failure is treated by administration of a therapeutically effective amount of a composition as described herein, the amount being sufficient to prevent symptoms of heart dysfunction or failure, or to ameliorate symptoms of heart dysfunction or failure, e.g. to at least partially restore heart function to normal or near normal, and/or to prevent further deterioration of heart function and health of the patient.

Brain Dysfunction and/or Failure

Brain dysfunction and/or failure (i.e. organic brain syndrome "OBS") is a general term that describes decreased mental function due to a medical disease other than a psychiatric illness. Causes include but are not limited to brain injury caused by trauma; bleeding into the brain (intracerebral hemorrhage); bleeding into the space around the brain (subarachnoid hemorrhage); blood clot inside the skull causing pressure on brain (subdural hematoma); concussion; various breathing conditions such as low oxygen in the body (hypoxia) and high carbon dioxide levels in the body (hypercapnia); various cardiovascular disorders, e.g. dementia due to many strokes or multi-infarct dementia, heart infections (endocarditis, myocarditis), stroke (e.g. spontaneous stroke) and transient ischemic attack (TIA) or so-called "ministrokes"; or due to various degenerative disorders such as Alzheimer disease, Creutzfeldt-Jacob disease, diffuse Lewy Body disease, Huntington disease, multiple sclerosis, normal pressure hydrocephalus, Parkinson disease and Pick disease; dementia due to metabolic causes such as kidney, liver, or thyroid disease and/or vitamin deficiency (B1, B12, or folate); as well as drug and alcohol-related conditions e.g. alcohol withdrawal state, intoxication from drug or alcohol use, Wernicke-Korsakoff syndrome (a long-term effect of excessive alcohol consumption or malnutrition), and withdrawal from drugs (especially sedative-hypnotics and corticosteroids); and sudden onset (acute) or long-term (chronic) infections e.g. septicemia, encephalitis, meningitis, prion infections, and late-stage syphilis; as well as complications of cancer or cancer treatment. Symptoms of OBS include agitation, confusion; long-term loss of brain function (dementia), and severe, short-term loss of brain function (delirium), as well as impacts on the autonomic nervous system which controls e.g. breathing. Diagnosis or confirmation of the presence of OBS is determined by detecting or measuring various methodology such as blood tests, electroencephalogram (EEG), head CT scan, head MRI and/or lumbar puncture, for which normal values typically range as follows: pressure: 70-180 mm Hg; cerebral spinal fluid (CSF) appearance: clear, colorless; CSF total protein: 15-60 mg/100 mL; gamma globulin: 3-12% of the total protein; CSF glucose: 50-80 mg/100 mL (or greater than ⅔ of blood sugar level); CSF cell count: 0-5 white blood cells (all mononuclear), and no red blood cells; and CSF chloride: 110-125 mEq/L.

If one or more of these tests or analyses or indicia are abnormal, the subject is generally considered as susceptible to or already suffering from OBS. A subject who is confirmed to have or suspected of having OBS (either early stage or advanced) is treated by administration of a therapeutically effective amount of a composition comprising 25HC3S or pharmaceutically acceptable salt thereof, the amount being sufficient to prevent symptoms of OBS, or to ameliorate symptoms of OBS, e.g. to at least partially restore brain function to normal or near normal, and/or to prevent further deterioration of brain function and health of the patient.

Organ Dysfunction and/or Failure Due to Trauma

In some aspects, the organ dysfunction/failure is due to trauma. Examples of trauma injuries include but are not limited to: wounds resulting from vehicular accidents; gunshot wounds (both accidental during hunting associated activities, and intentionally inflicted such as those associated with criminal activity or war); blunt trauma or blunt injury e.g. non-penetrating blunt force trauma such as physical trauma to a body part e.g. by impact, injury or physical attack, etc. Examples of blunt trauma include but are not limited to: concussion, e.g. concussion suffered by athletes or by persons involved in accidents, falls, etc., and blunt trauma suffered as the result of an encounter with a projectile such as a falling object, and others.

Individuals who are susceptible to such blunt trauma (e.g. athletes, the elderly) may benefit from prophylactic administration of a composition as described herein, and if blunt trauma such as a concussion is diagnosed in a subject, the subject will benefit by administration as soon as possible after the injury is suspected or confirmed.

Prevention and/or Treatment of Conditions Caused by Ischemia

Ischemia refers to an insufficient supply of blood to a tissue or organ, causing a shortage of oxygen and glucose needed for cellular metabolism and to keep tissue alive. Hypoxia (also known as hypoxiation or anoxemia) is caused by ischemia and refers to the condition in which the body or a region of the body is deprived of adequate oxygen supply. Ischemia results in tissue damage in a process known as the ischemic cascade. Damage is largely the result of the build-up of metabolic waste products, the inability to maintain cell membranes, mitochondrial damage, and eventual leakage of autolyzing proteolytic enzymes into the cell and surrounding tissues. Ensuing inflammation also damages cells and tissues. Without immediate intervention, ischemia may progress quickly to tissue necrosis, and ultimately to, for example, organ dysfunction or failure.

In addition, restoration of blood supply to ischemic tissues can cause additional damage known as reperfusion injury. Reperfusion injury can be more damaging than the initial ischemia. Reintroduction of blood flow brings oxygen back to the tissues, causing a greater production of free radicals and reactive oxygen species that damage cells. It also brings more calcium ions to the tissues, which may cause calcium overloading and can result in potentially fatal cardiac arrhythmias, and which may accelerate cellular self-destruction. The restored blood flow may also exaggerate the inflammation response of damaged tissues, causing white blood cells to destroy damaged but still viable cells.

The present disclosure provides methods and compositions for preventing and/or treating the untoward effects or outcomes of ischemia, including ischemia/reperfusion injury, in a subject in need thereof. The methods generally comprise administering a therapeutically effective amount of a composition as described herein sufficient to prevent or treat symptoms of ischemia and/or ischemia/reperfusion. The methods may also include identifying or diagnosing a subject who will experience, or is experiencing or who has experienced ischemia and/or ischemia/reperfusion. The ischemia and/or ischemia/reperfusion may be due to a disease process (e.g. atherosclerosis, a blood clot, etc.), or due to an accident (e.g. severing of an artery or other blood conduit), or may be intentional (planned), e.g. as occurs during some heart or other surgeries in order to temporarily stop blood flow to a defined or circumscribed region of the body.

Types of ischemia that are relevant to the methods described herein include but are not limited to:

Cardiac ischemia, e.g., myocardial ischemia, occurring when the heart muscle, or myocardium, receives insufficient blood flow. This most frequently results from atherosclerosis, which is the long-term accumulation of cholesterol-rich plaques in coronary arteries.

Bowel ischemia: Both large and small bowel can be affected by ischemic injury. Ischemic injury of the large intestine may result in an inflammatory process known as ischemic colitis and also as a result of surgery and adhesion development. Ischemia of the small bowel is called mesenteric ischemia.

Brain ischemia is insufficient blood flow to the brain, and can be acute (i.e., rapid) or chronic (i.e., long-lasting). Acute ischemic stroke is a neurologic emergency that may be reversible if treated rapidly. Chronic ischemia of the brain may result in a form of dementia called vascular dementia.

A brief episode of ischemia affecting the brain is called a transient ischemic attack (TIA), often erroneously referred to as a "mini-stroke".

Limb ischemia: Lack of blood flow to a limb results in acute limb ischemia.

Cutaneous ischemia refers to reduced blood flow to the skin layers, which may result in mottling or uneven, patchy discoloration of the skin, and may lead to the development of cyanosis, or other conditions such as pressures sores (e.g. decubitus ulcers, bedsores, etc.).

Reversible ischemia refers to a condition which results in a lack of blood flow to a particular organ which can be reversed through use of medications or surgery. It most often refers to hindered blood flow to the heart muscle, but it can refer to an obstruction blocking any organ in the body, including the brain. Whether or not a case of ischemia can be reversed will depend on the underlying cause. Plaque buildup in the arteries, weakened arteries, low blood pressure, blood clots, and unusual heart rhythms can all be causes of reversible ischemia.

Apical ischemia refers to lack of blood flow to the apex or bottom tip of the heart.

Mesenteric ischemia refers to inflammation and injury of the small intestine occurs due to inadequate blood supply. Causes of the reduced blood flow can include changes in the systemic circulation (e.g. low blood pressure) or local factors such as constriction of blood vessels or a blood clot.

Ischemia of various organs, including but not limited to liver (hepatic ischemia), kidney, intestines, etc.

Ischemia, ischemia/reperfusion may also be causally related to inflammation and organ dysfunction/failure. For example, cerebral (brain) ischemia is typically accompanied by a marked inflammatory reaction that is initiated by ischemia-induced expression of cytokines, adhesion molecules, and other inflammatory mediators, including prostanoids and nitric oxide. It is known that interventions aimed at attenuating such inflammation reduce the progression of brain damage that occurs e.g. during the late stages of cerebral ischemia. In addition, the most frequent cause of intrarenal (kidney) failure (ARF) is transient or prolonged renal hypoperfusion (ischemia).

Other types of ischemia, the effects of which can be treated or prevented as described herein, include but are not limited to: ischemic stroke, small vessel ischemia, ischemia/reperfusion injuries, etc.

Diagnosis of ischemia is generally carried out by identifying one or more symptoms of malfunction in the particular organ or organ system or tissue or cell that is affected. Thus, symptoms include those listed herein for dysfunction/failure of individual organs, plus documentation of ischemia per se, such as by noting the history of the patient (e.g. known occlusion, blockage or severance of an artery that otherwise supplies blood to the organ or tissue, imaging which shows or is consistent with such observations, etc.).

If one or more suitable tests or analyses or indicia are abnormal, the subject is generally considered as susceptible to or already suffering from ischemia. A subject who is confirmed to have or suspected of having ischemia (or is known to be undergoing future planned ischemia, e.g. during a surgical procedure) may be treated by administration of a therapeutically effective amount of a composition as described herein, the amount being sufficient to prevent symptoms of ischemia and/or ischemia-reperfusion injury, or to ameliorate symptoms of ischemia and/or ischemia-reperfusion injury, e.g. to at least partially restore organ or tissue function to normal or near normal when blood flow is reestablished, and/or to prevent further deterioration of organ or tissue function and health of the patient.

Prevention and/or Treatment of Effects of Unwanted Cell Death

Active, regulated cell death is referred to as "programmed cell-death" or "PCD" and is a regulated process mediated by intracellular pathways. While PCD is generally beneficial to an organism, aberrations in signaling or the presence of overwhelming stresses on the cell may cause undesirable PCD to occur. The forms of PCD include apoptosis, the initiation of controlled intracellular signaling in response to a stress, which brings about cell suicide; and necroptosis, a form of PCD that serves as a backup to apoptosis, e.g. when the apoptosis signaling is blocked by endogenous or exogenous factors such as viruses or mutations.

In contrast to PCD, necrosis refers to unregulated, passive cell death which results in the harmful, premature death of cells in living tissue. Necrosis is typically caused by factors external to the cell or tissue, such as infection, toxins, trauma, ischemia, etc. Without being bound by theory, it is believed that necrosis involves the loss of cell membrane integrity and an uncontrolled release of products of cell death into the intracellular space, thereby initiating an inflammatory response in the surrounding tissue which prevents nearby phagocytes from locating and eliminating the dead cells by phagocytosis. While surgical removal of necrotic tissue can halt the spread of necrosis, in some cases surgical intervention is not possible or practical e.g. when internal tissues or organs are involved. Thus, necrosis of internal organs often leads to dangerous and often deadly organ dysfunction and/or failure.

The present disclosure provides methods and compositions for preventing and/or treating the effects of unwanted cell death in a subject in need thereof, especially unwanted apoptosis and necrosis associated with organ dysfunction and/or organ failure. The cell death may result from or be associated with unwanted PCD (e.g. unwanted or deleterious apoptosis, autophagy, or necroptosis) or with necrosis, which is unwanted by definition; and/or combinations of these. The methods comprise administering a therapeutically effective amount of a composition as described herein, the amount being sufficient to prevent unwanted cell death from occurring, or to treat the effects of unwanted cell death that has already occurred in a subject.

Unwanted or deleterious cell death via apoptosis occurs, for example, in the aftermath of ischemia and in Alzheimer's disease. Unwanted apoptosis is extremely harmful, causing extensive tissue damage.

Types of necrosis that may be prevented and/or treated by the methods described herein include but are not limited to:

Aseptic necrosis is necrosis without infection, usually in the head of the femur after traumatic hip dislocation.

Acute tubular necrosis refers to acute renal failure with mild to severe damage or necrosis of tubule cells, usually secondary to either nephrotoxicity, ischemia after major surgery, trauma (crush syndrome), severe hypovolemia, sepsis, or burns.

Avascular necrosis is the consequence of temporary or permanent cessation of blood flow to the bones. The absence of blood causes the bone tissue to die, resulting in fracture or collapse of the entire bone.

Balser's fatty necrosis is gangrenous pancreatitis with omental bursitis and disseminated patches of necrosis of fatty tissues.

Bridging necrosis is necrosis of the septa of confluent necrosis bridging adjacent central veins of hepatic lobules and portal triads characteristic of subacute hepatic necrosis.

Caseous or "cheesy" necrosis is necrosis in which the tissue is soft, dry, and cottage cheese-like, most often seen in tuberculosis and syphilis; in contrast to moist necrosis in which the dead tissue is wet and soft.

Central necrosis is necrosis affecting the central portion of an affected bone, cell or lobule of the liver.

Coagulation necrosis refers to necrosis of a portion of an organ or tissue, with formation of fibrous infarcts, the protoplasm of the cells becoming fixed and opaque by coagulation of the protein elements, the cellular outline persisting for a long time.

Colliquative or liquefaction necrosis is that in which the necrotic material becomes softened and liquefied.

Contraction band necrosis refers to a cardiac lesion characterized by hypercontracted myofibrils and contraction bands, and mitochondrial damage caused by calcium influx into dying cells resulting in arrest of the cells in the contracted state.

Fat necrosis is that in which the neutral fats in adipose tissue are broken down into fatty acids and glycerol, usually affecting the pancreas and peripancreatic fat in acute hemorrhagic pancreatitis.

Gangrenous necrosis is that in which ischemia combined with bacterial action causes putrefaction to set in. "Gangrene" includes dry gangrene, wet gangrene, gas gangrene, internal gangrene and necrotizing fasciitis.

Gingival necrosis refers to the death and degeneration of the cells and other structural elements of the gingivae (e.g., necrotizing ulcerative gingivitis).

Interdental necrosis is a progressive disease that destroys the tissue of the papillae and creates interdental craters. Advanced interdental necrosis leads to a loss of periodontal attachment.

Ischemic necrosis refers to death and disintegration of a tissue resulting from interference with its blood supply, thus depriving the tissues of access to substances necessary for metabolic sustenance.

Macular degeneration: Macular degeneration (both wet and dry forms) occurs when the small central portion of the retina, known as the macula, deteriorates. Because the disease develops as a person ages, it is often referred to as age-related macular degeneration (AMD).

Massive hepatic necrosis refers to massive, usually fatal, necrosis of the liver, a rare complication of viral hepatitis (fulminant hepatitis) that may also result from exposure to hepatotoxins or from drug hypersensitivity.

Phosphorus necrosis is necrosis of the jaw bone due to exposure to phosphorus.

Postpartum pituitary necrosis refers to necrosis of the pituitary during the postpartum period, often associated with shock and excessive uterine bleeding during delivery, and leading to variable patterns of hypopituitarism.

Radiation necrosis is the death of tissue caused by radiation.

Selective myocardial cell necrosis refers to myofibrillar degeneration.

Zenker's necrosis refers to hyaline degeneration and necrosis of striated muscle; also called Zenker's degeneration.

Such unwanted or pathological cell death may be prevented or treated by contacting affected cells with a composition as described herein in an amount sufficient to prevent or treat death of the cells, and/or to prevent the spread of cell death signaling to adjacent cells. Candidate cells for treatment, or organs containing candidate cells for treatment, are identified by any of several known techniques, e.g. by observation of overt effects of cell death (tissue breakdown, liquefaction, odor, etc.), detecting release of lactate dehydrogenase (LDH), by various scans such as tomography or nuclear magnetic resonance, by detecting the presence of causative bacteria (e.g. using PCR), using antibodies, etc.

Prevention and/or Treatment of Symptoms Related to or Caused by Sepsis (Inflammatory Response Syndrome, or Sirs)

Sepsis is a potentially life-threatening whole-body inflammation caused by a serious infection which triggers an immune response. The infection is typically caused by bacteria, but can also be due to fungi, viruses, or parasites in the blood, urinary tract, lungs, skin, or other tissues. Unfortunately, symptoms can continue even after the infection is gone. Severe sepsis is sepsis causing poor organ function or insufficient blood flow as evidenced e.g. by low blood pressure, high blood lactate, and/or low urine output. In fact, sepsis is considered to fall within a continuum from infection to multiple organ dysfunction syndrome (MODS). Septic shock is low blood pressure due to sepsis that does not improve after reasonable amounts of intravenous fluids are given.

Up to now, sepsis was typically treated with intravenous fluids and antibiotics, often in an intensive care unit. Various medications and other interventions may be used, e.g. mechanical ventilation, dialysis, and oxygen saturation may also be used. Outcomes depend on the severity of disease with the risk of death from sepsis being as high as 30%, severe sepsis as high as 50%, and septic shock as high as 80%. Provided herein are methods of preventing or treating sepsis by administering to a subject or patient in need thereof, a therapeutically effective amount of a composition as described herein. For instance, the present disclosure includes the treatment of mammalian endotoxemia and septicemia and renal and mesenteric vasoconstriction that is induced by catecholamines that are used to treat endotoxemia and septic shock. The term "endotoxemia" refers to the presence of microbial endotoxins in the bloodstream. Subjects inflicted with endotoxemia usually also have septicemia. The present disclosure includes a method for treating septicemia/endotoxemia. The present disclosure also includes a method for treating acute renal failure caused by septicemia/endotoxemia by administering an effective amount of a composition described herein.

Further, the present disclosure includes a method for treating renal vasoconstriction caused by septicemia/endotoxemia. Still further, the present disclosure provides a method for attenuating catecholamine-induced renal and mesenteric vasoconstriction. Yet further, the present disclosure includes a method to prevent damage to a patient's intestines and kidney due to the effects of endotoxin and/or vasopressor agents. Sepsis is associated with mitochondrial dysfunction, which leads to impaired oxygen consumption and may lead to sepsis-induced multiple organ failure. This holds especially true for raised tissue oxygen tensions in septic patients, suggesting reduced ability of the organs to use oxygen. Because ATP production by mitochondrial oxidative phosphorylation accounts for more than 90% of total oxygen consumption, mitochondrial dysfunction may directly results in organ failure, possibly due to nitric oxide, which is known to inhibit mitochondrial respiration in vitro and is produced in excess in sepsis. Therefore, in a specific embodiment of the present disclosure, the compositions described herein are used in methods of prevention for organ dysfunction and failure in Systemic Inflammatory Response-Syndrome (SIRS), sepsis, severe sepsis, and septic shock patients.

The methods may include identifying a suitable patient in need of such treatment, e.g. by detecting or measuring at least one symptom of sepsis, e.g. abnormal temperature (body temperature above 101 F (38.3 C, "fever") or below 96.8 F (36 C), increased heart rate, increased breathing rate, probable or confirmed infection, and possibly confusion. Patients with severe sepsis exhibit at least one of the following signs and symptoms, which indicate an organ may be failing: significantly decreased urine output, abrupt change in mental status, decrease in platelet count, difficulty breathing, abnormal heart pumping function, and abdominal pain. A diagnosis of septic shock is generally based on observing the signs and symptoms of severe sepsis plus measuring extremely low blood pressure that does not adequately respond to simple fluid replacement. In some cases, a subject may be a candidate for prophylactic or therapeutic treatment of sepsis based on cough/sputum/chest pain; abdominal pain/distension/diarrhea; line infection; endocarditis; dysuria; headache with neck stiffness; cellulitis/wound/joint infection; and/or positive microbiology for any infection. In other cases, a subject may be a candidate for prophylactic or therapeutic treatment with 25HC3S or pharmaceutically acceptable salt thereof of severe sepsis based on a diagnosis of sepsis and at least one clinical suspicion of any organ dysfunction selected from: blood pressure systolic <90/mean; <65 mm HG; lactate >2 mmol/L; Bilirubin >34 µmol/L; urine output <0.5 mL/kg/h for 2 h; creatinine >177 µmol/L; platelets <100×10$^9$/L; and SpO$_2$>90% unless O$_2$ given. In some cases, a subject may be a candidate for prophylactic or therapeutic treatment of septic shock if there is refractory hypotension that does not respond to treatment and intravenous systemic fluid administration alone is insufficient to maintain a patient's blood pressure from becoming hypotensive. Patients with a diagnosis of (exhibiting signs of) early sepsis, severe sepsis or septic shock are candidates for treatment with a composition as described herein, e.g. by administration of a therapeutically effective amount of the composition. The amount administered may be sufficient to prevent symptoms of sepsis from developing or continuing, or to at least lessen the impact of symptoms of sepsis.

Hyperlipidemia

In some aspects, the subjects treated by the compositions and methods described herein have symptoms of and/or have been diagnosed with high levels of lipids i.e. hyperlipidemia. Hyperlipidemias are also classified according to which types of lipids are elevated, that is hypercholesterolemia, hypertriglyceridemia or both in combined hyperlipidemia. Elevated levels of lipoprotein (a) is also included. Hypercholesterolemia generally refers to cholesterol levels in serum in the range of about 200 mg/dl or more. Hypertriglyceridemia is characterized, for example as borderline (150 to 199 mg per dL), or high (200 to 499 mg per dL) or very high (500 mg per dL or greater). These conditions are treated by the compositions described herein, as are diseases or conditions associated therewith e.g. atherosclerosis, heart disease, stroke, Alzheimer's, gallstone diseases, cholestatic liver diseases, pancreatitis, etc. The compositions disclosed herein are used to lower cholesterol and/or lipid levels in the subject. By "lowering cholesterol levels" we mean that the level of free serum cholesterol in a patient is decreased by at least about 10% to 30%, and preferably at least about 30 to 50%, and more preferably at least about 50 to 70%, and most preferably at least about 70 to about 100%, or more, in comparison to the level of cholesterol in the subject prior to administration of the composition. Alternatively, the extent of the decrease may be determined by comparison to a similar untreated control population to whom the compound is not administered. Those of skill in the art are familiar with such determinations, e.g. the use of controls, or the measurement of cholesterol levels in the blood before and after administration of an agent that lowers cholesterol and/or lipids.

In some aspects, the disease or condition that is prevented or treated is or is caused by hyperlipidemia. By "hyperlipidemia" we mean a condition of abnormally elevated levels of any or all lipids and/or lipoproteins in the blood. Hyperlipidemia includes both primary and secondary subtypes, with primary hyperlipidemia usually being due to genetic causes (such as a mutation in a receptor protein), and secondary hyperlipidemia arising from other underlying causes such as diabetes. Lipids and lipid composites that may be elevated in a subject and lowered by the treatments described herein include but are not limited to chylomicrons, very low-density lipoproteins, intermediate-density lipoproteins, low-density lipoproteins (LDLs) and high-density lipoproteins (HDLs). In particular, elevated cholesterol (hypercholesterolemia) and triglycerides (hypertriglyceridemia) are known to be risk factors for blood vessel and cardiovascular disease due to their influence on atherosclerosis. Lipid elevation may also predispose a subject to other conditions such as acute pancreatitis. The methods of the disclosure thus may also be used in the treatment or prophylaxis (e.g. prophylactic treatment) of conditions that are or are associated with elevated lipids. Such conditions include, for example, but are not limited to: hyperlipidemia, hypercholesterolemia, hypertriglyceridemia, fatty liver (hepatic steatosis), metabolic syndrome cardiovascular diseases, coronary heart disease, atherosclerosis (i.e. arteriosclerotic vascular disease or ASVD) and associated maladies, acute pancreatitis, various metabolic disorders, such as insulin resistance syndrome, diabetes, polycystic ovary syndrome, fatty liver disease, cachexia, obesity, arteriosclerosis, stroke, gall stones, inflammatory bowel disease, inherited metabolic disorders such as lipid storage disorders, and the like. In addition, various conditions associated with hyperlipidemia include those described in issued U.S. Pat. No. 8,003,795 (Liu, et al) and U.S. Pat. No. 8,044,243 (Sharma, et al), the complete contents of both of which are hereby incorporated by reference in entirety.

In some aspects, the diseases and conditions that are prevented or treated include inflammation, and/or diseases and conditions associated with, characterized by or caused by inflammation. These include a large group of disorders which underlie many human diseases. In some embodiments, the inflammation is acute, resulting from e.g. an infection, an injury, etc. In other embodiments, the inflammation is chronic. In some embodiments, the immune system is involved with the inflammatory disorder as seen in both allergic reactions and some myopathies. However, various non-immune diseases with etiological origins in inflammatory processes may also be treated, including cancer, atherosclerosis, and ischemic heart disease, as well as others listed below.

Examples of disorders associated with abnormal inflammation which may be prevented or treated using 25HC3S or pharmaceutically acceptable salt thereof include but are not limited to: acne vulgaris, asthma, various autoimmune diseases, Celiac disease, chronic prostatitis, glomerulonephritis, various hypersensitivities, inflammatory bowel diseases, pelvic inflammatory disease, reperfusion injury, rheumatoid arthritis, sarcoidosis, transplant rejection, vasculitis, and interstitial cystitis. Also included are inflammation disorders that occur as a result of the use of both legally prescribed and illicit drugs, as well as inflammation triggered by negative cognitions or the consequences thereof, e.g. caused by stress, violence, or deprivation.

In one aspect, the inflammatory disorder that is prevented or treated is an allergic reaction (type 1 hypersensitivity), the result of an inappropriate immune response that triggers inflammation. A common example is hay fever, which is caused by a hypersensitive response by skin mast cells to allergens. Severe inflammatory responses may mature into a systemic response known as anaphylaxis. Other hypersensitivity reactions (type 2 and type 3) are mediated by antibody reactions and induce inflammation by attracting leukocytes which damage surrounding tissue, and may also be treated as described herein.

In other aspects, inflammatory myopathies are prevented or treated. Such myopathies are caused by the immune system inappropriately attacking components of muscle, leading to signs of muscle inflammation. They may occur in conjunction with other immune disorders, such as systemic sclerosis, and include dermatomyositis, polymyositis, and inclusion body myositis.

In one aspect, the methods and compositions of the disclosure are used to prevent or treat systemic inflammation such as that which is associated with obesity, such as inflammation associated with metabolic syndrome and diabetes (e.g. type 2 adult onset diabetes). In such inflammation, the processes involved are identical to tissue inflammation, but systemic inflammation is not confined to a particular tissue but involves the endothelium and other organ systems. Systemic inflammation may be chronic, and is widely observed in obesity, where many elevated markers of inflammation are observed, including: IL-6 (interleukin-6), IL-8 (interleukin-8), IL-18 (interleukin-18), TNF-α (tumor necrosis factor-alpha), CRP (C-reactive protein), insulin, blood glucose, and leptin. Conditions or diseases associated with elevated levels of these markers may be prevented or treated as described herein. In some embodiments, the inflammation may be classified as "low-grade chronic inflammation" in which a two- to threefold increase in the systemic concentrations of cytokines such as TNF-α, IL-6, and CRP is observed. Waist circumference also correlates significantly with systemic inflammatory responses; a predominant factor in this correlation is due to the autoimmune response triggered by adiposity, whereby immune cells "mistake" fatty deposits for infectious agents such as bacteria and fungi. Systemic inflammation may also be triggered by overeating. Meals high in saturated fat, as well as meals high in calories have been associated with increases in inflammatory markers, and the response may become chronic if the overeating is chronic.

Implementation of the methods of the disclosure will generally involve identifying patients suffering from or at risk for developing conditions associated with high cholesterol and/or lipids, and administering the composition of the present disclosure in an acceptable form by an appropriate route. The exact dosage to be administered may vary depending on the age, gender, weight and overall health status of the individual patient, as well as the precise etiology of the disease. However, in general for administration in mammals (e.g. humans), dosages (in terms of the 25HC3S or pharmaceutically acceptable salt thereof) in the range of from about 0.1 to about 100 mg or more of compound per kg of body weight per 24 hr., and preferably about 0.1 to about 50 mg of compound per kg of body weight per 24 hr., and more preferably about 0.1 to about 10 mg of compound per kg of body weight per 24 hr. are effective.

Liver Disorders

The liver is responsible for the maintenance of lipid homeostasis in the body, and the compositions described herein may be used prevent and treat liver disease and damage of the liver per se (e.g. NAFLD), and to prevent and treat diseases associated with excessively high levels of circulating lipids, i.e. to prevent or treat hyperlipidemia and associated disorders such as atherosclerosis. In some aspects, the subjects treated by the compositions and methods described herein have at least one symptom of or have been diagnosed with non-alcoholic fatty liver disease (NAFLD) and/or nonalcoholic steatohepatitis (NASH).

In further aspects, the subjects treated by the compositions and methods described herein have at least one symptom of and/or have been diagnosed with a liver disorder such as hepatitis, inflammation of the liver, caused mainly by various viruses but also by some poisons (e.g. alcohol); autoimmunity (autoimmune hepatitis) or hereditary conditions; non-alcoholic fatty liver disease, a spectrum in disease, associated with obesity and characterized by an abundance of fat in the liver, which may lead to hepatitis, i.e. steatohepatitis and/or cirrhosis; cirrhosis, i.e. the formation of fibrous scar tissue in the liver due to replacing dead liver cells (the death of liver cells can be caused, e.g. by viral hepatitis, alcoholism or contact with other liver-toxic chemicals); haemochromatosis, a hereditary disease causing the accumulation of iron in the body, eventually leading to liver damage; cancer of the liver (e.g. primary hepatocellular carcinoma or cholangiocarcinoma and metastatic cancers, usually from other parts of the gastrointestinal tract); Wilson's disease, a hereditary disease which causes the body to retain copper; primary sclerosing cholangitis, an inflammatory disease of the bile duct, likely autoimmune in nature; primary biliary cirrhosis, an autoimmune disease of small bile ducts; Budd-Chiari syndrome (obstruction of the hepatic vein); Gilbert's syndrome, a genetic disorder of bilirubin metabolism, found in about 5% of the population; glycogen storage disease type II; as well as various pediatric liver diseases, e.g. including biliary atresia, alpha-1 antitrypsin deficiency, alagille syndrome, and progressive familial intrahepatic cholestasis, etc. In addition, liver damage from trauma may also be treated, e.g. damage caused by accidents, gunshot wounds, etc. Further, liver damage caused by certain medications may be prevented or treated, for example, drugs such as the antiarrhythmic agent amiodarone, various antiviral drugs (e.g. nucleoside analogues), aspirin (rarely as part of Reye's syndrome in children), corticosteroids, methotrexate, tamoxifen, tetracycline, etc. are known to cause liver damage.

In other aspects, the disclosure involves a method for promoting liver cell proliferation or liver tissue regeneration in a subject, comprising administering a composition as described herein to a subject in need of at least one of liver cell proliferation and liver tissue regeneration, in order to promote proliferation of liver cells or regeneration of liver tissue in the subject. In some aspects, administration is performed before, during or after liver surgery in the subject, for example, liver transplant surgery. The subject may also have at least one of cirrhosis, liver injury, and hepatitis.

Leptin Deficiency, Leptin Resistance and Lipid Storage Disease

The present disclosure also provides compositions and methods for the treatment of disorders characterized by abnormal lipid accumulation (LA). Administration of a composition as described herein to mammals which have existing abnormal, harmful deposits of lipids (e.g. lipid globules in liver or other organs or tissues wherein deposition is inappropriate), results in a decrease or elimination of the lipid deposits and the prevention of additional lipid accumulation. Thus, administration prevents abnormal lipid deposition and reverses lipid deposition (accumulation) that is extant when treatment begins.

Disorders that are so-treated are referred to herein by phrases such as "lipid accumulation disorders", "lipid deposition disorders", etc. and include but are not limited to:
I. disorders which result from a lack or attenuation of leptin activity, due to, for example,
  i) a genetic mutation that causes low levels of leptin production, or production of a non- or poorly functioning leptin molecule, such as occurs in leptin deficiency (LD); or
  ii) a defect in leptin signaling, caused by e.g. a congenital or acquired abnormality or deficiency in the functioning of the leptin receptor, e.g. due to a genetic mutation of the leptin receptor, or due to an acquired loss of receptor sensitivity to leptin binding such as that which occurs in leptin resistance (LR); and
II. Lipid Storage Disorders, which are Generally Congenital.

The term "attenuated leptin activity" as used herein thus embraces leptin deficiency (LD) and leptin resistance (LR) as characterized in i) and ii) above. Similarly, the term "leptin-deficiency associated lipid accumulation" as used herein embraces lipid accumulation associated with leptin deficiency (LD) and leptin resistance (LR), as characterized in i) and ii) above.

Thus, subjects treated by the compositions and methods described herein may have at least one symptom of leptin deficiency and/or leptin resistance and/or a lipid storage disease. These subjects may or may not have i) a genetic mutation that causes low levels of leptin production, or production of a non- or poorly functioning leptin molecule, such as occurs in leptin deficiency (LD) (e.g. a mutation in the LEP gene encoding leptin); or ii) a defect in leptin signaling, caused by e.g. a congenital or acquired abnormality or deficiency in the functioning of the leptin receptor, e.g. due to a genetic mutation of the leptin receptor, (e.g. mutations in the Ob (lep) gene that encodes the leptin receptor) or due to an acquired loss of receptor sensitivity to leptin binding such as that which occurs in leptin resistance (LR); or iii), a lipid storage disorder, which may be congenital. Lipid storage disorders include, for example, neutral lipid storage disease, Gaucher disease, Niemann-Pick disease, Fabry disease, Farber's disease, gangliosidoses such as GM1 gangliosidoses and GM2 gangliosidoses (e.g. Tay-Sachs disease and Sandhoff disease), Krabbe disease, metachromatic leukodystrophy (MLD, including late infantile, juvenile, and adult MLD), and acid lipase deficiency disorders such as Wolman's disease and cholesteryl ester storage disease.

The methods involve administering an amount of a composition as described herein that is a therapeutically effective to prevent or treat the disease or condition.

Skin Inflammation

In yet further aspects, subjects who are treated with the compositions and methods described herein have been diagnosed with an "inflammatory skin disease" or an "inflammatory skin disorder" and/or are afflicted with one or more skin lesions. Inflammatory skin diseases are typically characterized by, for example, reddened, itchy, dry, rough, flaky, inflamed, and irritated skin, and the skin may also exhibit blisters, scaly plaques, etc. In some aspects, the inflammatory skin disease is acute, generally resolving within days or weeks even if untreated, and the compositions and methods of the disclosure ameliorate symptoms during disease resolution (e.g. lessen itching, redness, etc.) and/or hasten the disappearance of symptoms. Alternatively, in some aspects, the skin inflammatory disease/disorder is chronic, e.g. without treatment, or even with conventional treatment, symptoms persist for weeks, months, or years, or even indefinitely. In some aspects, the compositions and methods of the disclosure ameliorate (provide relief from) symptoms of chronic skin inflammation while the disease persists (e.g. lessening itching, redness, cracking and flaking of skin, etc.) and/or also partially or completely cure (cause the complete or nearly complete disappearance of) symptoms which would otherwise be present.

"Inflammatory skin diseases" is intended to encompass diseases and conditions caused by exposure to specific, known or identifiable etiological agents, and also diseases/conditions whose causes are less well-defined, e.g. they are due to an immune disorder or malfunction (e.g. an autoimmune reaction), to stress, to an unidentified allergy, to a genetic predisposition, etc., and/or are due to more than one factor.

A "skin lesion" as used herein refers most generally to an area of the skin that has abnormal growth or appearance compared to the skin around it. For example, the area of the skin may be one exhibiting a breach of one or more of the outer skin layers (at least the epidermis, and possibly the dermis and/or subcutis (hypodermis) which exposes underlying tissue. Skin lesions include, for example, skin ulcers i.e. a local defect, breakdown or excavation of the surface of the skin produced by sloughing of necrotic inflammatory tissue. Ulcers may be, for example, neurotrophic or ischemic in nature, including decubitus ulcers, diabetic ulcers, (which are frequently foot ulcers), etc. The treatment of venous and arterial ulcers, typically of the leg or foot, is also encompassed. Skin lesions also include those caused by deliberate or accidental breaches, e.g. cuts, scratches, incisions, etc., with or without accompanying inflammation or infection. A skin lesion may also be referred to as a sore, open sore, etc. The underlying cause of a skin lesion may be inflammation, infection (e.g. viral or bacterial infection), neuropathy, ischemia, necrosis (e.g. as occurs in diabetic ulcers), or a combination of one or more of these. In addition, many skin diseases are caused by and/or characterized by both inflammation and one or more skin lesions, and all such skin diseases and/or lesions, or symptoms thereof, can be treated by the compositions and methods disclosed herein.

For the avoidance of doubt, skin lesion includes skin necrosis. Thus, the methods and techniques described herein are suitable for treating or prophylactically treating skin necrosis.

Inflammatory skin diseases/disorders (particularly chronic inflammatory skin diseases), include but are not limited to, for example: atopic dermatitis, all types of psoriasis, acne, ichthyosis, contact dermatitis, eczema, photodermatoses, dry skin disorders, herpes simplex, zoster (shingles), sunburn (e.g., severe sunburn), etc. References herein to psoriasis refer to all types of psoriasis unless otherwise specified.

In some aspects, the disease/condition that is treated is psoriasis, including all types of psoriasis such as plaque flexural, guttate, pustular, nail, photosensitive, and erythrodermic psoriasis. Psoriasis is generally recognized as an immune disorder and may be triggered by or associated with factors such as infection (e.g. strep throat or thrush), stress, injury to skin (cuts, scrapes, bug bites, severe sunburns), certain medications (including lithium, antimalarials, quinidine, indomethacin), etc. and may be comorbid with other immune conditions such as Crohn's disease, type 2 diabetes, cardiovascular disease, high blood pressure, high cholesterol, depression, ulcerative colitis, etc. Psoriasis due to any of these causes, or any other cause or an unknown cause, may be treated by the formulations and methods described herein.

In some aspects, the disease/condition that is treated is eczema. Eczema is a general term used to describe a variety of conditions that cause an itchy, inflamed skin rash, and refers to any superficial inflammatory process involving primarily the epidermis, marked early by redness, itching, minute papules and vesicles, weeping, oozing, and crusting, and later by scaling, lichenification, and often pigmentation. Various types of eczema are known, including asteatotic eczema, eczema herpeticum, nummular eczema, neurodermatitis, xerotic eczema erythema (dry scaling, fine cracking, and pruritus of the skin, occurring chiefly during the winter when low humidity in heated rooms causes excessive water loss from the stratum corneum), and atopic dermatitis.

Atopic dermatitis, a form of eczema, is a non-contagious disorder characterized by chronically inflamed skin and sometimes intolerable itching. Atopic dermatitis refers to a wide range of diseases that are often associated with stress and allergic disorders that involve the respiratory system, like asthma and hay fever. Although atopic dermatitis can appear at any age, it is most common in children and young adults, e.g. infantile eczema. Characterized by skin that oozes and becomes encrusted, infantile eczema most often occurs on the face and scalp. In one aspect, the atopic dermatitis is contact allergic dermatitis, caused, for example, by exposure to an agent that causes an allergic reaction. Common triggers of atopic dermatitis include, for example, soap and household cleaners (e.g. all-purpose cleaners, dish detergents, laundry detergent, window cleaners, furniture polish, drain cleaners, toilet disinfectants, etc.); clothing (e.g. rough fabrics like wool); heat; contact with latex; cosmetics and ingredients of cosmetics (e.g. ascorbic acid, paraban preservatives, and alpha hydroxy acids such as glycolic acid, malic acid, and lactic acid); oils from plants such as poison ivy, poison oak, and poison sumac; contact with foods, especially acidic foods or spices; nickel, a common component of costume jewelry, watchbands, zippers, etc.; sunscreen and ingredients thereof, e.g. para-aminobenzoic acid (PABA)-based chemicals; etc.

Methods of the present description include administering an amount of a composition as described herein that is a therapeutically effective to prevent or treat the disease or condition.

Prevention/Treatment of Two or More Diseases/Conditions

In some aspects, the subjects treated by the compositions and methods described herein receive treatment with two or more separate compositions, each of which comprises 25HC3S or pharmaceutically acceptable salt thereof, and each of which is prescribed or used for a different disease or condition. For example, a subject that is taking an oral dosage form of 25HC3S or pharmaceutically acceptable salt thereof (e.g. as described in U.S. Pat. No. 8,399,441), or a composition as described herein, to treat high cholesterol, may also be treated for a different disorder e.g. acute liver failure due to APAP overdose, with an IV formulation of a different composition as described herein, or even with a third composition such as a topical formulation to treat e.g. contact dermatitis. The different compositions may have different properties, e.g. the form may differ (e.g. a tablet vs liquid vs cream), the mode or delivery may differ (e.g. oral vs intravenous vs topical) and the concentration of 25HC3S or pharmaceutically acceptable salt thereof and other components in the composition may differ to suit the particular disease or condition. The recommended dosing regimen and the duration of the treatment may also differ but may overlap, e.g. a patient may be treated for dermatitis with a topical cream while taking an oral preparation (e.g. a capsule) for high cholesterol and/or while being treated for ALF due to an APAP overdose. The treatment for high cholesterol may involve a regimen of one daily tablet for many years with a relatively low dosage of 25HC3S or pharmaceutically acceptable salt thereof; the treatment for dermatitis may involve application of a cream twice daily until symptoms disappear; and the treatment for acute liver failure due to APAP overdose may involve administration of large volumes of a composition as described herein with very high 25HC3S or pharmaceutically acceptable salt thereof and/or PG concentrations, and lower amounts (e.g. 5% or less), in one or two boluses.

Description of Administration of the Compositions

Implementation of the methods generally involves identifying patients suffering from or at risk of developing a disease or condition described herein, and administering a composition as described herein by an appropriate route. The exact dosage to be administered may vary depending on the age, gender, weight and overall health status of the individual patient, or on other treatments being received by the patient, as well as the extent or progression of the disease condition being treated and the precise etiology of the disease. However, in general for administration in mammals (e.g. humans), sufficient composition is administered to achieve 25HC3S or pharmaceutically acceptable salt thereof dosages in the range of from about 0.001 to about 100 mg or more per kg of body weight per 24 hr., and preferably about 0.01 to about 50 mg of compound per kg of body weight per 24 hr., and more preferably about 0.1 to about 10 mg of compound per kg of body weight per 24 hr. are effective. Daily doses (in terms of 25HC3S or pharmaceutically acceptable salt thereof) generally range from about 0.1 milligram to about 5000 milligrams per person per day. In some aspects, the dose is from about 10 milligrams to about 2000 milligrams per person per day, or about 100 milligrams to about 1000 milligrams per person per day. The dose will vary with the route of administration, the bioavailability, and the particular formulation that is administered, as well as according to the nature of the malady that is being prevented or treated.

Administration may be oral or parenteral, including intravenously, intramuscularly, subcutaneously, intradermal injection, intraperitoneal injection, etc., or by other routes (e.g. transdermal, sublingual, rectal and buccal delivery, inhalation of an aerosol, intravaginally, intranasally, topically, as eye drops, via sprays, by iontophoresis, by photoacoustic-guided drug delivery, microneedle delivery, etc. The route of administration typically depends on the nature of the condition that is treated and on e.g. whether the treatment is prophylactic or intended to effect a cure of disease that is present. For example, to achieve a preventative effect before organ dysfunction has occurred, oral dosing may be sufficient, especially in view of the excellent bioavailability of orally administered 25HC3S or pharmaceutically acceptable salt thereof. Further, administration of the compound by any means may be carried out as a single mode of therapy, or in conjunction with other therapies and treatment modalities, e.g. surgery, other medicaments (e.g. pain medications, etc.), neutraceuticals, diet regimens, exercise, etc. In some aspects, the product involves a ready to use product solution that can be administered by intravenous bolus, intravenous infusion (upon dilution with pharmaceutically appropriate diluents), intramuscular, subcutaneous, or oral routes. In other aspects, the product involves a solid (e.g. a lyophilized solid) that is reconstituted prior to administration.

The subject to whom the composition is administered is generally a mammal, frequently a human, but this is not always the case. Veterinary applications of this technology are also contemplated, e.g. for companion pets (cats, dogs, etc.), or for livestock and farm animals, for horses, and even for "wild" animals that have special value or that are under the care of a veterinarian, e.g. animals in preserves or zoos, injured animals that are being rehabilitated, etc.

In some aspects, the compositions are administered in conjunction with other treatment modalities such as various pain relief medications, anti-arthritis agents, various chemotherapeutic agents, antibiotic agents, various intravenous fluids (e.g. saline, glucose, etc.), and the like, depending on the malady that is afflicting the subject. "In conjunction with" refers to both administration of a separate preparation of the one or more additional agents, and also to inclusion of the one or more additional agents in a composition of the present disclosure. For example, aspirin, ibuprofen and acetaminophen, which all have potential serious organ-damaging side effects when taken long term, or when taken by certain vulnerable groups (e.g. the very young, the elderly, etc.), or when overdoses are ingested, etc., may be administered by inclusion in a composition as described herein. Accordingly, dosage forms comprising 25HC3S or pharmaceutically acceptable salt thereof and at least one cyclic oligosaccharide, e.g., CD, and one or more of such agents are contemplated.

The administration of the compound of the present disclosure may be intermittent, or at a gradual or continuous, constant or controlled rate. In addition, the time of day and the number of times per day that the pharmaceutical formulation is administered may vary and are best determined by a skilled practitioner such as a physician. For example, for treatment of an APAP overdose, the compound may be administered within 1 week, such as within 1 day, within 12 hours, within 4 hours, within 1 hour, or within 10 minutes, of an overdose e.g. of an agent that causes organ damage. The compound may be administered at least once a day (e.g., twice daily) before surgery for at least 1 month or at least 1 week, or at least 1 day before surgery, or even during surgery, e.g. surgery related to or associated with or which may cause organ failure (e.g. surgery that involves intentional ischemia/reperfusion). The compound may also be administered on at least a daily basis (e.g., twice daily) after surgery for at least 1 day, at least 1 week, or at least 1 month. For example, the surgery may be heart surgery (e.g., coronary artery bypass grafting (CABG)), cardiovascular surgery, heart-lung transplant, lung surgery (e.g., pulmonary embolism surgery), deep vein thrombosis (DVT) surgery, brain surgery, liver surgery, bile duct surgery, kidney surgery (e.g., kidney stone surgery), gastrointestinal surgery (e.g., intestinal, intestinal blockage, diverticulitis, or intestinal torsion surgery), or aneurysm surgery. In some cases, such as when one or more organs to be treated comprises a liver, the administering may occur for not more than 14 days, such as not more than 10 days, not more than 8 days, not more than 5 days, or not more than 1 day.

The compositions (preparations) of the present disclosure may be formulated for administration by any of the many suitable means which are known to those of skill in the art, including but not limited to: orally, by injection, rectally, by inhalation, intravaginally, intranasally, topically, as eye drops, via sprays, etc. In some aspects, the mode of administration is oral, by injection or intravenously. Typically, oral administration is particularly effective when used prophylactically, e.g. to prevent organ damage (e.g. caused by or necrosis and/or apoptosis) and that would otherwise occur in a patient who is taking an organ-damaging agent and/or is exposed to a toxic agent such as radiation, either acutely or for a prolonged period of time, e.g. weeks, months or years. When damage has already occurred, and especially when disease symptoms are already evident, the route of administration is generally parenteral or intravenous to speed delivery of the active agents in the composition.

The present disclosure will be further illustrated by way of the following Examples. These Examples are non-limiting and do not restrict the scope of the disclosure.

EXAMPLES

Example 1. Solubility Studies

This Example describes pharmaceutically appropriate aqueous based solution compositions comprising 25HC3S and various cyclodextrins.

This Example documents the determination that the solubility of 25HC3S forms stable inclusion complexes with cyclodextrins, and that such inclusion complexes are highly water soluble relative to the non-complexed drug.

Solubility in Cyclodextrins

A total of six suspensions of 25HC3S sodium salt were prepared in water containing 0, 50, 100, 200, 250 and 400 mg/mL hydroxypropyl-β-cyclodextrin (HPbCD, hydroxypropyl betadex) or sulfobutyl ether β-cyclodextrin (SBECD, Captisol®). Both cyclodextrins are used in approved pharmaceutical products and are manufactured as Good Manufacturing Practice (GMP) excipients. Each suspension was agitated at room temperature, aliquots were centrifuged, and the supernatant solutions assayed for 25HC3S concentrations by a reverse phase HPLC method. The solubility data of 25HC3S as a function of HPbCD concentrations is in Table 1 and as a function of SBECD concentrations is in Table 2.

TABLE 1

Solubility of 25HC3S as function of HPbCD concentrations at room temperature

| Concentration of HPbCD (mg/mL) | Molar of HPbCD (MW = 1460) | 25HC3S Solubility (mg/mL) | Molar of 25HC3S (MW = 504.7) |
|---|---|---|---|
| 400 | 0.2740 | 65.18 | 0.12915 |
| 250 | 0.1713 | 42.37 | 0.08395 |
| 200 | 0.1370 | 31.97 | 0.06334 |
| 100 | 0.0685 | 18.44 | 0.03654 |
| 50 | 0.0342 | 9.78 | 0.01938 |
| 0 | 0.0000 | 0.14 | 0.00028 |

TABLE 2

Solubility of 25HC3S as function of SBECD concentrations at room temperature

| Concentration of SBECD mg/mL | Molar of SBECD (MW = 2163) | 25HC3S Solubility (mg/mL) | Molar of 25HC3S (MW = 504.7) |
|---|---|---|---|
| 400 | 0.1849 | 44.76 | 0.08869 |
| 200 | 0.0925 | 21.24 | 0.04208 |
| 100 | 0.0462 | 9.86 | 0.01954 |
| 50 | 0.0231 | 6.03 | 0.01195 |
| 0 | 0 | 0.14 | 0.00028 |

FIG. 1 depicts a solubility phase diagram which is a plot of the maximum equilibrium solubility of 25HC3S sodium salt as a function of HPbCD and SBECD concentrations in water. The ordinate (Y-axis) is drug solubility (units are mg/mL) and the abscissa (X-axis) is HPbCD and SBECD concentrations (also mg/mL). The data in FIG. 1 indicates that as HPbCD concentrations are increased, greater amounts of 25HC3S are solubilized. The relative amounts of HPbCD needed to solubilize 25HC3S are in an approximately 6 to 1 ratio, on a mg/mL basis. For example, a 400 mg/mL solution of HPbCD will solubilize 66 mg/mL of 25HC3S. This ratio is constant from low to high solubility of 25HC3S. If 30 mg of 25HC3S is intended for SC administration, where the clinical dosing volume is 1 mL or less, then a 30 mg/mL 25HC3S solution solubilized by 250 mg/mL HPbCD, can be administered. If 30 mg of 25HC3S is intended for intravenous bolus injection, where a bolus injection dosing volume can be 6 mL, then a 5 mg/mL 25HC3S solution solubilized by 42 mg/mL HPbCD, can be administered.

Figure 2:
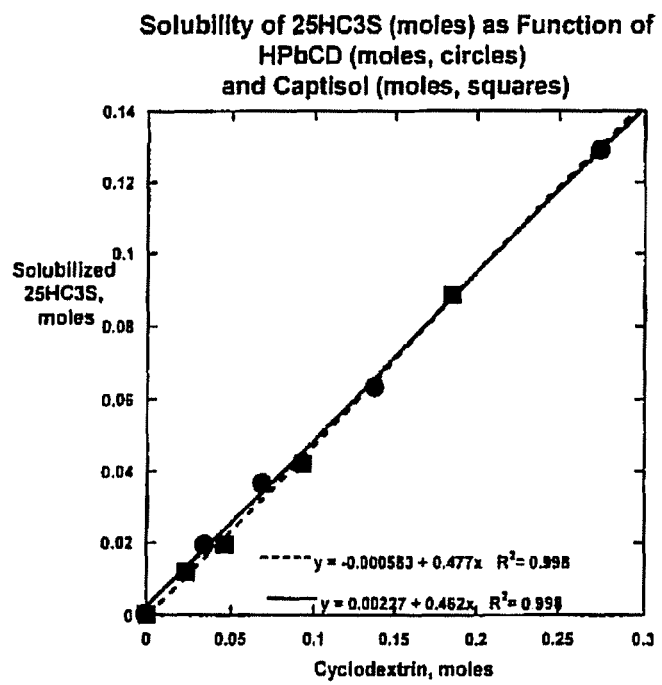
FIG. 2 shows the solubility of 25HC3S (moles) as a function of HPbCD and SBECD (moles).

FIG. 2 is a solubility phase diagram which is a plot of the maximum equilibrium solubility of 25HC3S sodium salt as a function of HPbCD and SBECD concentrations in water. The ordinate (Y-axis) is drug solubility (units are moles) and the abscissa (X-axis) is HPbCD and SBECD concentrations (also moles). As seen in FIG. 2, both cyclodextrins are equally capable, on a molar basis, of solubilizing 25HC3S to the same extent in water.

Solubility of 25HC3S in Water with HPbCD at Multiple Temperatures

The optimal concentration of HPbCD to solubilize a high amount of 25HC3S, and to contain a small amount of buffer (10 mM phosphate buffer) to minimize pH changes on stability, is 250 mg/mL HPbCD. The solution of 30 mg/mL 25HC3S sodium salt, 250 mg/mL HPbCD with 10 mM sodium phosphate buffer in water has an osmolality of approximately 320 mmol/kg. Isotonic solutions range from 270-340 mmol/kg. Higher concentrations of HPbCD greater than 250 mg/mL with higher than 30 mg/mL concentrations of 25HC3S lead to hypertonic solutions. Hypertonic solutions can cause pain upon subcutaneous and intramuscular injection. Conversely, concentrations of HPbCD much less than 250 mg/mL with much less than 30 mg/mL concentrations of 25HC3S require the addition of an isotonic agent, such as sodium chloride or mannitol, to bring the isotonicity into the expected range for a parenteral dosage form.

To confirm that the optimal formulation containing 30 mg/mL 25HC3S sodium salt with 250 mg/mL HPbCD with 10 mM phosphate buffer has adequate solubility over the temperatures of manufacture and storage, a solubility study was conducted at 5° C., 15° C. and 25° C. A total of five suspensions of 25HC3S were prepared in 10 mM sodium phosphate buffer at pH 7.6 containing 0, 50, 100, 250 and 400 mg/mL HPbCD. The suspensions were initially sonicated and then stirred. Each suspension (40 mL for the suspension without HPbCD and 20 mL for the remaining suspensions) was then equally divided into 3 vials and stored in 5° C., 15° C. and 25° C./60% relative humidity (RH) stability chambers.

Each suspension was stirred constantly in the stability chambers by a small spin bar and electronic stirrer. At day 1 and day 3, half of each suspension (approximately 6 mL for the sample without HPbCD and 3 mL for the rest of the suspensions with HPbCD) was withdrawn from the vial with a 3 or 5 mL disposable syringe. A syringe filter was then attached to the syringe for filtration of the suspensions. To minimize sample temperature changes during filtration, the syringe and filter were equilibrated at the respective stability chamber temperatures before their use. Approximately 3 mL of the filtrate for the sample without HPbCD and 1 mL of the filtrate for the remaining suspensions in HPbCD were discarded to ensure that the filter membrane was sufficiently saturated with 25HC3S to prevent absorption of the drug from the remaining filtrate. Then approximately 0.5 mL to 1.5 mL of filtrate was collected for HPLC analysis. At day 3, the remaining filtered portions were measured for pH. Reverse phase HPLC was used for measuring the concentration of 25HC3S in the solubility samples.

The Day 3 solubility results are listed in Table 3. The results indicate that the solubility of 25HC3S in the presence of HPbCD is not temperature dependent between 5° C. and 25° C. This allows the 25HC3S solution formulation to be stored at several different long term storage conditions to maximize physical and chemical stability of 25HC3S.

TABLE 3

Solubility of 25HC3S as a function of HPbCD concentrations at 5° C., 15° C. and 25° C./60% RH

| Storage Condition | HPbCD Concentration (mg/mL) | Solubility (mg/mL) at Day 3 Day 3 | pH of Filtrate Day 3 |
|---|---|---|---|
| 5° C. | 0 | 0.0 | 7.62 |
| | 50 | 9.32 | 7.70 |
| | 100 | 18.31 | 7.80 |
| | 250 | 42.80 | 8.06 |
| | 400 | 66.89 | 8.42 |
| 15° C. | 0 | 0.0 | 7.59 |
| | 50 | 9.50 | 7.77 |
| | 100 | 18.51 | 7.98 |
| | 250 | 43.79 | 8.07 |
| | 400 | 68.10 | 8.26 |
| 25° C./60% RH | 0 | $0.006^1$ | $7.53^2$ |
| | 50 | 9.90 | 7.65 |
| | 100 | 18.33 | $7.67^2$ |
| | 250 | 42.37 | $7.84^2$ |
| | 400 | 70.80 | $8.34^2$ |

[1]The 25HC3S suspension samples without HPbCD were centrifuged for solubility determination. Filtered samples had no detectable 25HC3S at the methods detection limit of 0.001 mg/mL. Millex GV 0.2 μm syringe filter was used for filtration of the solubility samples with HPbCD present.
[2]There was not enough day 3 filtrate left for pH measurements. The suspension (left overnight at ambient room temperature after day 3 solubility study) was centrifuged at 12,000 rpm for 10 minutes. The supernatant was used for the pH measurements.

Solubility of 25HC3S in Water with Other Cyclodextrins

The solubility of 25HC3S at ambient room temperature for one day in 5 and 10% (w/v) alpha cyclodextrin (α-CD), 1% (w/v) beta cyclodextrin (β-CD) and 5 and 10% (w/v) gamma cyclodextrin (γ-CD), each containing 10 mM phosphate buffer at pH 7.4 was determined by an HPLC method.
Method α-CD, β-CD and γ-CD were used in the study. Sodium phosphate monobasic, monohydrate and sodium phosphate, dibasic, anhydrous were used to prepare 10 mM phosphate buffer at pH 7.4.
Sample Preparation for the Solubility Study:

Approximately 30 to 50 mg of 25HC3S was weighed into a 20 mL vial (5 vials total, one vial for each vehicle). Approximately 8 mL each of 5 and 10% (w/v) α-CD, 1% (w/v) β-CD, and 5 and 10% (w/v) γ-CD containing 10 mM phosphate buffer at pH 7.4 was added to each vial, respectively. The samples were sonicated and vortexed to disperse the drug. The drug suspensions in these 5 vials were stirred at 500 rpm at ambient RT (20.0-22.2° C.). On day 1, approximately 1.2 mL each of the suspensions was transferred into 2 mL conical vials (a total of 5 vials for each suspension) and centrifuged at 12,000 rpm for 10 mM. Approximately 1 mL of the supernatant from each suspension (prior to filtration) was used for HPLC analysis. The supernatants for the rest of the vials from the same suspension were combined together and filtered through 0.45 μM, 13 mm in diameter Acrodisk syringe filter with Nylon membrane. The first 2-mL of filtrate was discarded. The next 2 consecutive filtrates of 0.5-0.7 mL each were collected into HPLC vials for analysis.

The solubility of α, β and γ CD in water is 12.9, 1.8 and 24.9% (w/v), respectively (relatively lower compared to the solubility of HP-β-CD in water at 50% w/v at 25° C.). Therefore, a total of 5 vehicles well within their solubility limits were prepared: 5 and 10% (w/v) α-CD, 1% (w/v) β-CD and 5 and 10% (w/v) γ-CD in 10 mM phosphate buffer at pH 7.4. The solubility of 25HC3S in these 5 vehicles was determined and summarized in Table 4. 25HC3S shows the best solubility in 1% (w/v) f3-CD (2177.4 μg/mL). The solubility of 25HC3S in 5 and 10% (w/v) α-CD is very low, 32.9 and 45 μg/mL, respectively. The solubility of 25HC3S in 5 and 10% (w/v) γ-CD is 564.4 and 152.1 μg/mL, respectively. An experiment was repeated to confirm that the solubility of 25HC3S in 5% (w/v) γ-CD is actually greater than that in 10% (w/v) γ-CD. The repeated solubility of 25HC3S in 5 and 10% (w/v) γ-CD was 292.4 and 98.2 μg/mL, respectively. The repeated solubility was slightly lower compared to the initial study (probably because the solubility is not the equilibrium solubility). However, the solubility trend (greater solubility in 5% (w/v) γ-CD) was confirmed.

stirring of an overhead mixer at 100-200 rpm for a minimum of 5 minutes to create a clear solution. HPbCD, NF (1851.85 g) was added in small portions over 15 minutes with slow stirring into the beaker. The stirring was increased to 250-350 rpm for an additional minimum 30 minutes to form a clear solution. The solution was filtered through a 0.22 micron filter. Filtered vehicle (7 mL) was filled into 10 mL glass vials, which were sealed with 20 mm stoppers, and crimp sealed. The vehicle vials were sterilized with gamma irradiation at approximately 28-32 kGy.

Preparation of 25HC3S for Injection, 186 mg/Vial

25HC3S sodium salt was micronized by passing through a Fluid Energy Model 00 Jet-O-Mizer Jet Mill. Micronized drug substance (186 mg) was added into a 10 mL glass vial, sealed with 20 mm stoppers, and crimp sealed. The 25HC3S powder vials were sterilized with gamma irradiation at approximately 28-32 kGy Constitution of 25HC3S Sodium Salt for Injection, 30 mg/mL after Constitution Sterile vehicle (6.0 mL) comprised of 250 mg/mL HPbCD and 10 mM phosphate buffer was added to a vial of 25HC3S micronized powder. The mixture was shaken for 15 minutes to prepare a solution resulting in a 25HC3S sodium salt concentration of 30 mg/mL (allowing for 3% dilution upon the dissolution of drug). The constituted product solution can be administered by intravenous bolus, intravenous infusion (upon dilution with pharmaceutically appropriate

TABLE 4

Solubility of 25HC3S as a function of Cyclodextrin at Room Temperature

| alpha-CD (mg/mL) | alpha-CD (% wt/vol) | 25HC3S Solubility (μg/mL) | alpha-CD (mM) | 25HC3S Solubility (mM) | Ratio of CD/25HC3S (mM/mM) | Complexation with CD |
|---|---|---|---|---|---|---|
| 0 | 0 | 6 | 0.000 | 0.012 | NA | NA |
| 50 | 5 | 32.9 | 51.395 | 0.065 | 791 | no |
| 100 | 10 | 45 | 102.791 | 0.089 | 1155 | no |

| beta-CD (mg/mL) | beta-CD (% wt/vol) | 25HC3S Solubility (μg/mL) | beta-CD (mM) | 25HC3S Solubility (mM) | Ratio of CD/25HC3S (mM/mM) | Complexation with CD |
|---|---|---|---|---|---|---|
| 0 | 0 | 6 | 0.000 | 0.012 | NA | NA |
| 10 | 1 | 2177.4 | 8.811 | 4.314 | 2 | yes |

| gamma-CD (mg/mL) | gamma-CD (% wt/vol) | 25HC3S Solubility (μg/mL) | gamma-CD (mM) | 25HC3S Solubility (mM) | Ratio of CD/25HC3S (mM/mM) | Complexation with CD |
|---|---|---|---|---|---|---|
| 0 | 0 | 6 | 0.000 | 0.012 | NA | |
| 50 | 5 | 564.4 | 38.547 | 1.118 | 34 | no |
| 100 | 10 | 152.1 | 77.093 | 0.301 | 256 | no |

Example 2. Manufacturing of 25HC3S Cyclodextrin Formulations

I. Manufacturing 25HC3S Sodium Salt for Injection, 30 mg/mL after Constitution

Preparation of Sterile Vehicle (250 mg/mL HPbCD with 10 mM Phosphate Buffers in Water)

Sterile water for injection, USP (6.14 kg) was added into a 10 L stainless steel vessel. Sodium phosphate monobasic monohydrate, USP (2.05 g) and 8.42 g of sodium phosphate dibasic anhydrous, USP were added to the water with slow diluents), intramuscular, subcutaneous, or oral routes. Similar formulations can be prepared using SBECD at the same molar ratio as HPbCD.

Stability Testing for 25HC3S Sodium Salt for Injection, 30 mg/mL after Constitution Stability data for 6 months at 2-8° C. to 40° C./75% RH for 25HC3S for injection, 30 mg/mL after constitution, are listed in Table 5. This lot of 25HC3S powder, and the vehicle used to constitute it, were gamma sterilized at approximately 28-32 kGy. The data supports a 12 month retest date when stored at 2-8° C.

TABLE 5

Stability testing for 25HC3S sodium salt, 30 mg/mL after constitution

| Test [1,2,3,4] | Stability Acceptance Criteria | 0 | 2-8° C. Long Term Conditions 3 Months | 2-8° C. Long Term Conditions 6 Months |
|---|---|---|---|---|
| Appearance | White to off white powder | White powder | White to off white powder | White powder |
| Degree of Coloration of Liquids | Read and Record | BY6 | Between BY5 and BY6 | BY6 |
| Assay | 90.0% - 110.0% label strength of 30 mg/mL | Mean: 98.7% (n = 10, RSD = 3%) | 96.7 (96.8, 96.5) | 100.0 (100.1, 99.8) |
| % Individual Unspecified Degradant (Average n = 2) | Report Individual Unspecified Degradant ≥ 0.05% | RRT = 0.60  0.2<br>RRT = 0.64  0.4<br>RRT = 2.74  0.4<br>RRT = 3.77  0.3 | 0.2<br>0.4<br>0.4<br>0.3 | 0.3<br>0.4<br>0.4<br>0.3 |
| % Total Degradation Products | Report | 2.5 (2.4, 2.4) | 2.8 (2.8, 2.8) | 3.0 (2.9, 3.0) |
| pH | Read and Record | 6.62 (6.61, 6.62) | 5.82 (5.90, 5.73) | 5.34 (5.34, 5.33) |
| Osmolality (mmol/kg) | Read and Record | 321 (319, 322) | 322 (320, 323) | 323 (324, 321) |
| % Water Content | Read and Record | 6.23 (RSD = 4%) | 5.62 (RSD = 2%) | 6.13 (RSD = 9%) |

| 25° C./60% RH Accelerated Condition | | | 40° C./75% RH Stress Condition | | |
|---|---|---|---|---|---|
| 1 Month | 3 Months | 6 Months | 1 Month | 3 Months | 6 Months |
| White powder | White to off white powder | White powder | White powder | White to off white powder | White powder |
| Between BY5 and BY6 | BY5 | BY5 | Between BY4 and BY5 | Between BY3 and BY4 | Between BY3 and BY4 |
| 98.3 (96.9, 99.7) | 96.0 (96.7, 95.3) | 96.2 (96.0, 96.3) | 95.8 (96.0, 95.6) | 96.2 (95.5, 96.9) | 97.1 (97.2, 96.9) |
| 0.3 | 0.3 | 0.4 | 0.3 | 0.3 | 0.4 |
| 0.4 | 0.4 | 0.4 | 0.4 | 0.4 | 0.5 |
| 0.4 | 0.4 | 0.4 | 0.4 | 0.5 | 0.4 |
| 0.3 | 0.3 | 0.3 | 0.3 | 0.4 | 0.3 |
| 2.9 (2.9, 2.8) | 2.9 (2.7, 2.9) | 3.0 (2.8, 3.0) | 2.9 (2.8, 2.7) | 3.3 (3.5, 2.9) | 2.8 (2.6, 2.8) |
| 5.18 (5.17, 5.18) | 4.83 (4.80, 4.85) | 4.73 (4.72, 4.73) | 4.65 (4.64, 4.66) | 4.27 (4.18, 4.36) | 4.15 (4.14, 4.15) |
| 330 (330, 330) | 322 (321, 323) | 319 (319, 319) | 330 (332, 328) | 327 (327, 326) | 324 (324, 324) |
| 5.29 (RSD = 1%) | 5.40 (RSD = 2%) | 5.65 (RSD = 2%) | 5.03 (RSD = 1%) | 5.33 (RSD = 1%) | 6.34 (RSD = 1%) |

[1] RRT = relative retention time.
[2] Only the degradants that were 0.3% or greater on stability are reported in this table. There were 13 other degradants reported between 0.05% and 0.2% at 2-8° C., 15 other degradants reported between 0.05% and 0.2% at 25° C./60% RH and at 40° C./75% RH.
[3] RSD = relative standard deviation
[4] BY = brown - yellow II. Manufacturing 25HC3S Sodium Salt for Injection, 30 lng/mL, Ready to Use Solution Sterile water for injection, USP (331.426 g) was added into a 500 mL glass vessel. Sodium phosphate monobasic monohydrate, USP (110.50 mg) and 453.87 mg of sodium phosphate dibasic anhydrous, USP were added to the water with slow stirring with spin bar for a minimum of 5 minutes to create a clear solution. HPbCD, NF (100.036 g) was slowly added with stirring. The mixture was stirred for a minimum 30 minutes to form a clear solution. The solution was filtered through a 0.2 micron filter. Vehicle filtrate (270.096 g) was transferred into a glass container. 25HC3S drug substance (8.116 g; not micronized) was added over 5 minutes to the glass container with vehicle with stirring. The clear solution was sterile filtered through a 0.22 micron filter. The sterile filtered solution (1.8 mL) was filled into 2 mL glass vials, which were sealed with 13 mm stoppers, and crimp sealed. Alternatively, larger volumes of formulation can be filled into larger size glass vials, stoppered, and sealed. The ready to use product solution can be administered by intravenous bolus, intravenous infusion (upon dilution with pharmaceutically appropriate diluents), intramuscular, subcutaneous, or oral routes. Similar formulations can be prepared using SBECD at the same molar ratio as HPbCD.

Stability Testing of 25HC3S Sodium Salt for Injection, 30 mg/mL, Ready to Use Solution Solutions of 25HC3S sodium salt prepared at a nominal concentration of 30 mg/mL, with 250 mg/mL HPbCD and 10 mM sodium phosphate buffer in water, were placed on stability from −20° C. to 60° C. (1.8 mL in 2 mL glass vials with stoppers and crimp seals). At various time points, samples were assayed by a reverse phase HPLC method, and the 25HC3S concentrations determined. The percent of 25HC3S remaining relative to T=0 at each storage condition is listed in Table 6. The data indicates that 25HC3S would have acceptable stability for 2 years at −20° C. to 25° C./60% RH.

TABLE 6

Stability of 25HC3S as Percent Remaining Compared to t = 0

| Months | −20° C. | 2-8° C. | 25° C./60% RH | 40° C./75% RH | 50° C. | 60° C. |
|---|---|---|---|---|---|---|
| 0 | 100 | 100 | 100 | 100 | 100 | 100 |
| 0.5 | | | | | 99.4 | 97.3 |
| 1.0 | | 102.7 | 102.8 | 102.4 | 95.7 | 91.5 |
| 1.5 | | | | | 94.2 | |
| 2.0 | | | | 101.6 | | 81.5 |
| 2.5 | | | | | 88.4 | |
| 3.0 | 100.5 | 100.3 | 99.7 | 99 | | 69.8 |
| 9.0 | 98.6 | 98.3 | 98.1 | 93 | 61.6 | |

III. Manufacturing 25HC3S Sodium Salt for Injection, 30 mg/mL, Lyophilized Powder for Constitution with Water A 30 mg/mL 25HC3S sodium salt solution in 250 mg/mL HPbCD was prepared, with or without 10 mM sodium phosphate buffer, and with or without 20 mg/mL mannitol, in water. These solutions were aseptically sterile filtered through 0.1 to 0.2 micron membranes. The formulation (1 mL) was filled into 2 mL glass vials. The vials were placed on a lyophilizer and various cooling/freezing rates (0.3 to 2° C./minute) and temperatures (from 5° C. to −45° C.), drying rates (0.2 to 1° C./minute) and temperatures (−30° C. to 20° C.), times (1500 to 1800 minutes), and vacuum (75 to 200 mtorr) cycles were used to prepare lyophilized cakes. The lyophilized cakes were then reconstituted by the addition of 1 mL of water for injection. Other pharmaceutically acceptable sterile aqueous solutions can also be used to reconstitute the product for injection, such as 5% dextrose, 0.9% sodium chloride, and lactated ringers solutions. The reconstitution times varied from 2 to 4 minutes with manual shaking. The reconstituted product solution can be administered by intravenous bolus, intravenous infusion (upon dilution with pharmaceutically appropriate diluents), intramuscular, subcutaneous, or oral routes. Similar formulations can be prepared using SBECD at the same molar ratio as HPbCD.

Example 3. Effect of 25HC3S Administration on Acetaminophen (APAP) Overdose

Materials and Methods

The ability of 25HC3S to treat symptoms of APAP overdose was examined. 12-week-old male C57BL/6J mice were fasted overnight and injected (intraperitoneally) with APAP: 600 mg/kg (high dose) for mortality studies or 350 mg/kg (low dose) for liver function and gene studies. Control mice received only vehicle (20% (v/v) a propylene glycol, 4% (w/v) cyclodextrin (powdered hydroxypropyl beta cyclodextrin in sterile 10% (w/v) glucose.

A composition comprising 25 mg/kg of 25HC3S sodium salt in vehicle was administered intravenously to the experimental mice 0.5 hours after APAP administration. Mortality was monitored in the high dose mice. In the low dose mice, the liver function markers aspartate aminotransferase (AST), alanine aminotransferase (ALT), alkaline phosphatase (ALK) and lactate dehydrogenase (LDH), were measured in serum. Impacts on gene expression were determined by Quantitative Real-time PCR. Membrane potentials were measured using JC1 staining and flow cytometry.

Results

Mortality Studies

Figure 3:
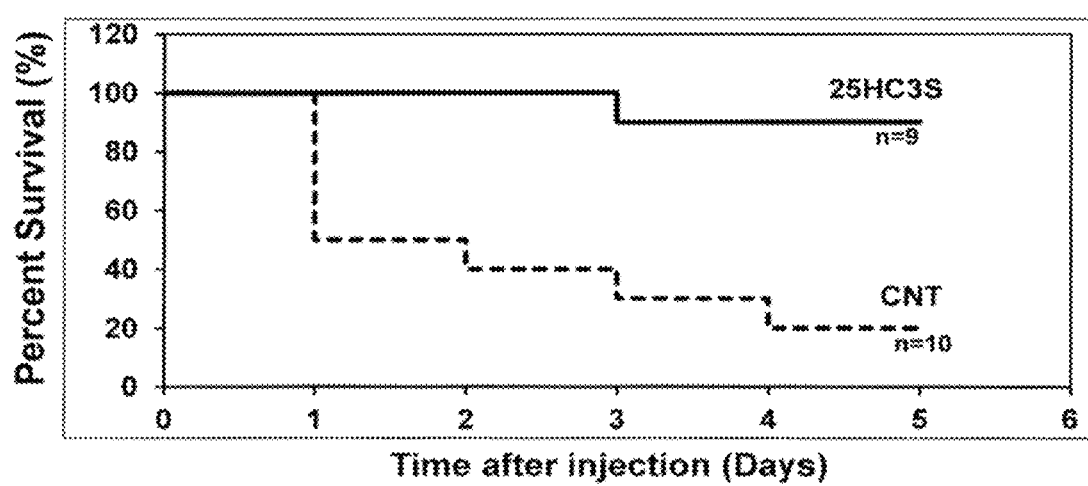
FIG. 3. Effects of 25HC3S on mortality in mice overdosed with APAP (600 mg/kg).
Figure 4A:
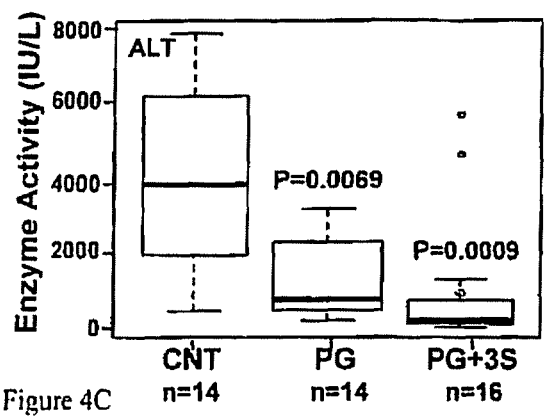
FIGS. 4A-4D. Effects of 25HC3S on liver function in mice overdosed with APAP (350 mg/kg). A, alanine aminotransferase (ALT); B, aspartate aminotransferase (AST); C, alkaline phosphatase (ALK); and D, lactate dehydrogenase (LDH). CNT=control; PG=mice received vehicle; PC+3S=mice received 25HC3S.
Figure 4C:
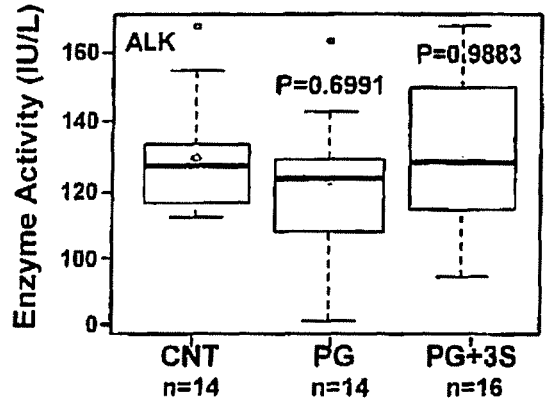
Figure 4B:
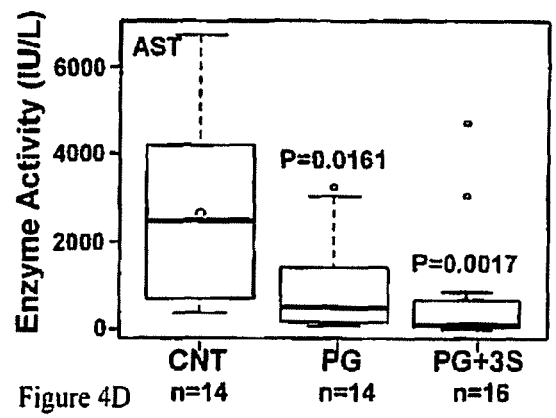
Figure 4D:
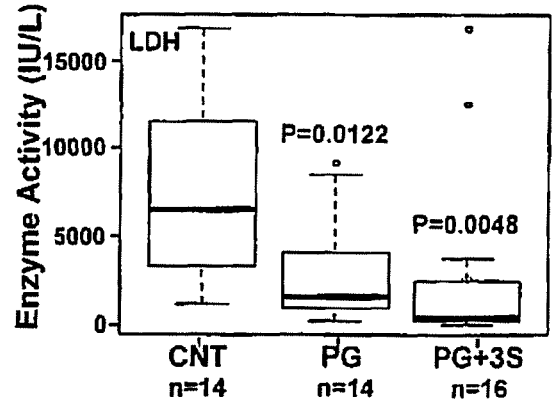
Figure 5A:
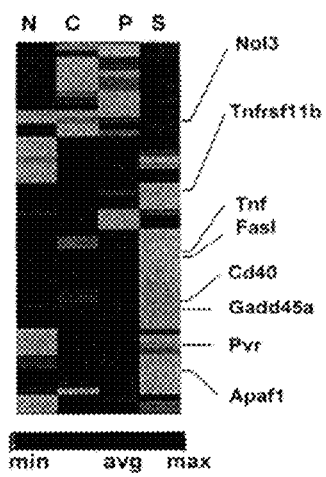
FIGS. 5A-5D. 25HC3S treatment regulates mRNA expression of hepatic apoptosis-related genes in APAP overdosed mice. A, clustergram analysis of data from JC-1/flow cytometry study; B-D, scatter plots of data. B, P (vehicle) vs C (control); C, 25HC3S vs C (control); D, 25HC3S vs P (vehicle). Genes with more than a 2-fold change are indicated.
Figure 5B:
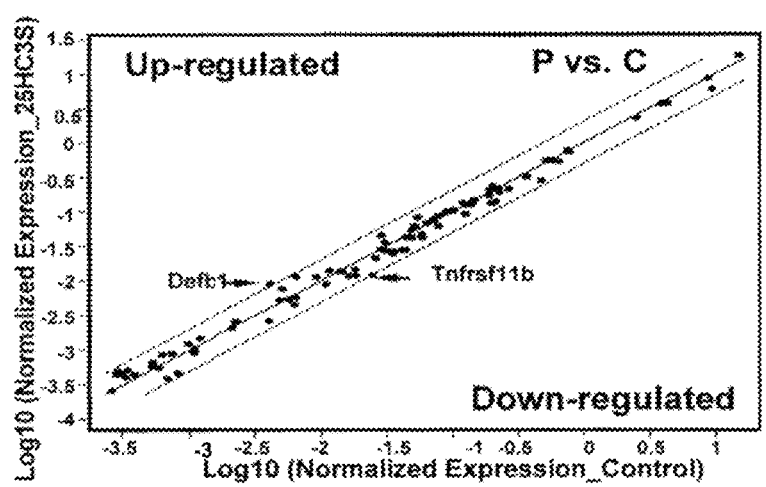
Figure 5C:
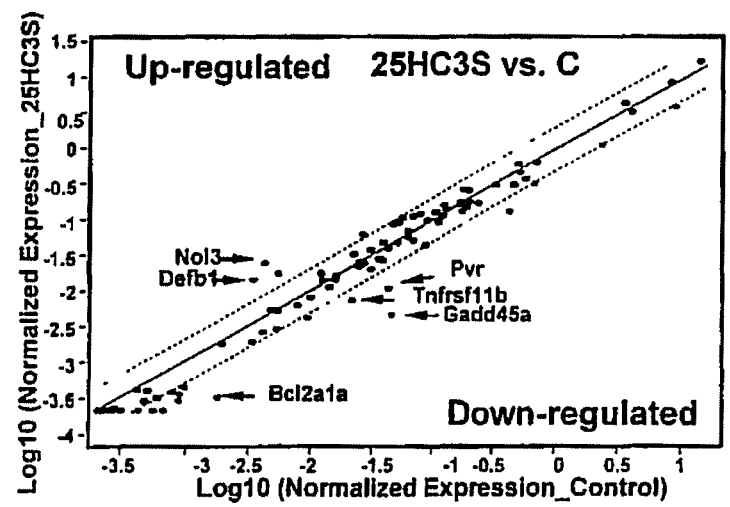
Figure 5D:
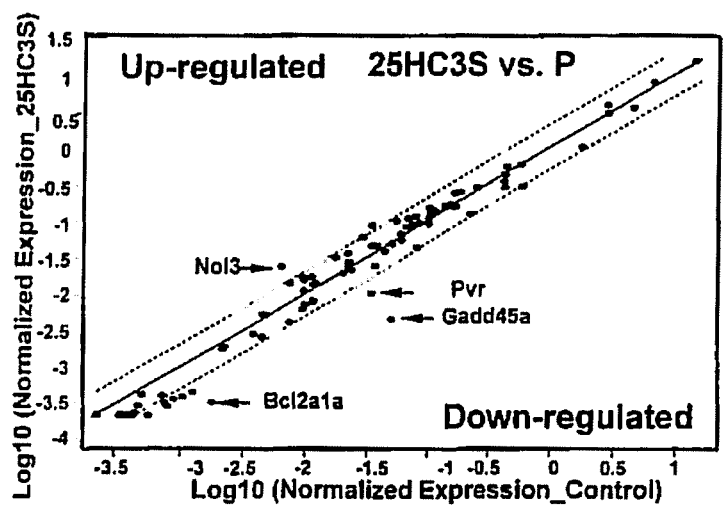
Figure 6A:
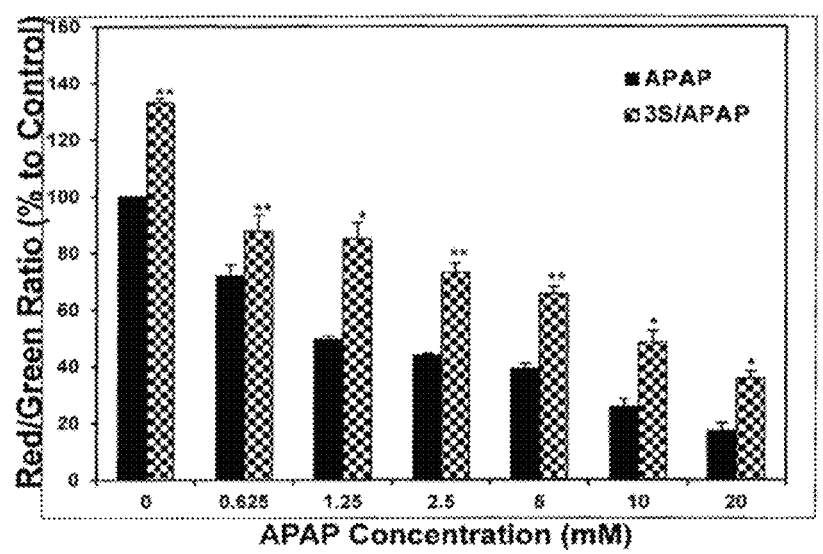
FIGS. 6A and 6B. Effects of 25HC3S on mitochondrial membrane potential in Huh7 cells treated with APAP, as measured by staining with the mitochondrial membrane potential dye (JC-1) and flow cytometry. A, results in terms of APAP concentration; B, results in terms of 25HC3S concentration. Data represent the mean±SD for three independent experiments and is presented as percentage of control (CNT). CNT/DMSO: control group with vehicle; APAP/DMSO: cells were treated with 10 mM APAP only; APAP/12.5: cells were pretreated with 12.5 µM 25HC3S for 2 hr and then incubated with 10 mM APAP before assay; APAP/25: cells were pretreated with 25 µM 25HC3S for 2 hr and then incubated with 10 mM APAP before assay; APAP/50: cells were pretreated with 50 µM 25HC3S for 2 hr and then incubated with 10 mM APAP before assay; APAP/100: cells were pretreated with 100 µM 25HC3S for 2 hr and then incubated with 10 mM APAP before assay. **, P<0.01 vs. APAP/DMSO group.
Figure 6B:
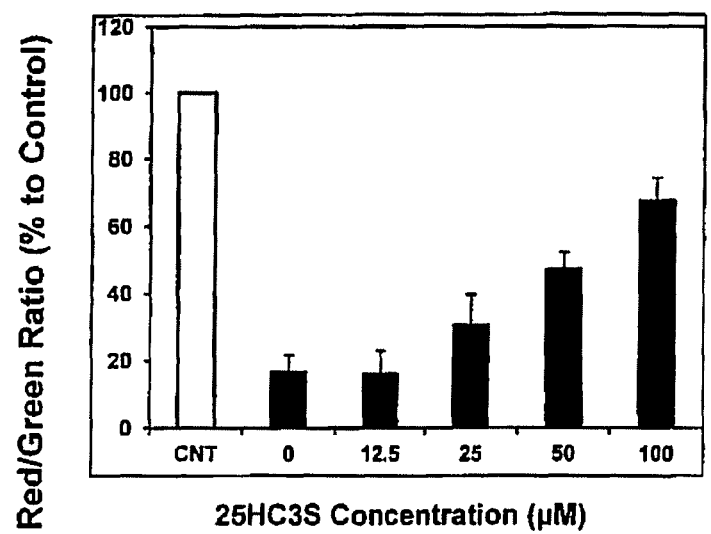

The mortality results are shown in FIG. 3. As can be seen, 5 days after the 600 mg/kg APAP overdose, all of the mice who did not receive treatment with 25HC3S died. In marked contrast, only one of the mice that received 25HC3S treatment had died.

Liver Function

One group of low dose mice received treatment with 25HC3S in vehicle 0.5 hours after the overdose. In this group, liver function markers were assessed 24 hours after treatment. The liver function markers, ALT, AST and LDH, are typically elevated during liver dysfunction or failure, and as can be seen in FIG. 4A-4D, these three markers were significantly elevated in control mice who received 350 mg/kg APAP and no treatment. However, in mice treated with vehicle alone, the values were lowered and in mice treated with vehicle plus 25 mg/kg of 25HC3S, the values were near normal. The differences in the measured values were statistically significant.

Changes in Gene Expression

Changes in gene regulation in low dose mice 24 hours after the administration of vehicle and vehicle plus 25HC3S were investigated. The 12-week-old male C57BL/6J mice had received 350 mg/kg APAP via intraperitoneal injection and 30 min later received 7.6% glucose/$H_2O$ (C) or vehicle (20% PG/4% HCD/7.6% glucose, P) or 25HC3S (3S). Twenty four hours following APAP injection, liver tissue was harvested and total mRNA was extracted and analyzed using an $RT^2$ Profiler™ PCR Array assay. The results are presented in FIG. 5A-D and the expression levels of the most highly regulated genes are presented in Table 7 and Table 8. The listed genes are involved in apoptosis and/or immune system regulation.

TABLE 7

Gene expression change in liver of low dose mice analyzed by an RT² Profiler™ PCR array and expressed as relative fold compared to the control (C) group

| Gene function | Gene symbol | Fold vs C | Gene name |
|---|---|---|---|
| Anti-apoptosis | No13 (NM_030152) | 5.3 | Nucleolar protein 3 (apoptosis repressor with CARD domain |
| Pro-apoptosis | Gadd45a (NM_007836) | −9.3 | Growth arrest and DNA-damage-inducible 45 alpha |
| Pro-apoptosis | Tnfrsf11b (NM_008764) | −2.9 | Tumor necrosis factor receptor superfamily, member 11a |
| Pro-apoptosis | Apaf1 (NM_009741) | −2.2 | Apoptotic peptidase activating factor 1 |
| Pro-apoptosis | Cd40 (NM_011611) | −2.1 | CD40 antigen |
| Pro-apoptosis | Fas1 (NM_010177) | −2.1 | Fas ligand (TNF superfamily, member 6) |
| Regulation in immune system | Pvr (NM_027514) | −3.9 | Poliovirus receptor provided |

TABLE 8

Gene expression change in liver of low dose mice analyzed by an RT² Profiler™ PCR array, relative fold compared to the P (vehicle) group

| Gene Function | Gene symbol | Fold vs P | Gene name |
|---|---|---|---|
| Anti-apoptosis | No13 (NM_030152) | 3.6 | Nucleolar protein 3 (apoptosis repressor with CARD domain |
| Pro-apoptosis | Gadd45a (NM_007836) | −10.9 | Growth arrest and DNA-damage-Pro-apoptosis inducible 45 alpha |
| Pro-apoptosis | Cd40 (NM_011611) | −2.7 | CD40 antigen |
| Pro-apoptosis | Fas1 (NM_010177) | −2.6 | Fas ligand (TNF superfamily, member 6) |
| Pro-apoptosis | Tnf (NM_013693) | −2.4 | Tumor necrosis |
| Regulation in immune system | Pvr (NM_027514) | −3.3 | factor Poliovirus receptor provided |

These results show that administration of 25HC3S influences the expression of genes that are involved in apoptosis and immune system regulation. In particular, anti-apoptosis genes are up-regulated and pro-apoptosis genes are down-regulated.

Example 4. Evaluation of the Anti-Inflammatory Activity of 25HC3S Administered Intradermally in an Imiquimod (IMQ)-Induced Psoriasis Model in Mice Materials and Methods
Animals The subjects for the study were 40 male Balb/C mice (18-22 g). Animals exhibiting no signs of clinical distress, disease or injury during a 72-hr quarantine period were accepted for the study and received routine animal care throughout. The backs of all mice were shaved for an area of about 1.5 cm×2 cm.

Formulations

Two formulations of 25HC3S, Formulation A and Formulation B, were used for the study.

Formulation A was a clear solution of 25HC3S sodium salt (30 mg/mL) in a solution vehicle (250 mg/mL hydroxypropyl betadex (beta cyclodextrin, 2-hydroxypropyl ether, a partially substituted poly(hydroxypropyl) ether of beta cyclodextrin) and 10 mM sodium phosphate buffer in sterile water). Vehicle was stored at 2-8° C. storage and placed at room temperature for 30 min. prior to mixing with powdered 25HC3S just prior to use. Dissolution of the 25HC3S in Vehicle A was rapid and appeared to be complete upon mixing. The concentration of 25HC3S sodium salt in solution was 30 mg/ml.

Formulation B was a milky suspension of 25HC3S sodium salt (25 mg/mL) in a suspension vehicle (30 mg/mL polyethylene glycol 3350, 3 mg/mL polysorbate 80, 7.5 mg/mL NaCl, and 10 mM sodium phosphate buffer in sterile water). The 25HC3S was milled using a Fluid Energy Model 00 Jet-O-Mizer™ to approximately 5 microns average particle size (measured by a Malvern Mastersizer 2000 equipped with a Hydro 2000S dispersion cell). Vehicle was stored at 2-8° C. storage and placed at room temperature for 30 min prior to mixing with powdered 25HC3S just prior to use. Because Formulation B is a suspension, the following mixing protocol was used: 3.0 mL of suspension vehicle was added to a vial containing pre-weighed powdered 25HC3S. The vial was shaken for 15 minutes on a flatbed shaker to create a uniformly white suspension, and then manually inverted 5-10 times, and shaken for 5 more minutes. In addition, immediately before administration, the vial was manually inverted 5-10 times to ensure uniformity of suspension.

Administration of IMQ, vehicle and 25HC3S

IMQ was applied topically once daily in the morning to the shaved back skin (50 mg) and the right ear (12.5 mg) of each mouse in order to induce psoriasis-like conditions.

The 25HC3S in vehicle or the vehicle alone were administered once on Days 0 and 1 and once on Days 3 and 4 by intradermal injection. Injections were done approximately 6 hours after the day's IMQ application. Intradermal injections (50 uL/injection/mouse) were given into the site of the back skin lesion.

Monitoring and Measuring Parameters

Mice were monitored for signs of distress and daily photos of the back lesions were taken. Erythema, scaling, and thickness of the back skin was scored daily on a scale from 0 to 4 by an independent scorer (blind), where 0=none; 1=slight; 2=moderate; 3=marked; and 4=very marked. A cumulative score (erythema+scaling+thickening) was calculated as an indicator of the severity of the inflammation (on a scale of 0-12). Ear and back skin thickness was measured by electronic calipers as an indicator of edema.

Termination (Day 6)

All mice in the study were anesthetized and exsanguinated. The blood was collected, processed to sera and stored at −80° C. for analytical use.

Histopathology

The shaved back skin was collected from each animal at termination, weighed and cut into two halves (cut in half down the middle along the spine). One half was preserved in 10% neutral buffered formalin for histopathology. The other half of back skin was homogenized for measurement of cytokines TNFα and IL-17.

Results

Figure 7:
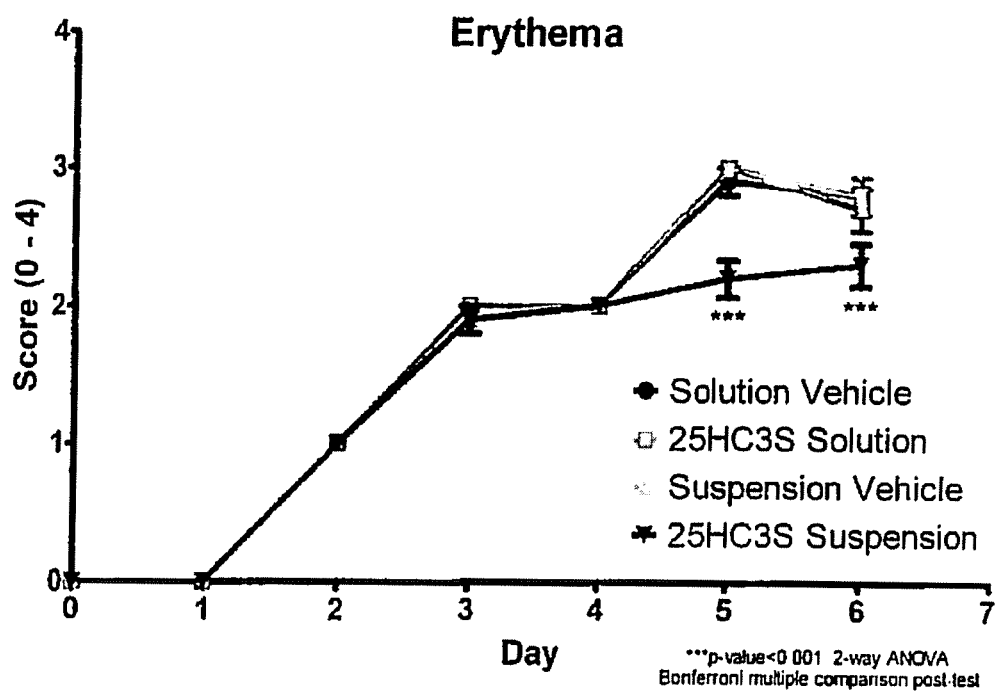
FIG. 7. Erythema (redness) of back skin of mice treated with 25HC3S solution, solution vehicle, 25HC3S suspension, or suspension vehicle.
Figure 8A:
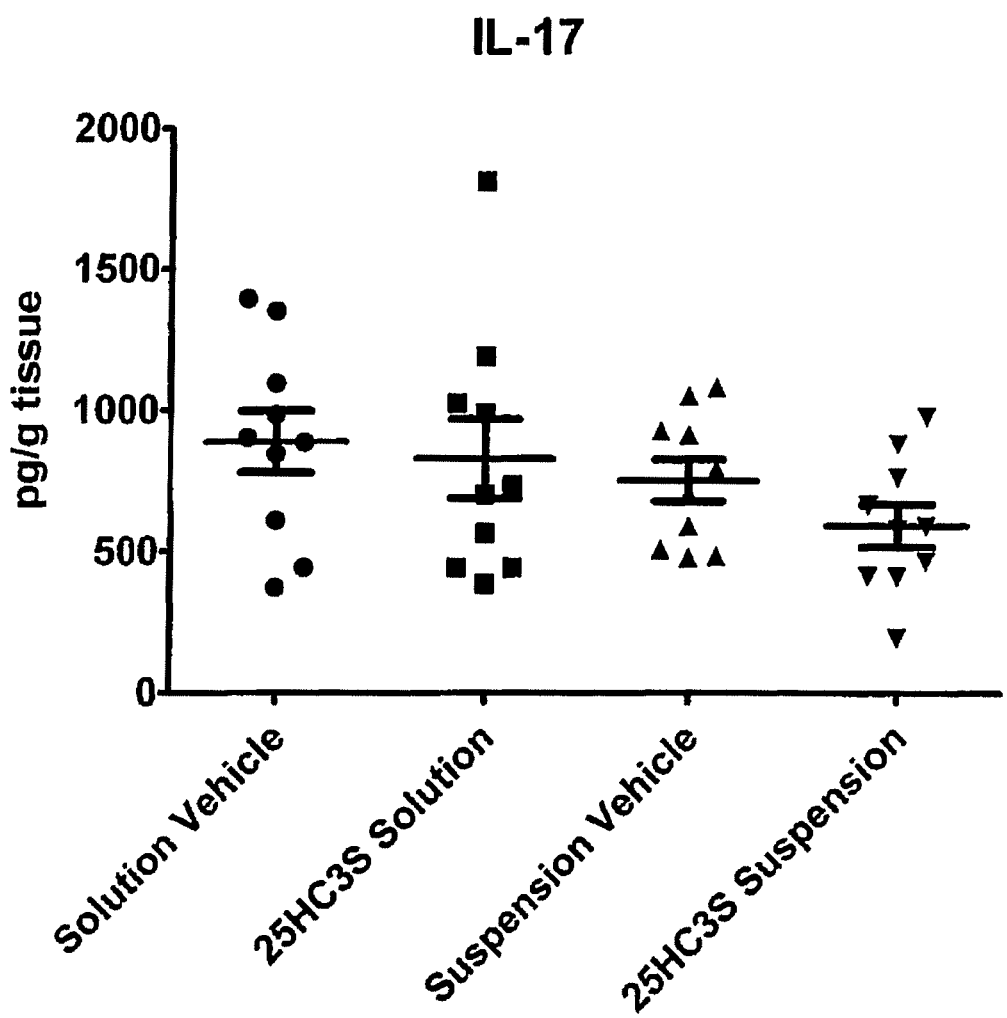
FIGS. 8A and 8B. A, IL-17 and B, TNFα protein levels in psoriatic skin/lesion as measured by ELISA assays.
Figure 8B:
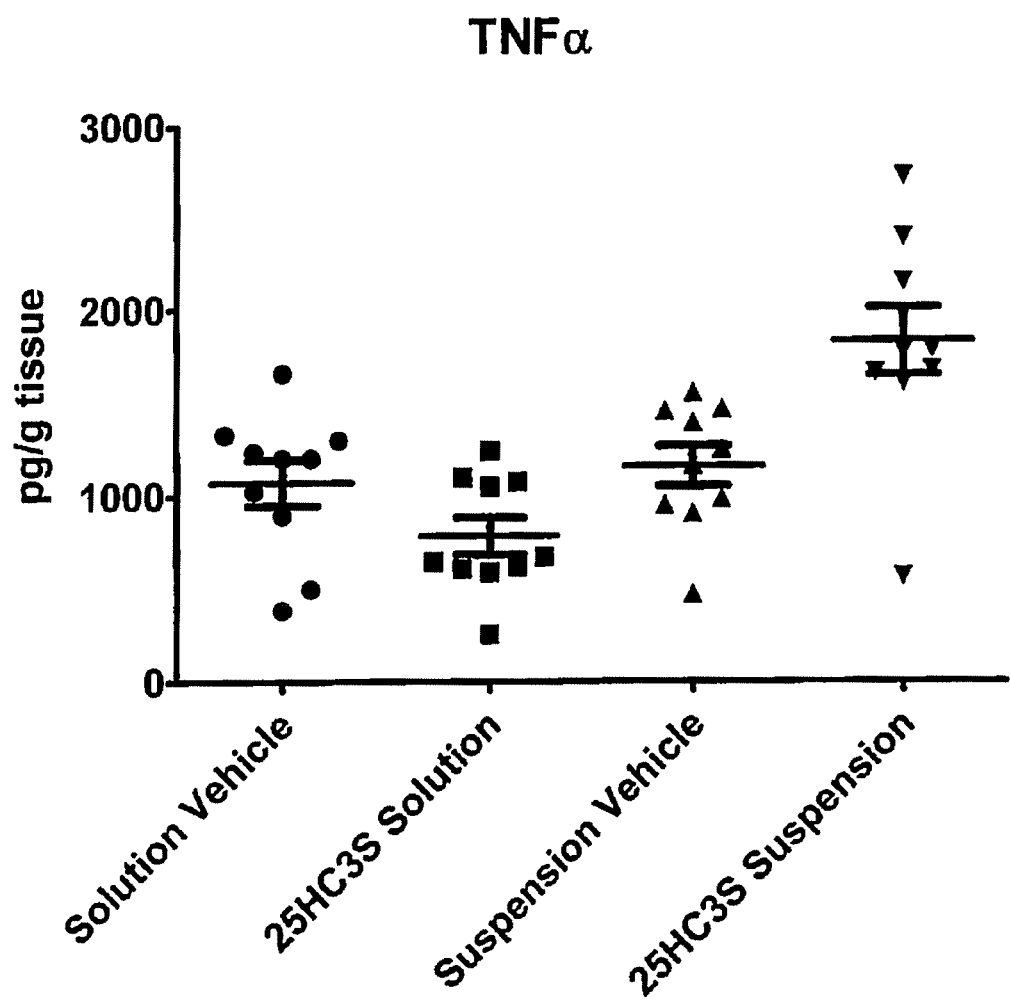

The results of this study are presented in FIGS. 7 and 8A and 8B. As can be seen in FIG. 7, erythema (redness) of the back skin was significantly reduced in mice treated with the Formulation B suspension. Erythema of the back skin was not significantly reduced in mice treated with the Formulation A, and erythema of the right ear was not significantly reduced in mice treated with Formulation A or B.

FIGS. 8A and 8B show IL-17 and TNFα protein levels, respectively, in psoriatic skin/lesions as measured by ELISA. As can be seen, IL-17 trended lower in the Formulation B group compared to the respective vehicle group whereas no major differences were observed the Formulation A and its vehicle groups. In contrast, TNFα protein levels were modestly reduced in the skin tissue of Formulation A-treated mice compared to vehicle while increased in Formulation B-treated mice compared to its respective vehicle. While these results seem contradictory, one caveat of this study is that depending on where the tissue was collected (at the site of the intradermal injection which was contained to a small region of the lesion versus unexposed regions of the psoriatic lesion), protein levels may be dramatically variable within treatment groups. In all, we find that 25HC3S promotes reduction in erythema in a rodent model of psoriasis.

Example 5. Evaluation of 25HC3S on Survival in a Rodent Model of LPS Endotoxin Shock Material and Methods
Animals The subjects for the study were 20 male C57BL/6J mice (20-22 weeks of age, 27-35 g). Animals exhibiting no signs of clinical distress, disease or injury during a 72-hr quarantine period were accepted for the study and received routine animal care throughout.

Formulation

A solution formulation of 25HC3S and its respective vehicle was used for the study. The vehicle was a solution of 4% (w/v) hydroxypropyl betadex, 10% (w/v) dextrose, with 10 mM sodium phosphate buffer in sterile water. Vehicle was stored at 2-8° C. storage and placed at room temperature for 30 minutes prior to dosing.

25HC3S sodium salt was pre-dissolved into the vehicle solution to result in a drug concentration of 5 mg/mL. The 25HC3S solution was ready-to-use at the start of dosing. It was also stored at 2-8° C. storage and placed at room temperature for 30 minutes prior to dosing the mice.

Administration of 25HC3S and LPS Endotoxin 50 mg/kg of 25HC3S in vehicle or vehicle alone (N=10/group) were administered to mice once by intraperitoneal injection 2 hours prior to LPS delivery. A semi-lethal dose of LPS (5 mg/kg) was given by intravenous injection to the tail vein in order to induce an acute inflammatory response that mimics systemic sepsis-like conditions.

Monitoring and Measuring Parameters

Mice were monitored for survival for 6 days after 25HC3S and LPS treatments. Animal checks for mortality were performed twice daily during the 6 day observation period. Animals were examined for any altered clinical signs, including gross motor and behavioral activity, and observable changes in appearance. Moribund animals and animals experiencing undue pain and suffering were euthanized at the discretion of the Study Director, attending veterinarian, or other qualified persons.

Results

Figure 9:
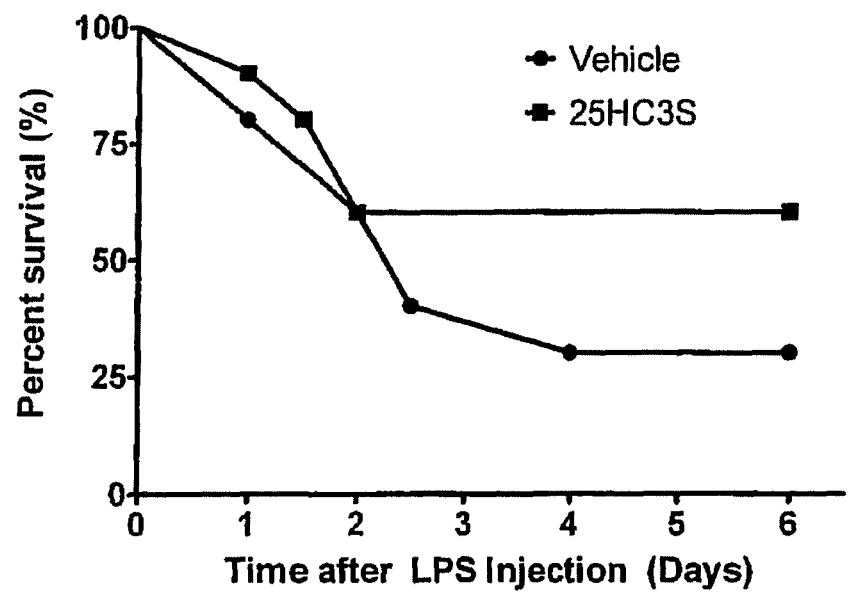
FIG. 9. Effects of 25HC3S on mortality in mice given a semi-lethal dose of LPS (5 mg/kg).

The mortality results are shown in FIG. 9. Six days after 5 mg/kg LPS delivery, 70% (N=7) of the vehicle-treated died. In marked contrast, only 40% (N=4) of mice that received 25HC3S treatment had died. In summary, 25HC3S improved survival in an animal model of sepsis by LPS-induced endotoxin exposure.

Example 6. Additional Exemplary Formulations and Descriptions of Representative Studies Table 9 summarizes Examples 6A-6D, which are discussed in more detail below.

TABLE 9

Summary of Formulation Studies

| | 25HC3S Solution Formulations | | | In Vivo Preclinical Studies Performed | |
|---|---|---|---|---|---|
| Example (n = # studies) | 25HC3S Concentration (mg/mL) | | Vehicle | PK | PD |
| 6A. (n = 1) | 5 | | 40 mg/mL HPbCD with 10 mM sodium phosphate buffers, in 0.675% of sodium chloride | | X |
| 6B. (n = 3) | 3, 6 | | 40 mg/mL HPbCD with 10 mM sodium phosphate buffers, in 0.63% of sodium chloride | | X |
| 6C. (n = 1) | 2.5, 20 | | 200 mg/mL HPbCD with 10 mM sodium phosphate buffers, in water | X | |
| 6D. (n = 3) | 1, 5, 25 | | 250 mg/mL HPbCD with 10 mM sodium phosphate buffers, in water | X | |

Example 6A. Evaluation of 25HC3S on Clinical Signs and Survival in a Rodent Model of Gastrointestinal Acute Radiation Syndrome (GI-ARS)

Material and Methods
Animals

The subjects for the two studies outlined here were (A) Study 1: 20 male C57BL/6J mice (8 weeks of age; 23-28 g) and (B) Study 2: 16 male C57BL/6J mice (8 weeks of age; 23-28 g). Following arrival, all animals were subjected to a health assessment and evaluation was performed in accordance with the standard operating procedures and by technical staff working under the supervision of the clinical veterinarian. An acclimation period of at least 11 days was allowed between receipt of the animals and irradiation to accustom the animals to the laboratory environment.

Formulation

A solution formulation of 25HC3S sodium salt and its respective vehicle was used for the study. The Vehicle was a solution of 4% (w/v) hydroxypropyl betadex in 75% (v/v) of 0.9% (w/v) sodium chloride and 25% (v/v) sterile water. 25HC3S sodium salt was pre-dissolved into the Vehicle solution to result in a drug concentration of 5 mg/mL. The 25HC3S solution was ready-to-use at the start of dosing. In Study 1, the vehicle was stored at 2-8° C. whereas the 25HC3S solution was stored at room temperature prior and throughout the study duration; in Study 2, both vehicle and 25HC3S solutions were stored at 2-8° C.

Whole-Body Irradiation with Partial Shielding and 25HC3S Administration

Partial shielding irradiation (PSI) exposure at a high radiation dose (>10 Gy) is an established approach to mimic GI-ARS in mice. Animals were exposed to whole-body irradiation with partial shielding (Day 0) in a custom designed restrainer where their left pelvic limb was extended and maintained in position with an elastic band. The left pelvic limb was shielded with a cerrobend structure. Animals received a whole body irradiation dose with partial shielding of 15.78 Gy ($LD_{50}/22$) for Study 1 whereas mice were exposed to 15.16 Gy ($LD_{25/22}$) in Study 2. The dose rate of the $^{60}$Co gamma source was fixed at approximately 60 cGy per minute. The in-life portion of both the studies after PSI was 22 days.

Study 1: Mice (N=20/group) were administered once daily with 25HC3S (or vehicle) for 7 consecutive days starting on the day following irradiation (Day 1) by subcutaneous injection between scapulas using a 27 G needle attached to a syringe. The dose volume was 10 mL/kg for all dose routes and the dose was adjusted based on the most recent body weight.

Study 2: Mice (N=16/group) were administered with 25HC3S (or vehicle) for a total of 2 50 mg/kg doses. Animals were given drug (or vehicle) once on the day following irradiation (Day 1) and once on Day 4 by subcutaneous injection between scapulas using a 27 G needle attached to a syringe. The dose volume was 10 mL/kg for all dose routes and the dose was adjusted based on the most recent body weight.

In-Life Monitoring and Measuring Parameters

Mortality checks were recorded concomitantly with the cage-side observations, during all phases of the study. Mortality checks for all animals were also recorded at least once during the night from Day 5 through Day 8. Clinical signs (ill health, behavioral changes, fur color/consistency changes etc.) were also recorded on all surviving animals twice daily throughout observation period (described in Table 10). Additional clinical observations were performed when deemed necessary. All observations were recorded as cage side clinical signs or detailed clinical examination when possible. A detailed clinical examination was performed on each animal at least as follows: prior to animal assignment, one day prior to irradiation (Day −1) then every 3 days throughout the observation period.

Termination

Animals in unrelievable pain or distress were euthanized at the discretion of the Study Director or based on the clinical judgment of the Clinical Veterinarian in consultation, when possible, with the Study Director and the Sponsor. Animals pre-terminally euthanized or found dead were appropriately disposed of without further examination. Euthanasia endpoints are described below.

Euthanasia Criteria

An observation of any one of the following symptoms was justification for euthanasia:
  Inactivity: recumbent in the cage with decreased or absent responsiveness to touch
  Severe hemorrhage from the GI tract or any other orifice in any 24 hours period
  Progressive infection
Observations of a combination of two of the following symptoms were justification for euthanasia:
  Respiratory distress: labored breathing
  Abnormal activity: difficulty with ambulation, decreased food and water intake, self-mutilation, reluctance to move for >24 hours
  Abnormal appearance: rough coat, head down, tucked abdomen, exudates around eyes and/or nose
  Evidence of neurological disorder (for example: severe vestibular syndromes such as head tilt or circling)
Observations of a severe injury or condition, such as but not limited to, bone fracture, progressive tissue necrosis or severe internal bleeding, were also justification for euthanasia but was not observed in either of the two studies At the completion of the study/last observations (Day 22), all surviving animals were euthanized per the standard operating procedures and the carcasses were appropriately disposed.

Results

Figure 10:
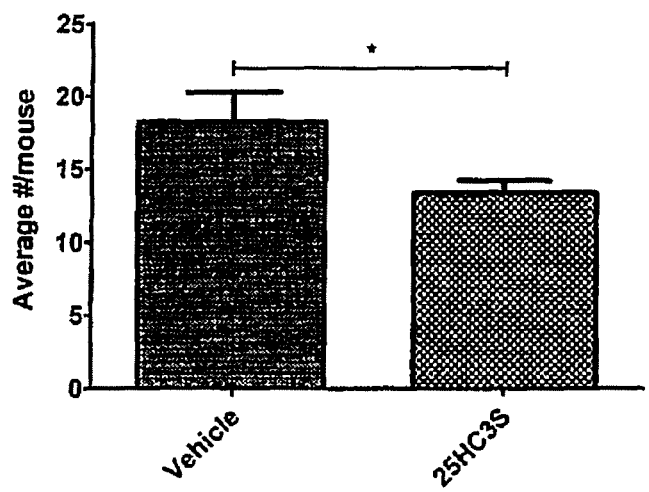
FIG. 10. Study 1: Effects of 25HC3S on clinical signs in a rodent model of GI-ARSs (p<0.05; Student's unpaired t-test). (Radiation dose: 15.78 Gy).

In Study 1, mortality was not significant between the treatment and vehicle groups (data not shown). Survival was 45% (N=9/20) for both groups by Day 7. However, the average number of clinical signs/mice observed throughout Days 5-22 of the in-life portion in 25HC3S-treated animals that survived the entire in-life portion of the study was statistically lower than in the vehicle-treated group. The results are shown in FIG. 10.

Figure 11:
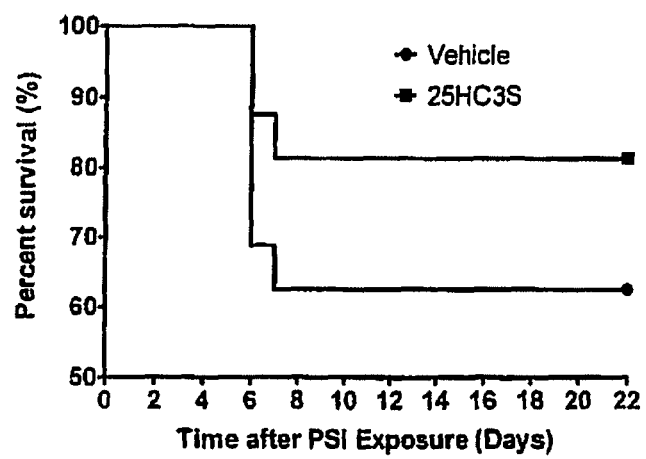
FIG. 11. Study 2: Effects of 25HC3S on mortality in a rodent model of GI-ARS (Radiation dose: 15.16 Gy).

In the following study (Study 2), PSI dose was lowered to an $LD_{25/72}$ as the previous dose in Study 1 was deemed too severe to assess the effect of 25HC3S on mortality. The dose regimen was also reduced to two doses, given on Day 1 and Day 4 of the in-life portion. Survival improved by 18.75% in the 25HC3S-treated group (81.25%) as compared to the vehicle (68.75%), as shown in FIG. 11.

In summary, subcutaneous administration of a solution formulation of 25HC3S at a dose level of 50 mg/kg/dose in male C57BL/6J mice exposed to PBI (15.16 to 15.78 Gy) was associated with reduced clinical signs or improved survival across two independent studies compared to their respective vehicle groups, supportive of efficacy in the treatment of GI-ARS.

TABLE 10

| Clinical signs used to assess animal health |
|---|
| Clinical signs |
| Decreased activity |
| Weak/ataxia |
| Cold to touch |
| Respiration abnormal |
| Hunched back |
| Lying on cage floor |
| Eyes partly closed |
| Dehydration (Skin Turgor slow) |
| Skin pallor |
| Piloerection |
| Walking on tiptoes |

Example 6B. Evaluation of 25HC3S on Survival in a Rodent Model of Surgically-Induced Sepsis (One Representative PD Study)

Material and Methods

Animals

The subjects for the study were 10 male CD rats (12-13 weeks of age, 400-450 g). Animals exhibiting no signs of clinical distress, disease or injury after the acclimatization period were accepted for the study and received routine animal care throughout.

Formulation

A solution formulation of 25HC3S sodium salt and its respective vehicle was used for the study. The Vehicle was a solution of 40 mg/mL hydroxypropyl betadex with 10 mM sodium phosphate buffer in 70% (v/v) of 0.9% (w/v) sodium chloride and 30% (v/v) of sterile water. 25HC3S sodium salt was pre-dissolved into the Vehicle solution to result in a drug concentration of 5 mg/mL. The 25HC3S solution was readyto-use at the start of dosing. Both the vehicle and 25HC3S solution were stored at room temperature. Before dosing, the 25HC3S solution was confirmed to be clear and void of any precipitation. Otherwise, if precipitation was observed, the solution was to be sonicated at room temperature for 10 minutes to dissolve particulates.

Cecum Ligation Puncture (CLP) Surgery and 25HC3S Administration

The CLP procedure is an established and widely-used approach to investigate the progression and characteristics of clinical sepsis. On the day of surgery, animals were weighed and monitored for their baseline temperature. Animals were anesthetized with isoflurane and depth of anesthesia was checked by toe-pinching. Dipyrone (an analgesic) was given subcutaneously prior to surgery. A 2 cm midline incision was made and the cecum exteriorized. The cecum was loosely ligated at 10% of its length, just distal to the ileocecal junction. A 14 G needle was then used to puncture the cecum and then subsequently cut with a 1.3 mm scalpel blade, along its anti-mesenteric side to get a hole of 3 mm in diameter. Technique was repeated about 2-3 cm away from first puncture site. Half the fecal material of cecum was gently squeezed out to ensure the patency of the perforation sites. The cecum was returned to the abdominal cavity, and abdominal incision was closed with Vicryl 4-0 for muscle layers; the skin was closed with staples. Animals were put on a heating pad for recovery. Within 30 minutes after surgery, animals (N=5/group) were given 30 mg/kg of 25HC3S (or vehicle) at an injection volume of 5 mL/kg by subcutaneous administration in the scapular region of the back. Animals were returned to their cages after gaining full consciousness. Treatment of 25HC3S (or vehicle) was done only on the day of surgery and was not repeated in the rest of study Monitoring and Measuring Parameters Rats were monitored for survival for 3 days after CLP surgery and 25HC3S treatment. Animal checks for mortality were performed twice daily during the observation period. Animals were examined for any altered clinical signs, including gross motor and behavioral activity and observable changes in appearance. Body weight, body temperature and their general appearance were graded every 24 hours to generate an accumulated disease score, consisting of the following:

Table 11

"Clinical Signs" used to generate an accumulated disease score

| | Score given (0-3) | | | |
|---|---|---|---|---|
| Clinical Signs | 0 | 1 | 2 | 3 |
| Body Condition (Dehydration) | Normal | Under-conditioned/slight dehydration | Emaciated/moderate dehydrated | Very dehydration |
| Appearance | Normal | Ruffled | Hunched | Hunched with tremors |
| Breathing | Normal | Fast rate | Irregular | Difficult/labored |

Termination

Animals were monitored for mortality, "clinical signs" and pain level. If they seemed reached a score of "3" in any one of the categories or a combination of "4" of the signs from any two categories of the "Clinical Signs" from Table 11, they were considered to have reached the clinical endpoint and were considered "dead" for survival curve analyses and humanely euthanized. In addition, 3 days after CLP surgery, all remaining rats were weighed and humanely euthanized via $CO_2$ inhalation. A general necropsy was performed to check the ligation site.

Results

Figure 12:
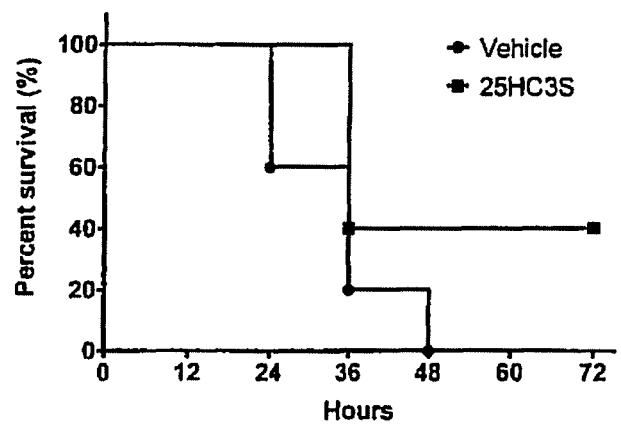
FIG. 12. Effects of 25HC3S on mortality in rats that underwent CLP surgery-induced sepsis (p=0.0975; Log-rank/Mantel-Cox test).

The mortality results are shown in FIG. 12. Two days (48 hours) after CLP surgery and dosing, 100% (N=5/5) of the vehicle-treated rats died. In marked contrast, only 60% (N=3/5) of rats that received 25HC3S treatment had died (p-value=0.0975; Log-rank/Mantel-Cox test) at the end of the study duration (3 days or 72 hours). In summary, a single dose of 25HC3S improved survival in a rat model of sepsis by surgically-induced endotoxin exposure.

Example 6C-D. Preclinical Pharmacokinetic Injection Studies

Several PK injection studies have been performed in Hannover Wistar rats and Beagle dogs, using the 25HC3S formulations, as summarized in Table 9 above. Injection routes of administration used were intramuscular, intravenous or subcutaneous. The following example is a representative injection study.

Beagle dogs (n=5/dose group) received a single intravenous bolus injection or a single subcutaneous injection. The parenteral solution that was tested included 25 mg/mL of 25HC3S sodium salt in vehicle (200 mg/mL hydroxypropyl betadex with 10 mM sodium phosphate buffers, in water). The intravenous dose level of 2.5 mg/kg was administered in a dose volume of 0.1 mL/kg whereas the subcutaneous injection dose level of 20 mg/kg was administered in a dose volume of 0.8 mL/kg. Whole blood samples were collected at pre-dose, 0.5, 1, 2, 4, 8, 12, 24, 32 and 48 hours (h) post dose and the resulting plasma samples underwent analyses to quantify 25HC3S levels. During the in-life period, animals were observed daily for mortality and moribundity with clinical examinations conducted daily. There were no observable clinical signs in both groups.

For intravenous administration, the maximal concentration was observed at the first time point, 0.5 h ($C_{max}$=439 ng/mL), and the mean $AUC_{last}$ was 478 ng*hr/mL with no observable levels in most animals (n=4) at 8 h. Following subcutaneous administration, rapid absorption was observed at 0.5 h and with low but detectable levels of 25HC3S observed in all animals at 12 h. The maximum observed concentration ($C_{max}$=3936 ng/mL) was observed at a mean time to maximum concentration of 1.8 h and the $AUC_{last}$ was 19503 ng*hr/mL (Table 12). The observed bioavailability was calculated to be 0.7 by subcutaneous administration.

TABLE 12

Mean (SD) Pharmacokinetic parameters following a single dose with 25HC3S in beagles (N = 5)

| | Route of Administration | |
|---|---|---|
| Parameter | Intravenous | Subcutaneous |
| Cmax (mg/mL) | 439 (147) | 3936 (1428) |
| Tmax (hr) | 0.5 (0) | 1.8 (1.3) |
| AUCall (ng*hr/mL) | 489 (464) | 19676 (3716) |

Example 7. A 14-Day Subcutaneous Injection Study of 25HC3S in Beagle Dogs

The objectives of this study were to evaluate the potential toxicity of 25HC3S when administered once daily by subcutaneous injection to Beagle dogs for 14 consecutive days.

25HC3S sodium salt in the vehicle (250 mg/mL hydroxypropyl-beta-cyclodextrin with 10 mM sodium phosphate buffer [approximate pH 7.6] in sterile water for irrigation) was administered via subcutaneous injection in the dorsoscapular area once daily for 14 consecutive days to 3 groups (Groups 2-4) of Beagle dogs. Dosage levels were 3, 10, and 30 mg/kg/day for Groups 2, 3, and 4, respectively. A concurrent control group (Group 1) received the vehicle on a comparable regimen. The dose volume was 1, 0.1, 0.33, and 1 mL/kg for Groups 1, 2, 3, and 4, respectively. Each group consisted of 4 males and 4 females. The animals were observed twice daily for mortality and moribundity. Clinical examinations (including injection site observations) were performed once daily for at least 6 days, including the day of randomization, prior to randomization, prior to dose administration, immediately following dose administration, and at approximately 2 hours following dose administration. Blood samples for toxicokinetic evaluation were collected from all animals prior to dosing (study day 0 only) and at 0.5, 1, 2, 4, 8, and 24 hours after dosing on study days 0 and 13.

All animals survived to the scheduled necropsy. There were no drug-related clinical observations or effects on body weights, food consumption, hematology, coagulation, serum chemistry, urinalysis, ophthalmology, or electrocardiography. There were no drug-related macroscopic or microscopic findings or alterations in organ weights at the scheduled necropsy.

Based on the results of this study, once daily administration of 25HC3S via subcutaneous injection in the dorsoscapular region to Beagle dogs for 14 consecutive days was well tolerated at dosage levels of 3, 10, and 30 mg/kg/day. Macroscopic and microscopic findings noted at the injection sites (fibroplasia, hemorrhage, inflammation, and necrosis) were unique to or were more frequent and/or severe in the control animals administered the cyclodextrin vehicle, while no injection site changes appeared directly attributable to administration of 25HC3S. Therefore, the no-observed-adverse-effect level (NOAEL) was considered to be 30 mg/kg/day. This dosage level corresponded to a mean $AUC_{last}$ of 19,877 ng*hr/mL and mean $C_{max}$ of 7,753 ng/mL.

Example 8. Intramuscular Clinical Trial

This example describes a randomized, double-blind, placebo-controlled, safety and pharmacokinetic study of a parenteral formulation of 25HC3S. The study involved the administration of 25HC3S sodium salt to healthy subjects via intramuscular injections (IM) as i) single ascending doses (SAD) in the range of 30-300 mg and as ii) a multiple ascending dose (MAD) study using multiple IM doses of 150 mg administered daily for 5 days (see Table 13). All subjects were male, with an age range of 19-36 years.

TABLE 13

Study protocol

| Type of Study | Objective(s) | Trial Design | Study Population | Dose/Regimen | Route | # of Subjects |
|---|---|---|---|---|---|---|
| Safety & PK | Single and Multiple Ascending Dose Safety & PK | Randomized, Double-Blind, Placebo-Controlled | Healthy Subjects | Parenteral (30 mg/mL) SAD 30 mg 90 mg 150 mg 300 mg MAD: 150 mg × 5 days | IM | 6 6 6 6 10 |

The parenteral solution was 30 mg/mL 25HC3S sodium salt reconstituted with a vehicle solution of 250 mg/mL hydroxypropyl betadex, NF; 0.276 mg/mL of sodium phosphate monobasic monohydrate, USP and 1.136 mg/mL sodium phosphate dibasic anhydrous, USP, in sterile water for injection, USP.

In Part A of the study (SAD), a parenteral dose of 25HC3S or matching placebo was administered intramuscularly (IM) to cohorts of 6 healthy subjects (4 randomized to 25HC3S and two randomized to matching placebo on a double-blind basis). The initial dose was 30 mg and subsequent cohorts of 6 different subjects received doses of 90, 150, and 300 mg of 25HC3S. A total of 16 subjects received 25HC3S and 8 received placebo in Part A. In Part B (MAD), a parenteral dose of 150 mg 25HC3S or matching placebo was administered IM once daily for 5 days, altering injection sites, to a single cohort of 10 healthy subjects (8 randomized to 25HC3S and two randomized to matching placebo on a double-blind basis; see Table 14).

Safety assessments included periodic monitoring of routine vital signs, safety laboratory tests and 12 lead ECG collection. Subjects completed a screening phase, treatment and an end-of-study visit. Dose escalation to the next dose level in Part I and Part II of the study was undertaken following review of the preceding dose results.

Results

Figure 13:
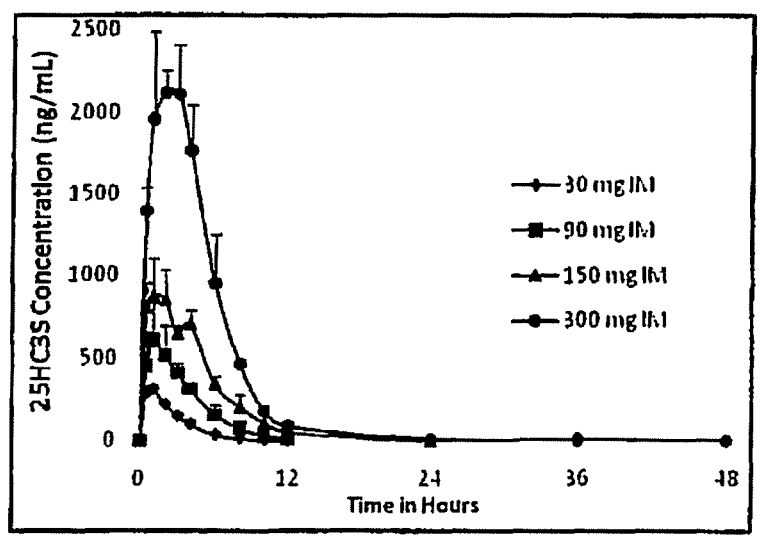
FIG. 13. Concentration (ng/ml) in blood samples following injection of 30, 90, 150 and 300 mg of 25HC3S.
Figure 14:
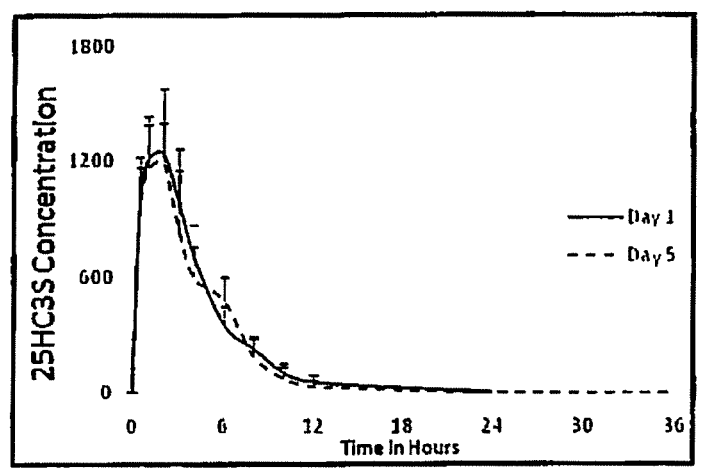
FIG. 14. Concentration (ng/ml) of 25HC3S in blood samples on days 1 and 5.

Following IM administration, rapid absorption of 25HC3S was observed with detectable drug levels at the first time point of 0.5 hour for all cohorts. $C_{max}$ (maximum (or peak) serum concentration) and AUC (area under the curve) were observed to increase in a linear fashion with increasing 25HC3S dose (FIG. 13). No accumulation of 25HC3S was observed following administration of five daily doses (FIG. 14).

Pain intensity (measured on a 0-10 numeric rating scale) was assessed after each injection, and the injection sites were examined for tenderness, redness, bruising, swelling and induration at specified time points after injection. In general, pain intensity was maximal at 5-10 min after injection and had resolved by 1 hour after injection. The mean pain intensity ranged from 0.8 to 3.5 and had little relationship to dose. Mild tenderness at the injection site was observed in 7 of the 24 subjects in Part A and in 9 of the 10 subjects in Part B. Other physical findings at the injection sites were infrequent (one injection site with bruising and one site with redness).

SUMMARY

The safety of 25HC3S given by intramuscular injection as a single dose and as a multiple dose was studied. Other than mild injection site tenderness, there were no drug-related adverse events in either the single dose group or in the multiple dose group, other than injection site tenderness, and all 34 subjects completed the trial as planned without any untoward events.

Single IM injections into the buttock were well tolerated at doses of 30, 90, 150, and 300 mg, and systemic exposure increased linearly with the dose of 25HC3S administered. However, no accumulation of 25HC3S was observed upon repeat dosing in the multiple dose cohort.

Example 9. Infusion Compatibility

25HC3S for Injection is a sterile powder, for injection solution. The 25HC3S stability with the 10 mL glass vial and FluroTec® coated stopper was studied up to 12 months at 2-8° C., 6 months at 25° C./60% RH, and 6 months at 40° C./75% RH with vials stored in the inverted orientation. Based on these stability data, it was concluded that there is good compatibility between 25HC3S and the container closure system, as shown below.

In a similar manner, the Vehicle for 25HC3S for Injection (Vehicle) stability with the 10 mL glass vial and FluroTec® coated stopper was studied up to 12 months at 2-8° C., 6 months at 25° C./60% RH, and 6 months at 40° C./75% RH with vials stored in the inverted orientation. The Vehicle was 250 mg/mL HPbCD with 10 mM phosphate buffers. Based on these stability data, it was concluded that there is good compatibility between the Vehicle and the container closure system, as shown below.

Compatibility of Constituted 25HC3S Solution with 5% Dextrose and 0.9% Sodium Chloride for Infusion and Two Kinds of Infusion Sets After constitution with Vehicle, the 30 mg/mL 25HC3S product was diluted into 100 mL of 5% dextrose injection, USP or 0.9% sodium chloride injection, USP, and was administered to subjects as an IV infusion ranging from a 30 mg to 150 mg 25HC3S dose. This was accomplished by adding 1.0 mL (for the 30 mg dose) or 5.0 mL (for the 150 mg dose), or any volume in between, of the 30 mg/mL 25HC3S product into a 100 mL dextrose or sodium chloride infusion bag. The entire admixture content in the infusion bag was infused into the subject over approximately 2 hours at a rate of 50 mL/hour.

A physical and chemical compatibility study was conducted at a 30 mg, 48 mg and 300 mg 25HC3S dose in 5% dextrose and 0.9% sodium chloride infusion bags. Descriptions of the two infusion solutions used to dilute the constituted 25HC3S for Injection are listed in Table 14. Descriptions of the two kinds of infusion sets tested with 25HC3S product diluted in 5% dextrose and 0.9% sodium chloride are listed in Table 15. The tubing in catalog number 2H8480 infusion set was composed of polyvinylchloride (PVC), while the tubing in catalog number 2C8858 was polyethylene lined except for a short pump segment (approximately 12 inches) which was composed of PVC.

TABLE 14

Description of Infusion Solutions

| Manufacturer/Catalog Number | Description | Size of Bag |
|---|---|---|
| Hospira NDC 0409-7923-23 | 5% Dextrose Injection, USP | 100 mL |
| Hospira NDC 0409-7984-23 | 0.9% Sodium Chloride Injection, USP | 100 mL |

TABLE 15

Description of Infusion Sets

| Manufacturer/Catalog Number | Description | Flow Rate | Length |
|---|---|---|---|
| Baxter 2H8480 | Non-DEHP Polyvinylchloride Solution Set with DUO-VENT spike, with Clearlink luer activated valve, with 0.22 micron filter | Approximately 10 drops per mL | 103 inches |
| Baxter 2C8858 | Paclitaxel set with polyethylene lined tubing, non-DEHP pump segment (polyvinylchloride), with Clearlink luer activated valve, with 0.22 micron filter | Approximately 10 drops per mL | 107 inches |

25HC3S for Injection and Vehicle for 25HC3S for Injection, that had been stored at 2-8° C. for approximately 16 months, were used for the compatibility study. After constitution, 30 mg (1.0 mL of constituted product), 48 mg (1.6 mL of constituted product) or 300 mg (10 mL of constituted product) were added to 100 mL infusion bags of 5% dextrose and 0.9% sodium chloride, mixed thoroughly, and stored for 24 hours at room temperature and at 2-8° C. The Hospira labeled 100 mL dextrose and sodium chloride infusion bags had an overfill, so the average fill was actually 107 mL. Taking into consideration the overfill per infusion bag and the additional volume introduced by adding the constituted 25HC3S product to each bag, the expected concentrations of 25HC3S were 0.28 mg/mL, 0.44 mg/mL, and 2.56 mg/mL in the infusion bags. Two kinds of infusion sets were then attached to the drug containing infusion bags, and the entire contents were eluted through the infusion sets at approximately 50 mL/hour at room temperature. Samples were collected from the 25HC3S prepared infusion bags at T=0 and at 24 hours, and from the total eluent passed through the infusion sets, and tested for 25HC3S concentration using HPLC. Solution visual appearance, osmolality (using method USP<785>), and pH (using method USP<791>) were also measured on the collected samples.

The compatibility results for 25HC3S with 5% dextrose and 0.9% sodium chloride, and with the two kinds of infusion sets, are shown in Table 16 and Table 17, respectively.

TABLE 16

Stability of 25HC3S Diluted and Stored in 5% Dextrose Infusion Bag for 24 Hours and Eluted Through Two Kinds of Infusion Sets (Potency)

| Approximate 25HC3S Concentration in Infusion Bag (mg/mL) | Dextrose Infusion Bag ID | T = 0 Conc. (mg/mL) | 24 Hours at RT Concentration in mg/mL and (% Remaining Compared to T = 0) | 24 Hours at 2-8° C. Concentration in mg/mL and (% Remaining Compared to T = 0) | After Storage in Infusion Bag and Collection from Infusion Set Concentration in mg/mL and (% Remaining Compared to T = 0) |
|---|---|---|---|---|---|
| 0.28 | 1 | 0.276 | 0.276 (100.0%) | | Baxter 2H8480 0.276 (100.0%) |
| | 2 | 0.277 | 0.277 (100.0%) | | Baxter 2C8858 0.277 (100.0%) |
| | 3 | 0.280 | | 0.280 (100.0%) | Baxter 2H8480 0.280 (100.0%) |
| | 4 | 0.279 | | 0.280 (100.4%) | Baxter 2C8858 0.280 (100.4%) |
| 0.44 | 1 | 0.447 | 0.447 (100.0%) | | Baxter 2H8480 0.448 (100.2%) |
| | 2 | 0.442 | 0.442 (100.0%) | | Baxter 2C8858 0.442 (100.0%) |
| | 3 | 0.439 | | 0.438 (99.8%) | Baxter 2H8480 0.440 (100.2%) |
| | 4 | 0.439 | | 0.440 (100.2%) | Baxter 2C8858 0.440 (100.2%) |
| 2.56 | 1 | 2.500 | 2.470 (98.8%) | | Baxter 2H8480 2.480 (99.2%) |
| | 2 | 2.510 | 2.520 (100.4%) | | Baxter 2C8858 2.545 (101.4%) |
| | 3 | 2.530 | | 2.550 (100.8%) | Baxter 2H8480 2.540 (100.4%) |
| | 4 | 2.525 | | 2.530 (100.2%) | Baxter 2C8858 2.535 (100.4%) |

TABLE 17

Stability of 25HC3S Diluted and Stored in 0.9% Sodium Chloride Infusion Bag for 24 Hours and Eluted Through Two Kinds of Infusion Sets (Potency)

| Approximate 25HC3S Concentration in Infusion Bag (mg/mL) | Sodium Chloride Infusion Bag ID | T = 0 Conc. (mg/mL) | 24 Hours at RT Concentration in mg/mL and (% Remaining Compared to T = 0) | 24 Hours at 2-8° C. Concentration in mg/mL and (% Remaining Compared to T = 0) | After Storage in Infusion Bag and Collection from Infusion Set Concentration in mg/mL and (% Remaining Compared to T = 0) |
|---|---|---|---|---|---|
| 0.28 | 1 | 0.273 | 0.272 (99.6%) | | Baxter 2H8480 0.272 (99.6%) |
| | 2 | 0.274 | 0.274 (100.0%) | | Baxter 2C8858 0.274 (100.0%) |
| | 3 | 0.274 | | 0.275 (100.4%) | Baxter 2H8480 0.275 (100.4%) |
| | 4 | 0.275 | | 0.275 (100.0%) | Baxter 2C8858 0.275 (100.0%) |
| 0.44 | 1 | 0.434 | 0.434 (100.0%) | | Baxter 2H8480 0.433 (99.8%) |
| | 2 | 0.424 | 0.424 (100.0%) | | Baxter 2C8858 0.424 (100.0%) |

TABLE 17-continued

Stability of 25HC3S Diluted and Stored in 0.9% Sodium Chloride Infusion Bag
for 24 Hours and Eluted Through Two Kinds of Infusion Sets (Potency)

| Approximate 25HC3S Concentration in Infusion Bag (mg/mL) | Sodium Chloride Infusion Bag ID | T = 0 Conc. (mg/mL) | 24 Hours at RT Concentration in mg/mL and (% Remaining Compared to T = 0) | 24 Hours at 2-8° C. Concentration in mg/mL and (% Remaining Compared to T = 0) | After Storage in Infusion Bag and Collection from Infusion Set Concentration in mg/mL and (% Remaining Compared to T = 0) |
|---|---|---|---|---|---|
| | 3 | 0.434 | | 0.434 (100.0%) | Baxter 2H8480 0.434 (100.0%) |
| | 4 | 0.425 | | 0.425 (100.0%) | Baxter 2C8858 0.426 (100.2%) |
| 2.56 | 1 | 2.450 | 2.500 (102.0%) | | Baxter 2H8480 2.460 (100.4%) |
| | 2 | 2.530 | 2.525 (99.8%) | | Baxter 2C8858 2.520 (99.6%) |
| | 3 | 2.530 | | 2.510 (99.2%) | Baxter 2H8480 2.530 (100.0%) |
| | 4 | 2.525 | | 2.520 (99.8%) | Baxter 2C8858 2.520 (99.8%) |

The 25HC3S concentrations in 5% dextrose after 24 hours at room temperature and at 2-8° C., and after elution through the infusion sets were all within 1.4% of the target concentrations of the initial T=0 time point. Similar 25HC3S stability in 0.9% sodium chloride was observed, where after 24 hours at room temperature and at 2-8° C., and after elution through the infusion sets all the concentrations were within 2.0% of the target concentrations of the initial T=0 time point.

Osmolality and pH data for 25HC3S in 5% dextrose at T=0 and 24 hours, and after elution through the two kinds of infusion sets are shown in Table 18. Osmolality and pH data for 25HC3S in 0.9% sodium chloride at T=0 and 24 hours, and after elution through two kinds of infusion sets are shown in Table 19. The osmolality data, for both the dextrose and sodium chloride drug containing solutions, showed no consistent trends over time in the infusion bag or after elution through the infusion sets. The pH of the dextrose drug containing solutions also showed no trends over time or after elution through the infusion sets. The pH of the sodium chloride drug containing solution at approximately 0.28 mg/mL 25HC3S showed an approximate decrease of 0.5 of a pH unit over 24 hours in the infusion bags, and appeared to decrease by approximately a tenth of a pH after elution through the infusion sets. The pH of the sodium chloride drug containing solution at approximately 0.44 mg/mL 25HC3S showed no consistent trends over time in the infusion bags, but appeared to decrease by a few tenths of a pH after elution through the infusion sets. The pH of the sodium chloride drug containing solution at approximately 2.56 mg/mL 25HC3S showed a slight decrease by a tenth of a pH over time in the infusion bags, and appeared to drop by a few tenths of a pH after elution through the infusion sets.

The 25HC3S solutions in dextrose and sodium chloride, at all three concentrations, remained as clear and colorless solutions, after 24 hours in the infusion bags, and after elution through the infusion sets.

The appearance of the infusion bags and infusions sets also remained the same before and after use with the 25HC3S solutions.

The compatibility of 25HC3S, at 30 mg, 48 mg, and 300 mg, as admixtures with 100 mL of dextrose and sodium chloride, and with two kinds of infusion sets, has been demonstrated by the acceptable 25HC3S concentration, pH, osmolality, and physical appearance stability data.

TABLE 18

Stability of 25HC3S Diluted and Stored in 5% Dextrose Infusion Bag for
24 Hours and Eluted Through Two Kinds of Infusion Sets (Osmolality and pH)

| Approximate 25HC3S Concentration in Infusion Bag (mg/mL) | Dextrose Infusion Bag ID | T = 0 Osmolality (mmol/kg) and pH | 24 Hours at RT Osmolality (mmol/kg) and pH | 24 Hours at 2-8° C. Osmolality (mmol/kg) and pH | After Storage in Infusion Bag and Collection from Infusion Set Osmolality (mmol/kg) and pH |
|---|---|---|---|---|---|
| 0.28 | 1 | 247 7.09 | 252 7.12 | | Baxter 2H8480 252 6.99 |
| | 2 | 250 7.03 | 249 7.05 | | Baxter 2C8858 252 7.04 |
| | 3 | 251 7.10 | | 250 7.09 | Baxter 2H8480 251 6.95 |

TABLE 18-continued

Stability of 25HC3S Diluted and Stored in 5% Dextrose Infusion Bag for
24 Hours and Eluted Through Two Kinds of Infusion Sets (Osmolality and pH)

| Approximate 25HC3S Concentration in Infusion Bag (mg/mL) | Dextrose Infusion Bag ID | T = 0 Osmolality (mmol/kg) and pH | 24 Hours at RT Osmolality (mmol/kg) and pH | 24 Hours at 2-8° C. Osmolality (mmol/kg) and pH | After Storage in Infusion Bag and Collection from Infusion Set Osmolality (mmol/kg) and pH |
|---|---|---|---|---|---|
| | 4 | 250 7.04 | | 253 7.04 | Baxter 2C8858 252 6.99 |
| 0.44 | 1 | 255 6.83 | 256 6.91 | | Baxter 2H8480 253 6.91 |
| | 2 | 254 6.81 | 253 6.90 | | Baxter 2C8858 253 6.90 |
| | 3 | 256 6.82 | | 254 6.96 | Baxter 2H8480 257 6.91 |
| | 4 | 255 6.88 | | 257 6.93 | Baxter 2C8858 255 6.93 |
| 2.56 | 1 | 258 6.04 | 257 6.12 | | Baxter 2H8480 261 6.01 |
| | 2 | 247 6.12 | 250 6.06 | | Baxter 2C8858 251 6.00 |
| | 3 | 247 6.29 | | 246 6.11 | Baxter 2H8480 247 5.99 |
| | 4 | 247 6.26 | | 251 6.14 | Baxter 2C8858 248 6.10 |

TABLE 19

Stability of 25HC3S Diluted and Stored in 0.9% Sodium Chloride Infusion Bag
for 24 Hours and Eluted Through Two Kinds of Infusion Sets (Osmolality and pH)

| Approximate 25HC3S Concentration in Infusion Bag (mg/mL) | Sodium Chloride Infusion Bag ID | T = 0 Osmolality (mmol/kg) and pH | 24 Hours at RT Osmolality (mmol/kg) and pH | 24 Hours at 2-8° C. Osmolality (mmol/kg) and pH | After Storage in Infusion Bag and Collection from Infusion Set Osmolality (mmol/kg) and pH |
|---|---|---|---|---|---|
| 0.28 | 1 | 278 6.39 | 275 5.93 | | Baxter 2H8480 276 5.78 |
| | 2 | 277 6.43 | 277 5.92 | | Baxter 2C8858 276 5.83 |
| | 3 | 277 6.45 | | 276 5.87 | Baxter 2H8480 277 5.81 |
| | 4 | 278 6.40 | | 276 5.99 | Baxter 2C8858 276 5.78 |
| 0.44 | 1 | 277 7.30 | 280 7.33 | | Baxter 2H8480 286 7.09 |
| | 2 | 279 7.43 | 280 7.41 | | Baxter 2C8858 288 7.20 |
| | 3 | 284 7.21 | | 281 7.43 | Baxter 2H8480 282 7.13 |
| | 4 | 280 7.44 | | 281 7.19 | Baxter 2C8858 281 7.16 |

TABLE 19-continued

Stability of 25HC3S Diluted and Stored in 0.9% Sodium Chloride Infusion Bag
for 24 Hours and Eluted Through Two Kinds of Infusion Sets (Osmolality and pH)

| Approximate 25HC3S Concentration in Infusion Bag (mg/mL) | Sodium Chloride Infusion Bag ID | T = 0 Osmolality (mmol/kg) and pH | 24 Hours at RT Osmolality (mmol/kg) and pH | 24 Hours at 2-8° C. Osmolality (mmol/kg) and pH | After Storage in Infusion Bag and Collection from Infusion Set Osmolality (mmol/kg) and pH |
|---|---|---|---|---|---|
| 2.56 | 1 | 282<br>6.20 | 282<br>6.01 | | Baxter 2H8480<br>283<br>5.81 |
| | 2 | 282<br>6.10 | 282<br>5.86 | | Baxter 2C8858<br>279<br>5.83 |
| | 3 | 282<br>6.07 | | 283<br>5.93 | Baxter 2H8480<br>283<br>5.72 |
| | 4 | 281<br>6.11 | | 283<br>5.96 | Baxter 2C8858<br>283<br>5.70 |

Example 10. Topical Formulations

Topical formulations of 25HC3S were prepared using custom-made compositions.

Evaluation of Formulations

Compositions listed were evaluated for texture, homogeneity and physical stability at room temperature by monitoring any sign of phase separation.

Custom-Made Compositions

Materials:

Carbopol® 971P NF and Carbopol® 974P NF were received from Lubrizol. Tween® 80 was received from CRODA. All other additives were purchased from Spectrum.

Preparation of Formulations:

All formulations were water based gels. Carbopol® was used as a thickening agent. Oleic acid, HPbCD, and propylene glycol (PG) were used as the skin penetration enhancers. Tween® was used as a surfactant. Trolamine was used to adjust pH of the formulation.

The 25HC3S was dissolved in 25% solution of Hydroxypropyl beta cyclodextrin (HPbCD), and then mixed with the rest of the additives. The drug mixtures were added to the thickening agent (Carbopol®) prior to its complete gelling.

Formulations are listed in Table 20. Table 21 shows the appearance and physical stability of the formulations. Physical stability of each formulation is shown since preparation date.

TABLE 20

| | Formulation ID | |
|---|---|---|
| Components, % w/w | 006 | 007 |
| 25HC3S | 1.3 | 2 |
| Carbopol ® 971P | 1 | — |
| Carbopol ® 974P | — | 1 |
| Trolamine | 2.5 | 2 |
| HPbCD | 6 | 6 |
| PG | 25 | 20 |
| Tween ® 80 | 6 | 5 |
| Oleic acid | 6 | 5 |
| Methyl paraben | 0.2 | — |
| Water | 52 | 60 |

TABLE 21

Appearance and Physical Stability of Compositions listed in Table 19

| Formulation ID | Physical Appearance | Physical stability | |
|---|---|---|---|
| | | RT | 1 day, 32° C. |
| 006 | Gel | Stable, 3 months | Vehicle: phase separated |
| 007 | Gel | Stable, 3 months | Phase separated, flows after 1 hour |

Example 11. Effect of Various Concentrations of Phosphate and Borate Buffers on the Chemical and Physical Stability of 25HC3S at 30 mg/mL in 250 mg/mL HPBCD Formulations

BACKGROUND

A total of six 25HC3S formulations at 30 mg/mL in 250 mg/mL of 2-hydroxypropyl beta cyclodextrin (HPBCD) containing 10, 20, 50 and 100 mM phosphate buffers at pH 7.5 to 8.1 and 10 and 50 mM borate buffers at pH 9.4 were prepared for the stability study. The chemical stability (measured as % remaining of 25HC3S) and physical stability (osmolality, pH and appearance) of the formulations were monitored under accelerated conditions for up to 7 days at 80° C. and up to 29 days at 60° C.

Materials

25HC3S was sieved through a 40 mesh screen and used for formulation preparation and for calibration standards preparation for HPLC analysis. Kleptose® HPB (HPBCD, hydroxypropyl betadex, parenteral grade, EP-USP/NF grade was obtained from Roquette America, Inc. Sodium phosphate, monobasic, monohydrate ($NaH_2PO_4.H_2O$) USP, BP grade was obtained from Spectrum Chemicals. Sodium phosphate dibasic, anhydrous ($Na_2HPO_4$) USP, FCC grade and sodium tetraborate decahydrate ($Na_2B_4O_7.10H_2O$), ACS reagent grade were obtained from J. T Baker. Sterile Water for Injection, USP was obtained from APP Pharmaceuticals. The container closure system consisted of 2 mL glass vials (Afton Scientific), Flurotec coated stoppers (West Pharmaceuticals) and aluminum seals.

Experimental

(1) Formulation Preparation and Stability Sample Set-Up

Two stock solutions of phosphate buffer at 100 and 200 mM at pH 7.4 and 7.3, respectively and one borate buffer at 100 mM at pH 9.3 were prepared (Tables 22A and 22B) and used for 250 mg/mL HPBCD vehicles preparation (Table 23).

Approximately 1200 mg each of 25HC3S was weighed into 40 mL volumetric flasks and diluted to volume with the six HPBCD vehicles containing 10-100 mM phosphate buffers or 10 and 50 mM borate buffers, respectively (Table 24). The final concentration of 25HC3S was 30 mg/mL (wt/volume, without adjusting for API purity). Aliquots of 2 mL of each formulation were filled into 2 mL glass vials, stoppered and sealed for stability sample set-up at 60° C. and 80° C. to study the effect of phosphate buffer (pH 7.5-8.1) and borate buffer (pH 9.4) at various buffer concentrations on the stability of the HPBCD formulations (Table 26).

TABLE 22A

Preparation of Phosphate Buffer Stock Solutions at 100 and 200 mM

| $NaH_2PO_4 \cdot H_2O$ (mg) | $Na_2HPO_4$, Anhydrous (mg) | QS to Volume (mL) with Sterile Water for Injection | Final Buffer Concentration (mM) | Measured pH |
|---|---|---|---|---|
| 552.4 | 2272.2 | 100 | 200 | 7.28 |
| 50 mL of 200 mM stock solution above | NA | 100 | 100 | 7.36 |

TABLE 22B

Preparation of Borate Buffer Stock Solution at 100 mM

| $Na_2B_4O_7 \cdot 10H_2O$ (mg) | QS to Volume (mL) with Sterile Water for Injection | Final Buffer Concentration (mM) | Measured pH |
|---|---|---|---|
| 3813.8 | 100 | 100 | 9.31 |

TABLE 23

Preparation of Six Vehicles with 250 mg/mL HPBCD Containing 10, 20, 50 and 100 mM Phosphate Buffers or 10 and 50 mM Borate Buffers

| Vehicle # | HPBCD (mg) | Buffer Type | Stock Buffer Conc. (mM) | Stock Buffer Volume (mL) | QS with Sterile Water For Injection (mL) | Vehicle Composition Final Buffer Conc. (mM) | Vehicle Composition Final HPBCD Conc. (mg/mL) |
|---|---|---|---|---|---|---|---|
| 1 | 12502.9 | Phosphate | 100 | 5 | 50 | 10 | 250 |
| 2 | 12500.3 | Phosphate | 100 | 10 | 50 | 20 | 250 |
| 3 | 12502.5 | Phosphate | 100 | 25 | 50 | 50 | 250 |
| 4 | 12503.5 | Phosphate | 200 | 25 | 50 | 100 | 250 |
| 5 | 12501.8 | Borate | 100 | 5 | 50 | 10 | 250 |
| 6 | 12500.4 | Borate | 100 | 25 | 50 | 50 | 250 |

TABLE 24

Preparation of Six 25HC3S Formulations at 30 mg/mL in 250 mg/mL of HPBCD Containing 10, 20, 50 and 100 mM Phosphate Buffers at Approximate pH of 7.4 or 10 and 50 mM Borate Buffer at Approximate pH of 9.3

| Formulation # | 25HC3S (mg) | Vehicle Composition HPBCD (mg/mL) | Vehicle Composition Buffer/ Concentration | QS with Vehicle to Volume (mL) | Final 25HC3S Concentration (mg/mL) |
|---|---|---|---|---|---|
| 1 | 1201.0 | 250 | Phosphate/10 mM | 40 | 30 |
| 2 | 1201.4 | 250 | Phosphate/20 mM | 40 | 30 |
| 3 | 1201.2 | 250 | Phosphate/50 mM | 40 | 30 |

TABLE 24-continued

Preparation of Six 25HC3S Formulations at 30 mg/mL in 250 mg/mL of HPBCD Containing 10, 20, 50 and 100 mM Phosphate Buffers at Approximate pH of 7.4 or 10 and 50 mM Borate Buffer at Approximate pH of 9.3

| Formulation # | 25HC3S (mg) | Vehicle Composition HPBCD (mg/mL) | Buffer/ Concentration | QS with Vehicle to Volume (mL) | Final 25HC3S Concentration (mg/mL) |
|---|---|---|---|---|---|
| 4 | 1200.9 | 250 | Phosphate/100 mM | 40 | 30 |
| 5 | 1200.8 | 250 | Borate/10 mM | 40 | 30 |
|   | 1201.3 | 250 | Borate/50 mM | 40 | 30 |

TABLE 25

Stability Sample Set Up for the Six Formulations

| Temperature | Days (2 Vials per Time Point per Formulation) |   |   |   |   |
|---|---|---|---|---|---|
| 80° C. | 0 | 1 | 2 | 3 | 7 |
| 60° C. |   |   |   |   | 29 |

(2) Analytical Test Methods

A 0.5 mL of sample solution was transferred to a 25 mL volumetric flask and QS'ed with methanol/water=95/5 for 25HC3S concentration determination by HPLC. The % remaining of 25HC3S was calculated as follows:

$$\% \text{ Remaining} = \frac{[25HC3S \text{ concentration}] \text{ at specified time point} \times 100}{[25HC3S \text{ concentration}] \text{ at time } 0}$$

Results and Discussion (1) Effect of Buffer Concentrations on the Stability of Formulations, Stressed at 80° C. for up to 7 Days or 60° C. for 29 Days There was no significant buffer concentration effect on the chemical stability for 25HC3S at 30 mg/mL in 250 mg/mL HPBCD containing phosphate buffers at 10, 20, 50 and 100 mM or borate buffers at 10 or 50 mM.

Figure 15:
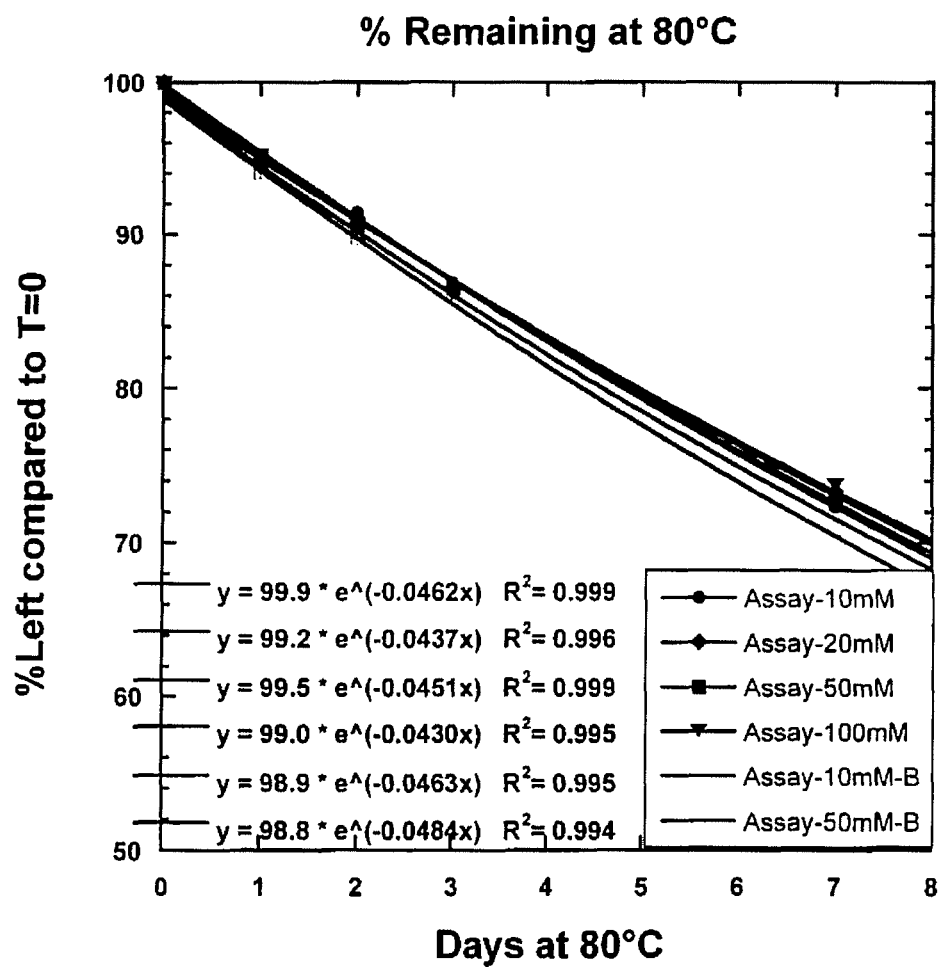
FIG. 15. Plot of % remaining 25HC3S in various buffers as function of time at 80° C. fitted to first order decay.

When stressed at 80° C. for 7 days, the % remaining of 25HC3S was 72.3, 73.3, 72.8 and 73.7% for the formulations containing 10, 20, 50 and 100 mM phosphate buffers, respectively (Table 26). The % remaining of 25HC3S after 7 days at 80° C. was 71.9 and 70.9% for the formulations containing 10 and 50 mM borate buffers, respectively (Table 26). FIG. 15 shows the % remaining of 25HC3S for each formulation, fitted to a first order curve for drug degradation. Table 27 shows the calculated time for which 90% of 25HC3S remains in the formulation (t90) at 80° C. The t90 values show that the phosphate buffer concentrations from 10 to 100 mM have no major effect on 25HC3S stability. In addition, the borate buffers at 10 and 50 mM have no major effect on 25HC3S stability.

TABLE 26

Stability of 25HC3S at 30 mg/mL in 250 mg/mL HPBCD containing 10, 20, 50 and 100 mM Phosphate or 10 and 50 mM Borate Buffers Stressed at 80° C.

| Time Point (Days) | Buffer | Buffer (mM) | 25HC3S (mg/mL) | % Remaining of 25HC3S | Osmolality (mmole/kg) | pH | Appearance |
|---|---|---|---|---|---|---|---|
| 0 | Phosphate | 10 | 28.45 | 100.0 | 273 | 8.09 | Clear |
| 1 |   |   | 27.03 | 95.0 | 291 | 7.28 | colorless |
| 2 |   |   | 26.00 | 91.4 | 286 | 6.82 | solution |
| 3 |   |   | 24.70 | 86.8 | 294 | 6.34 |   |
| 7 |   |   | 20.58 | 72.3 | 300 | 2.67 |   |
| 0 |   | 20 | 28.63 | 100.0 | 311 | 7.81 |   |
| 1 |   |   | 27.03 | 94.4 | 325 | 7.35 |   |
| 2 |   |   | 26.05 | 91.0 | 328 | 7.13 |   |
| 3 |   |   | 24.70 | 86.3 | 328 | 6.80 |   |
| 7 |   |   | 21.00 | 73.3 | 354 | 5.75 |   |
| 0 |   | 50 | 28.50 | 100.0 | 415 | 7.63 |   |
| 1 |   |   | 27.13 | 95.2 | 427 | 7.42 |   |
| 2 |   |   | 25.83 | 90.6 | 432 | 7.29 |   |
| 3 |   |   | 24.65 | 86.5 | 423 | 7.08 |   |
| 7 |   |   | 20.75 | 72.8 | 453 | 6.73 |   |
| 0 |   | 100 | 28.58 | 100.0 | 573 | 7.53 | Clear |
| 1 |   |   | 27.10 | 94.8 | 589 | 7.42 | colorless |
| 2 |   |   | 25.83 | 90.4 | 585 | 7.33 | solution |
| 3 |   |   | 24.65 | 86.2 | 589 | 7.15 |   |
| 7 |   |   | 21.05 | 73.7 | 616 | 6.93 | Clear brown solution |
| 0 | Borate | 10 | 28.58 | 100.0 | 316 | 9.36 | Clear |
| 1 |   |   | 26.90 | 94.1 | 318 | 9.12 | colorless |
| 2 |   |   | 25.63 | 89.7 | 323 | 8.92 | solution |

TABLE 26-continued

Stability of 25HC3S at 30 mg/mL in 250 mg/mL HPBCD containing 10, 20, 50 and 100 mM Phosphate or 10 and 50 mM Borate Buffers Stressed at 80° C.

| Time Point (Days) | Buffer | Buffer (mM) | 25HC3S (mg/mL) | % Remaining of 25HC3S | Osmolality (mmole/kg) | pH | Appearance |
|---|---|---|---|---|---|---|---|
| 3 | | | 24.40 | 85.4 | 328 | 8.60 | |
| 7 | | | 20.55 | 71.9 | 352 | 7.06 | Clear colorless solution at 80° C. when cooled to RT, ppt formed |
| 0 | | 50 | 28.50 | 100.0 | 524 | 9.40 | Clear |
| 1 | | | 26.78 | 94.0 | 527 | 9.34 | colorless |
| 2 | | | 25.45 | 89.3 | 534 | 9.28 | solution |
| 3 | | | 24.05 | 84.4 | 535 | 9.12 | |
| 7 | | | 20.20 | 70.9 | 569 | 8.92 | Clear brown solution at 80° C. when cooled to RT, ppt formed |

Precipitate = ppt

TABLE 27

Calculated t90 Values (Days) for 25HC3S at 80° C.

| Buffer | Concentration (mM) | Intercept | First Order Rate Constant | Calculated t90 (days) |
|---|---|---|---|---|
| Phosphate | 10 | 99.9 | −0.0462 | 2.3 |
| Phosphate | 20 | 99.2 | −0.0437 | 2.2 |
| Phosphate | 50 | 99.5 | −0.0451 | 2.2 |
| Phosphate | 100 | 99 | −0.0430 | 2.2 |
| Borate | 10 | 98.9 | −0.0463 | 2.0 |
| Borate | 50 | 98.8 | −0.0484 | 1.9 |

The impurity profiles for the formulations stressed at 80° C. are shown in Table 28. The major degradant is the hydrolysis product, 25-hydroxy cholesterol, which steadily increases over time at all conditions. The other observed degradant at relative retention time (RRT) of 2.64, typically did not increase when stability tested.

TABLE 28

Impurity profile for 25HC3S at 30 mg/mL in 250 mg/mL HPBCD containing 10, 20, 50 and 100 mM Phosphate or 10 and 50 mM Borate Buffers Stressed at 80° C.

| Time Point (Days) | Buffer | Buffer (mM) | % Peak Area | | |
|---|---|---|---|---|---|
| | | | Major Thermal Degradant at RRT = 2.64 | 25-Hydroxy Cholesterol at RRT = 3.67 | 25HC3S |
| 0 | Phosphate | 10 | 0.3 | 0.0 | 99.8 |
| 1 | | | 0.3 | 0.9 | 98.9 |
| 2 | | | 0.3 | 1.9 | 97.9 |
| 3 | | | 0.2 | 4.3 | 95.6 |
| 7 | | | 0.7 | 27.1 | 72.3 |
| 0 | | 20 | 0.3 | 0.0 | 99.7 |
| 1 | | | 0.3 | 1.0 | 98.8 |
| 2 | | | 0.2 | 1.9 | 98.0 |
| 3 | | | 0.2 | 3.5 | 96.4 |
| 7 | | | 0.2 | 19.8 | 79.9 |
| 0 | | 50 | 0.3 | 0.0 | 99.7 |
| 1 | | | 0.2 | 1.0 | 98.9 |
| 2 | | | 0.3 | 2.0 | 97.8 |
| 3 | | | 0.3 | 3.3 | 96.5 |
| 7 | | | 0.2 | 11.6 | 88.2 |
| 0 | | 100 | 0.3 | 0.0 | 99.8 |
| 1 | | | 0.3 | 0.9 | 98.8 |

TABLE 28-continued

Impurity profile for 25HC3S at 30 mg/mL in 250 mg/mL HPBCD containing 10, 20, 50 and 100 mM Phosphate or 10 and 50 mM Borate Buffers Stressed at 80° C.

| Time Point (Days) | Buffer | Buffer (mM) | Major Thermal Degradant at RRT = 2.64 | 25-Hydroxy Cholesterol at RRT = 3.67 | 25HC3S |
|---|---|---|---|---|---|
| 2 | | | 0.3 | 2.0 | 97.8 |
| 3 | | | 0.3 | 3.2 | 96.6 |
| 7 | | | 0.2 | 9.8 | 90.0 |
| 0 | Borate | 10 | 0.3 | 0.0 | 99.7 |
| 1 | | | 0.3 | 1.0 | 98.8 |
| 2 | | | 0.3 | 1.9 | 97.9 |
| 3 | | | 0.3 | 2.8 | 97.0 |
| 7 | | | 0.2 | 7.3 | 92.5 |
| 0 | | 50 | 0.2 | 0.0 | 99.9 |
| 1 | | | 0.3 | 1.0 | 98.7 |
| 2 | | | 0.3 | 2.0 | 97.8 |
| 3 | | | 0.2 | 3.0 | 96.9 |
| 7 | | | 0.3 | 6.2 | 93.6 |

When stressed at 60° C. for 29 days, the % remaining of 35HC3S was 93.7, 93.5, 93.4 and 93.2% for the formulations containing 10, 20, 50 and 100 mM phosphate buffers, respectively (Table 28). The % remaining of 35HC3S was 92.9 and 94.8% for the formulations containing 10 and 50 mM borate buffers, respectively (Table 29).

TABLE 29

Stability of 25HC3S at 30 mg/mL in 250 mg/mL HPBCD containing 10, 20, 50 and 100 mM Phosphate or 10 and 50 mM Borate Buffers Stressed at 60° C.

| Time Point (Days) | Buffer | Buffer (mM) | 25HC3S (mg/mL) | % Remaining of 25HC3S | Osmolality (mmole/kg) | pH | Appearance |
|---|---|---|---|---|---|---|---|
| 0 | Phosphate | 10 | 28.45 | 100.0 | 273 | 8.09 | Clear |
| 29 | | | 26.65 | 93.7 | 281 | 7.04 | colorless |
| 0 | | 20 | 28.63 | 100.0 | 311 | 7.81 | solution |
| 29 | | | 26.78 | 93.5 | 322 | 7.17 | |
| 0 | | 50 | 28.50 | 100.0 | 415 | 7.63 | |
| 29 | | | 26.63 | 93.4 | 430 | 7.28 | |
| 0 | | 100 | 28.58 | 100.0 | 573 | 7.53 | |
| 29 | | | 26.63 | 93.2 | 592 | 7.28 | |
| 0 | Borate | 10 | 28.58 | 100.0 | 316 | 9.36 | Clear |
| 29 | | | 26.55 | 92.9 | 326 | 8.90 | colorless |
| 0 | | 50 | 28.50 | 100.0 | 524 | 9.40 | solution |
| 29 | | | 27.03 | 94.8 | 541 | 9.19 | |

The impurity profiles for the formulations stressed at 60° C. are shown in Table 30. As at 80° C., 25-hydroxy cholesterol increased when the formulations were stability tested, while the impurity at RRT 2.64 typically remained constant.

TABLE 30

Impurity Profile for 25HC3S at 30 mg/mL in 250 mg/mL HPBCD containing 10, 20, 50 and 100 mM Phosphate or 10 and 50 mM Borate Buffers Stressed at 60° C.

| Time Point (Days) | Buffer | Buffer (mM) | Major thermal degradant at RRT = 2.64 | 25-Hydroxy Cholesterol at RRT = 3.67 | 25HC3S |
|---|---|---|---|---|---|
| 0 | Phosphate | 10 | 0.3 | 0.0 | 99.8 |
| 29 | | | 0.3 | 1.4 | 98.3 |
| 0 | | 20 | 0.3 | 0.0 | 99.7 |
| 29 | | | 0.3 | 1.4 | 98.3 |
| 0 | | 50 | 0.3 | 0.0 | 99.7 |
| 29 | | | 0.3 | 1.4 | 98.3 |
| 0 | | 100 | 0.3 | 0.0 | 99.8 |

TABLE 30-continued

Impurity Profile for 25HC3S at 30 mg/mL in 250 mg/mL HPBCD containing 10, 20, 50 and 100 mM Phosphate or 10 and 50 mM Borate Buffers Stressed at 60° C.

| | | | % Peak Area | | |
|---|---|---|---|---|---|
| Time Point (Days) | Buffer | Buffer (mM) | Major thermal degradant at RRT = 2.64 | 25-Hydroxy Cholesterol at RRT = 3.67 | 25HC3S |
| 29 | | | 0.3 | 1.4 | 98.4 |
| 0 | Borate | 10 | 0.3 | 0.0 | 99.7 |
| 29 | | | 0.3 | 1.3 | 98.5 |
| 0 | | 50 | 0.2 | 0.0 | 99.9 |
| 29 | | | 0.3 | 1.3 | 98.5 |

(2) Effect of Buffer Concentrations on the Osmolality of Formulations, Stressed at 80° C. for Up to 7 Days and at 60° C. for 29 Days There was no significant buffer concentration effect on the osmolality for the stressed formulations.

When stressed at 80° C. for 7 days, the osmolality of 25HC3S formulations slightly increased to 300, 354, 453 and 616 mmole/kg from 273, 311, 415, 573 mmole/kg (time 0) for the formulations containing 10, 20, 50 and 100 mM phosphate buffers, respectively (Table 25). The osmolality of 25HC3S formulations slightly increased to 352 and 569 mmole/kg from 316 and 524 mmole/kg (time 0) for the formulations containing 10 and 50 mM borate buffers, respectively (Table 26).

Figure 16:
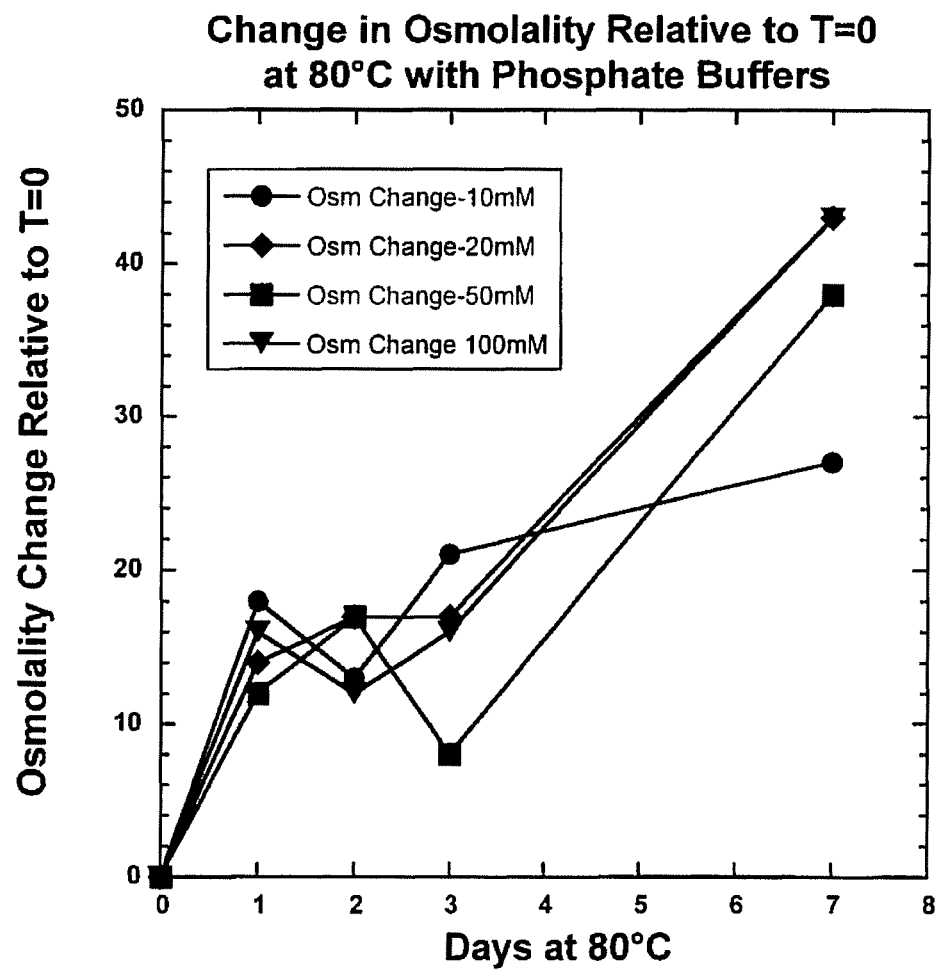
FIG. 16. Change in osmolality of phosphate buffers at 80° C.
Figure 17:
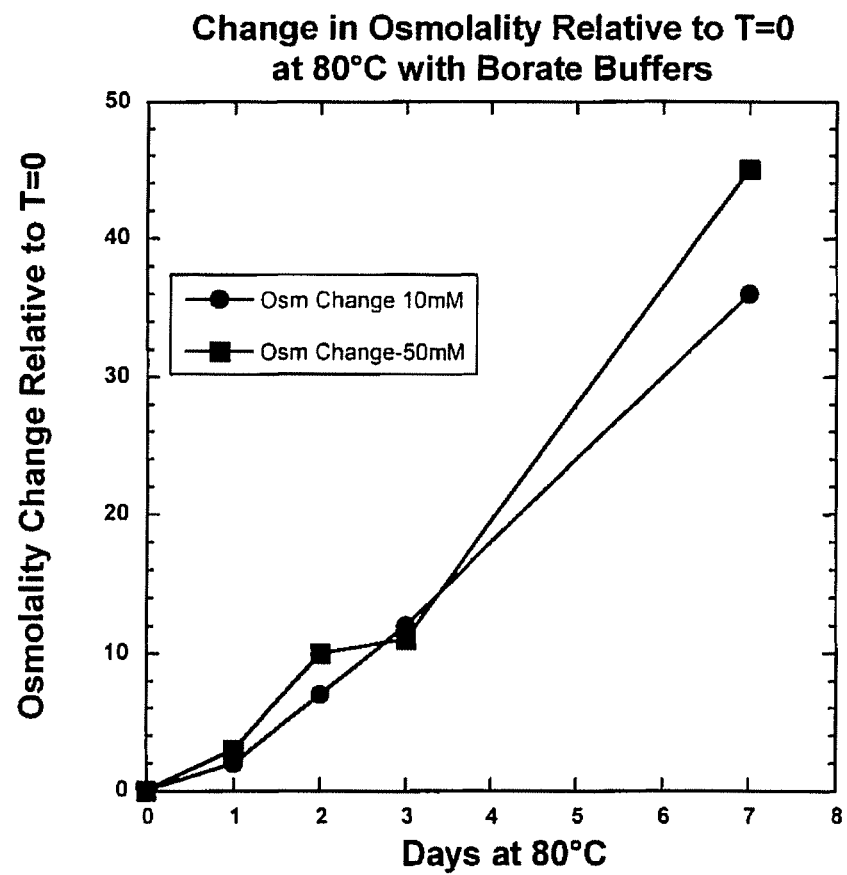
FIG. 17. Change in osmolality of borate buffers at 80° C.

FIG. 16 shows the change in osmolality from T=0 for the phosphate buffers at 80° C. FIG. 17 shows the change in osmolality from T=0 for the borate buffers at 80° C.

When stressed at 60° C. for 29 days, the osmolality increased to 281, 322, 430 and 592 mmole/kg from 273, 311, 415, and 573 mmole/kg (time 0) for the formulations containing 10, 20, 50 and 100 mM phosphate buffers, respectively (Table 28). The osmolality increased to 326 and 541 mmole/kg from 316 and 524 mmole/kg (time 0) for formulations containing 10 and 50 mM of borate buffers, respectively (Table 28).

The slight increase (ranging from approximately 25 to 45 mmole/kg) in osmolality for all formulations was possibly due to the hydrolysis of 25HC3S to form 25-Hydroxy Cholesterol and sodium bisulfate (Tables 25 and 28) or hydrolysis of HPBCD.

(3) Effect of Buffer Concentration on the pH Values of Formulations, Stressed at 80° C. for Up to 7 Days and 60° C. for 29 Days Under the stress conditions, the acidity of the formulation increased.

Formulations with higher concentration of buffer (either phosphate or borate) showed greater buffer capacity, resulting in less change of pH values for the formulation.

Figure 18:
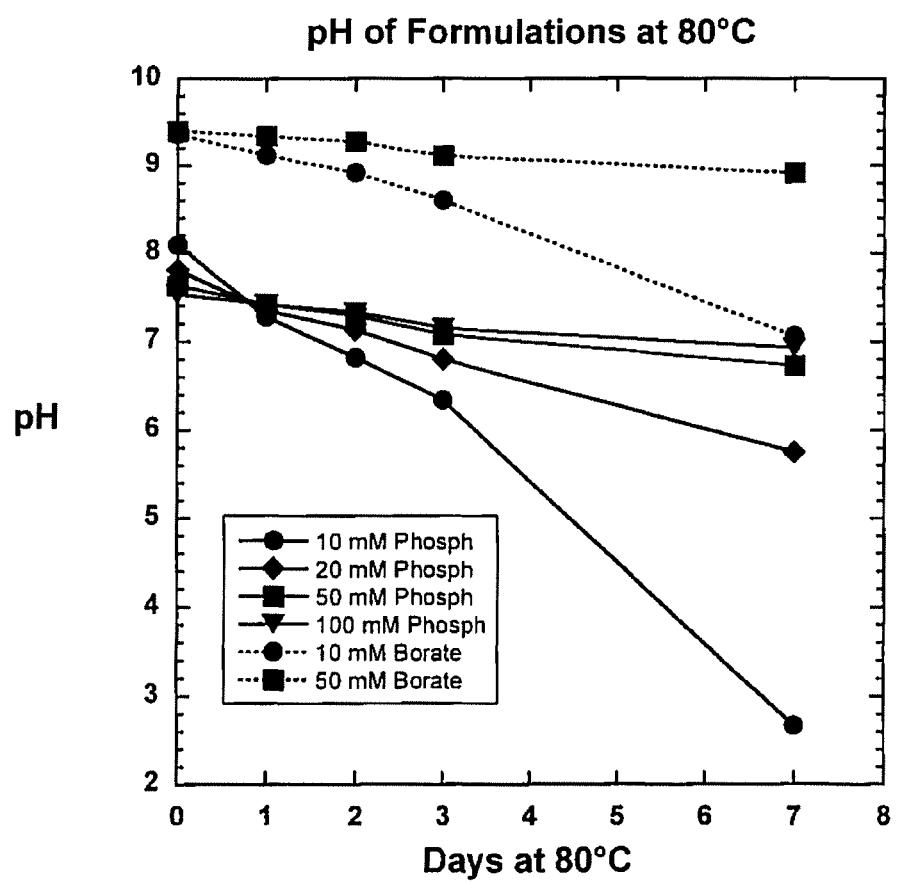
FIG. 18. pH of formulations at 80° C.
Figure 19:
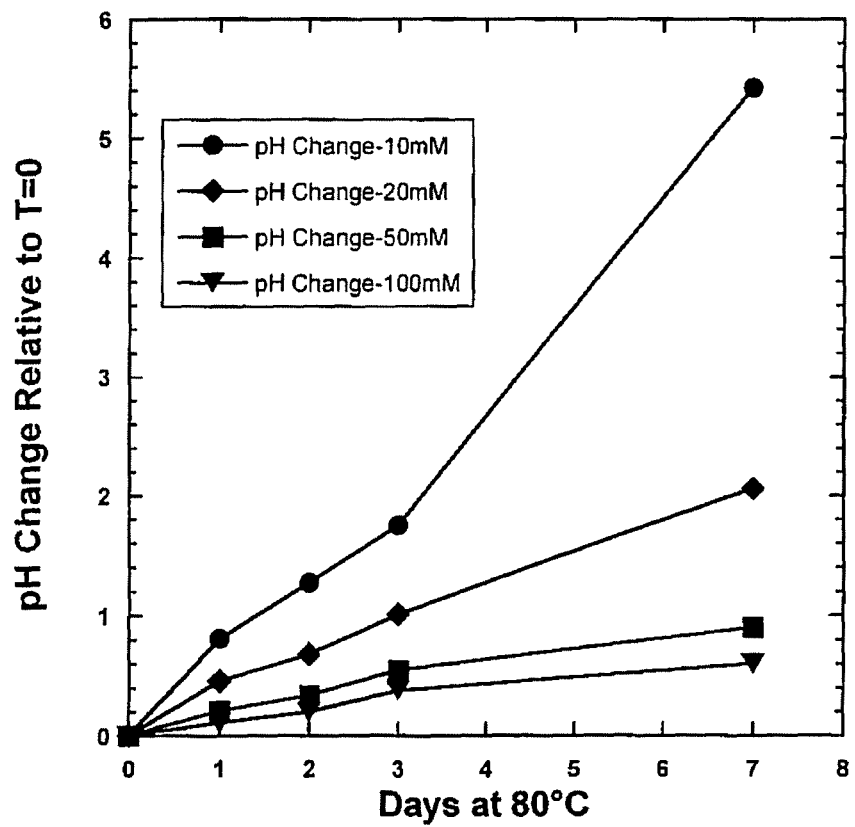
FIG. 19. Change in pH of phosphate buffers at 80° C.
Figure 20:
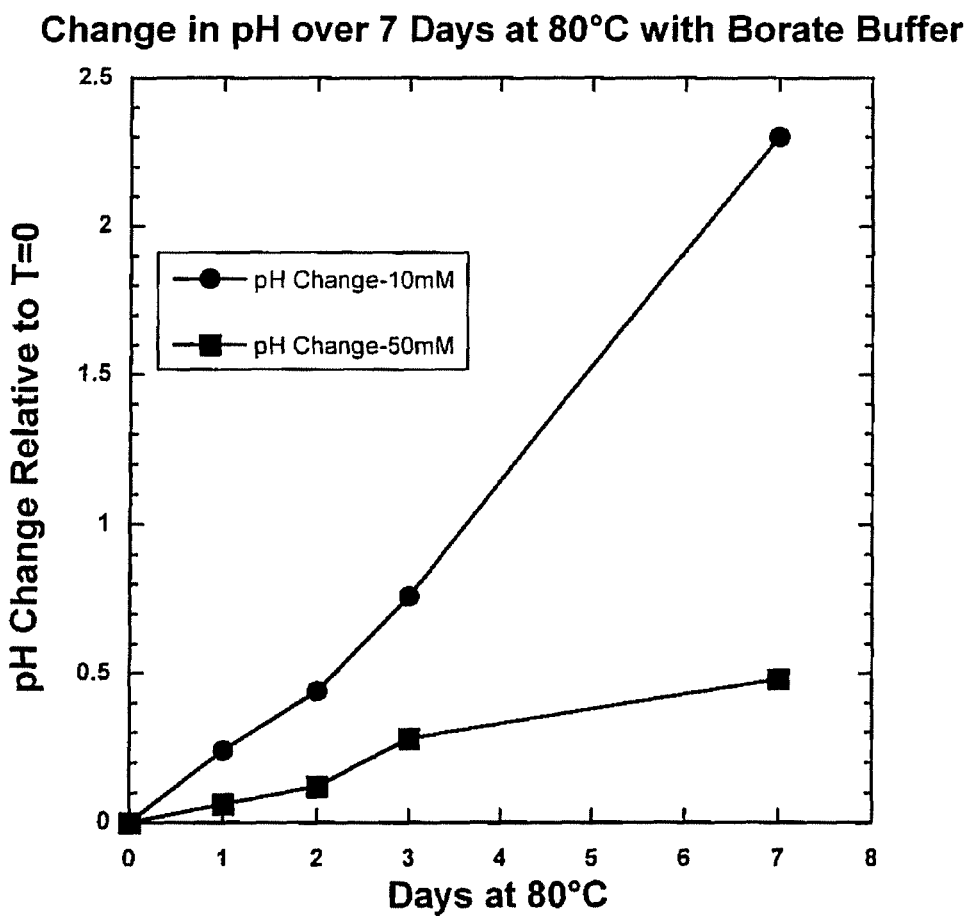
FIG. 20. Change in pH of borate buffers at 80° C.

When stressed at 80° C. for 7 days, the pH values of 35HC3S formulations decreased to 2.67, 5.75, 6.73 and 6.93 from 8.09, 7.81, 7.63, 7.53 (pH at time 0) for the formulations containing 10, 20, 50 and 100 mM phosphate buffers, respectively (Table 26). The pH values of 35HC3S formulations decreased to 7.06 and 8.92 from 9.36 and 9.40 (pH at time 0) for the formulations containing 10 and 50 mM borate buffers, respectively (Table 26). FIG. 18 shows the pH of the formulations at 80° C. FIGS. 19 and 20 show the change in pH from T=0 for the phosphate and borate buffer formulations, respectively.

When stressed at 60° C. for 29 days, the pH values of 35HC3S formulations decreased to 7.04, 7.17, 7.28 and 7.28 for the formulations containing 10, 20, 50 and 100 mM phosphate buffers, respectively (Table 28). The pH values of 35HC3S formulations decreased to 8.90 and 9.19 for the formulations containing 10 and 50 mM borate buffers, respectively (Table 28).

(4) Effect of Buffer Concentration on the Physical Appearance of Formulations, Stressed at 80° C. for Up to 7 Days and 60° C. for Up to 29 Days In some cases, both buffer types and buffer concentrations showed significant effect on the appearance of 35HC3S formulations.

When stressed at 80° C. for up to 7 days, formulations containing phosphate buffers at 10, 20 and 50 mM remained unchanged as colorless clear solutions. Formulation containing 100 mM phosphate turned to brown clear solution. When stressed at 80° C. for up to 7 days, formulations containing 10 or 50 mM borate buffers formed light brown and brown clear solutions, respectively. When these two borate formulations were removed from the 80° C. oven and cooled to room temperature, a white precipitate was observed (Table 25).

When stressed at 60° C. for 29 days, all six formulations showed clear colorless solutions (Table 28). Possibly the stress duration was not long enough to show the effect of buffer types and concentrations.

CONCLUSION

Buffer concentration showed no effect on the chemical stability and osmolality of all six formulations under accelerated temperature at 80° C. for 7 days or 60° C. for 29 days. The formulation containing 100 mM phosphate showed the best buffer capacity with the least pH change when stressed at 80° C. for 7 days, however, it turned brown. Formulations containing borate buffers at 10 and 50 mM also turned brown, and precipitation was observed when cooled to room temperature.

35HC3S at 30 mg/mL in 250 mg/mL of HPBCD containing 50 mM phosphate buffer at pH 7.63 showed the best stability among the six formulations. When stressed at 80° C. for 7 days or 60° C. for 29 days, the formulation remained unchanged as a colorless clear solution and no precipitate was observed when removed from 80° C. oven and cooled to ambient room temperature.

Example 12. Topical Formulation Physical Stability Testing

Methods

The formulation shown in below Table 31. The formulation was prepared by following the below steps:
1) Drug was dissolved in a solution of HPbCD in water.
2) Isopropyl palmitate and Tween 60 were mixed with molten cetyl alcohol at 60° C.
3) Drug solution was added to the mixture of cetyl alcohol/IPM and Tween 60 and mixed until a uniform cream was formed.

Results

The appearance of the resulting formulation is shown in below Table 31. The formulation was left at room temperature for 2 months. Its physical stability was recorded as shown in below Table 31.

TABLE 31

Formulation for Physical Stability Studies

| Components, % w/w | Form ID 44 |
|---|---|
| 25HC3S | 1 |
| HPbCD | 5.9 |
| IPM | 39.6 |
| Cetyl alcohol | 9.9 |
| Tween 60 | 9.9 |
| Water | 33.7 |
| Appearance | Cream |
| Physical stability at room temperature after 2 months | Stable cream Cetyl alcohol solidified |

Example 13. Injectable Formulation

Formulations are manufactured as shown in Table 32.

TABLE 32

| 25HC3S (mg/mL) | 12 | 30 |
|---|---|---|
| HPbCD (mg/mL) | 96 | 240 |
| Sodium phosphate buffer (mM) | 50 | 50 |

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

For all numeric ranges provided herein, it should be understood that the ranges include all integers between the highest and lowest value of the range, as well as all decimal fractions lying between those values, e.g. in increments of 0.1.

For all numeric values provided herein, the value is intended to encompass all statistically significant values surrounding the numeric value.

While the disclosure has been described in terms of its preferred embodiments, those skilled in the art will recognize that the disclosure can be practiced with modification within the spirit and scope of the appended aspects and claims. Accordingly, the present disclosure should not be limited to the embodiments as described above, but should further include all modifications and equivalents thereof within the spirit and scope of the description provided herein.

The invention claimed is:

1. A method of treating alcoholic hepatitis in a subject in need thereof, comprising intravenously administering an effective amount of an aqueous pharmaceutical composition comprising:
    5-cholesten-3,25-diol, 3-sulfate (25HC3 S) or pharmaceutically acceptable salt thereof,
    at least one buffer, and
    at least one cyclic oligosaccharide comprising at least one of hydroxypropyl β-cyclodextrin and sulfobutyl ether β-cyclodextrin.

2. The method of claim 1, wherein the 25HC3 S or pharmaceutically acceptable salt thereof comprises a pharmaceutically acceptable salt of 25HC3 S.

3. The method of claim 1, wherein the at least one cyclic oligosaccharide is present in the aqueous pharmaceutical composition at a concentration ranging from 0.1% (w/w) to 90% (w/w).

4. The method of claim 1, wherein the aqueous pharmaceutical composition has an osmolality ranging from 270 mmol/kg to 340 mmol/kg.

5. The method of claim 1, wherein the 25HC3S or pharmaceutically acceptable salt thereof is administered at a dose ranging from 0.001 mg/kg to 100 mg/kg.

6. The method of claim 1, wherein the 25HC3 S or pharmaceutically acceptable salt thereof is administered at a dose ranging from 0.001 mg/kg to 10 mg/kg.

7. The method of claim 1, wherein the 25HC3 S or pharmaceutically acceptable salt thereof is administered at a dose ranging from 0.1 mg/kg to 10 mg/kg.

8. The method of claim 2, wherein the 25HC3 S or pharmaceutically acceptable salt thereof is administered at a dose ranging from 0.001 mg/kg to 10 mg/kg.

9. The method of claim 3, wherein the 25HC3 S or pharmaceutically acceptable salt thereof is administered at a dose ranging from 0.001 mg/kg to 10 mg/kg.

10. The method of claim 1, wherein the 25HC3 S or pharmaceutically acceptable salt thereof comprises a sodium salt of 25HC3S.

11. The method of claim 1, wherein the at least one cyclic oligosaccharide comprises hydroxypropyl β-cyclodextrin.

12. The method of claim 1, wherein the 25HC3 S or pharmaceutically acceptable salt thereof is present in the aqueous pharmaceutical composition at a concentration ranging from 0.01% (w/w) to 3% (w/w).

13. The method of claim 8, wherein the 25HC3 S or pharmaceutically acceptable salt thereof is present in the aqueous pharmaceutical composition at a concentration ranging from 0.01% (w/w) to 3% (w/w).

14. The method of claim 1, wherein the 25HC3 S or pharmaceutically acceptable salt thereof is present in the aqueous pharmaceutical composition at a concentration ranging from 0.1 mg/mL to 50 mg/mL.

15. The method of claim 8, wherein the 25HC3 S or pharmaceutically acceptable salt thereof is present in the aqueous pharmaceutical composition at a concentration ranging from 0.1 mg/mL to 50 mg/mL.

16. The method of claim 1, wherein the at least one cyclic oligosaccharide is present in the aqueous pharmaceutical composition at a concentration ranging from 0.1% (w/w) to 40% (w/w).

17. The method of claim 8, wherein the at least one cyclic oligosaccharide is present in the aqueous pharmaceutical composition at a concentration ranging from 0.1% (w/w) to 40% (w/w).

18. The method of claim 1, wherein the at least one buffer is present in the aqueous pharmaceutical composition at a concentration ranging from 0.1 mM to 50 mM.

19. The method of claim 8, wherein the at least one buffer is present in the aqueous pharmaceutical composition at a concentration ranging from 0.1 mM to 50 mM.

20. The method of claim 1, wherein
- the 25HC3 S or pharmaceutically acceptable salt thereof comprises a sodium salt of 25HC3 S,
- the at least one cyclic oligosaccharide comprises hydroxypropyl β-cyclodextrin,
- the 25HC3 S or pharmaceutically acceptable salt thereof is present in the aqueous pharmaceutical composition at a concentration ranging from 0.01% (w/w) to 3% (w/w),
- the at least one cyclic oligosaccharide is present in the aqueous pharmaceutical composition at a concentration ranging from 0.1% (w/w) to 40% (w/w), and
- the at least one buffer is present in the aqueous pharmaceutical composition at a concentration ranging from 0.1 mM to 50 mM.

* * * * *

UNITED STATES PATENT AND TRADEMARK OFFICE
CERTIFICATE OF CORRECTION

PATENT NO. : 11,406,646 B2
APPLICATION NO. : 17/094432
DATED : August 9, 2022
INVENTOR(S) : Shunlin Ren et al.

It is certified that error appears in the above-identified patent and that said Letters Patent is hereby corrected as shown below:

In the Specification

Column 2, Line 12, replace "13" with --1β--

Column 4, Line 19, replace "ally" with --ally1--

Column 11, Line 32, replace "13-CD" with --1β -CD--

Column 11, Line 36, before "hydroxypropyl-" insert --(e.g.,--

Column 17, Line 63, replace "fon iulation" with --formulation--

Column 44, Line 64, replace "mM." with --min.--

Column 45, Line 15, replace "f3-CD" with --β-CD--

Column 47, Line 31, replace "Ing/mL" with --mg/mL--

Column 50, Line 3, replace "a" with --α--

Column 58, Line 18, replace "25HC35" with --25HC3S--

Signed and Sealed this
Sixth Day of December, 2022

Katherine Kelly Vidal
*Director of the United States Patent and Trademark Office*